US007250283B2

(12) United States Patent
Spiegelman et al.

(10) Patent No.: US 7,250,283 B2
(45) Date of Patent: Jul. 31, 2007

(54) PGC-1 ISOFORMS AND USES THEREFOR

(75) Inventors: Bruce M. Spiegelman, Waban, MA (US); Guillaume Adelmant, Boston, MA (US); Pere Puigserver, Brookline, MA (US)

(73) Assignee: Dana-Farber Cancer Institute, Boston, MA (US)

( * ) Notice: Subject to any disclaimer, the term of this patent is extended or adjusted under 35 U.S.C. 154(b) by 263 days.

(21) Appl. No.: 10/482,094

(22) PCT Filed: Jul. 3, 2002

(86) PCT No.: PCT/US02/21337

§ 371 (c)(1),
(2), (4) Date: Jul. 20, 2004

(87) PCT Pub. No.: WO03/004613

PCT Pub. Date: Jan. 16, 2003

(65) Prior Publication Data

US 2004/0254362 A1    Dec. 16, 2004

Related U.S. Application Data

(60) Provisional application No. 60/303,468, filed on Jul. 5, 2001.

(51) Int. Cl.
*C12N 1/20* (2006.01)
*C12N 9/02* (2006.01)
*C12N 15/00* (2006.01)
*C07H 21/04* (2006.01)

(52) U.S. Cl. ............... 435/252.3; 435/189; 435/320.1; 536/23.1; 536/23.2

(58) Field of Classification Search .............. 435/69.1, 435/252.3, 320.1, 189; 536/23.1, 23.2
See application file for complete search history.

(56) References Cited

U.S. PATENT DOCUMENTS 6,166,192 A    12/2000    Spiegelman et al.

FOREIGN PATENT DOCUMENTS

| WO | WO 98/54220 A1 | 12/1998 |
| WO | WO 00/32215 | 6/2000 |
| WO | WO 01/35096 | 5/2001 |

OTHER PUBLICATIONS

Sequence search alignment between Accession No. AF049330 and SEQ ID No. 6.*
Abu-Elheiga, L. et al. "Continuous fatty acid oxidation and reduced fat storage in mice lacking acetyl-CoA carboxylase 2." (2001) *Science* 291(5513):2613-6.
Amery, L. et al. "C-terminal tripeptide Ser-Asn-Leu (SNL) of human D-aspartate oxidase is a functional peroxisome-targeting signal." (1998) *Biochem. J.* 336(Pt. 2):367-71.

Aoyama, T. et al. "Altered constitutive expression of fatty acid-metabolizing enzymes in mice lacking the peroxisome proliferator-activated receptor α(PPARα)." (1998) *J. Biol. Chem.* 273(10):5678-84.
Clapham, J.C. et al. "Mice overexpressing human uncoupling protein-3 in skeletal muscle are hyperphagic and lean." (2000) *Nature* 406(6794):415-8.
Cooper, J.A. et al. "Phosphorylation sites in enolase and lactate dehydrogenase utilized by tyrosine protein kinases in vivo and in vitro." (1984) *J. Biol. Chem.* 259:7835-7841.
Djouadi, F. et al. "A gender-related defect in lipid metabolism and glucose homeostasis in peroxisome proliferator- activated receptor α—deficient mice." (1998) *J. Clin. Invest.* 102(6):1083-91.
Fan, C.Y. et al. "Steatohepatitis, spontaneous peroxisome proliferation and liver tumors in mice lacking peroxisomal fatty acyl-CoA oxidase. Implications for peroxisome proliferator-activated receptor alpha natural ligand metabolism." (1998) *J. Biol. Chem.* 273(25):15639-45.
Feramisco, J.R. et al. "Optimal spatial requirements for the location of basic residues in peptide substrates for the cyclic AMP-dependent protein kinase." (1980) *J. Biol. Chem.* 255:4240-4245.
Fruebis, J. et al. "Proteolytic cleavage product of 30-kDa adipocyte complement-related protein increases fatty acid oxidation in muscle and causes weight loss in mice." (2001) *Proc. Natl. Acad. Sci. USA* 98(4):2005-2010.
Glass, D.B. et al. "Phosphorylation by cyclic GMP-dependent protein kinase of a synthetic peptide corresponding to the autophosphorylation site in the enzyme." (1983) *J. Biol. Chem.* 258:14797-14803.
Glass, D.B. et al. "Synthetic peptides corresponding to the site phosphorylated in 6-phosphofructo-2-kinase/fructose-2,6-bisphosphatase as substrates of cyclic nucleotide-dependent protein kinases." (1986) *J. Biol. Chem.* 261:2987-2993.
Hashimoto, T. et al. "Defect in peroxisome proliferator-activated receptor α-inducible fatty acid oxidation determines the severity of hepatic steatosis in response to fasting." (2000) *J. Biol. Chem.* 275(37):28918-28.
Hunter, T. "Synthetic peptide substrates for a tyrosine protein kinase." (1982) *J. Biol. Chem.* 257:4843-4848.
Lehman, J.J. et al. "Peroxisome proliferator-activated receptor γcoactivator-1 promotes cardiac mitochondrial biogenesis." (2000) *J. Clin. Invest.* 106(7):847-56.

(Continued)

*Primary Examiner*—Tekchand Saidha
(74) *Attorney, Agent, or Firm*—Foley Hoag LLP

(57) ABSTRACT

The invention provides isolated nucleic acid molecules, designated PGC-1*b* and PGC-1*c* nucleic acid molecules, which encode novel isoforms of PGC-1 family members. The invention also provides antisense nucleic acid molecules, recombinant expression vectors containing PGC-1 nucleic acid molecules, host cells into which the expression vectors have been introduced, and nonhuman transgenic animals in which a PGC-1 gene has been introduced or disrupted. The invention still further provides isolated PGC-1 proteins, fusion proteins, antigenic peptides and anti-PGC-1 antibodies. Diagnostic methods utilizing compositions of the invention are also provided.

13 Claims, 8 Drawing Sheets

OTHER PUBLICATIONS

Levak-Frank, S. et al. "Muscle-specific overexpression of lipoprotein lipase causes a severe myopathy characterized by proliferation of mitochondria and peroxisomes in transgenic mice." (1995) *J. Clin. Invest.* 96(2):976-86.

Michael, L.F. et al. "Restoration of insulin-sensitive glucose transporter (GLUT4) gene expression in muscle cells by the transcriptional coactivator PGC-1." (2001) *Proc. Natl. Acad. Sci. USA* 98(7):3820-5.

Patschinsky, T. et al. "Analysis of the sequence of amino acids surrounding sites of tyrosine phosphorylation." (1982) *Proc. Natl. Acad. Sci. USA* 79:973-977.

Puigserver, P. et al. "A cold-inducible coactivator of nuclear receptors linked to adaptive thermogenesis." (1998) *Cell* 92(6):829-39.

Puigserver, P. et al. "Activation of PPARγ coactivator-1 through transcription factor docking." (1999) *Science* 286(5443):1368-71.

Vega, R.B. et al. "The coactivator PGC-1 cooperates with peroxisome proliferator-activated receptor α in transcriptional control of nuclear genes encoding mitochondrial fatty acid oxidation enzymes." (2000) *Mol. Cell. Biol.* 20(5):1868-76.

Watanabe, K. et al. "Constitutive regulation of cardiac fatty acid metabolism through peroxisome proliferator-activated receptor α associated with age-dependent cardiac toxicity." (2000) *J. Biol. Chem.* 275(29):22293-9.

Wu, Z. et al. "Mechanisms controlling mitochondrial biogenesis and respiration through the thermogenic coactivator PGC-1." (1999) *Cell* 98(1):115-24.

European Search Report dated May 24, 2005.

Database EMBL., Accession No. AC020746, "Homo sapiens chromosome 3p clone RP11-1004L19, working draft sequence, 8 unordered pieces," Jan. 11, 2000, XP002329206.

\* cited by examiner

PGC-1b

```
GAATTCGGCACGAGGCCTGCATGAGTGTGTGCTGTGTGTCAGAGTGGATTGGAGTTG
AAAAAGCTTGACTGGCGTCATTCGGGAGCTGGATGGCTTGGGACATGTGCAGCCAAG
ACTCTGTATGGAGTGACATAGAGTGTGCTGCTCTGGTTGGTGAGGACCAGCCTCTTT
GCCCAGATCTTCCTGAACTTGACCTTTCTGAACTTGATGTGAATGACTTGGATACAG
ACAGCTTTCTGGGTGGATTGAAGTGGTGTAGCGACCAATCGGAAATCATATCCAACC
AGTACAACAATGAGCCTGCGAACATATTTGAGAAGATAGATGAAGAGAATGAGGCGA
ACTTGCTAGCGGTCCTCACAGAGACACTGGACAGTCTCCCCGTGGATGAAGACGGAT
TGCCCTCATTTGATGCACTGACAGATGGAGCCGTGACCACTGACAACGAGGCCAGTC
CTTCCTCCATGCCTGACGGCACCCCTCCCCCTCAGGAGGCAGAAGAGCCGTCTCTAC
TTAAGAAGCTCTTACTGGCACCAGCCAACACTCAGCTCAGCTACAATGAATGCAGCG
GTCTTAGCACTCAGAACCATGCAGCAAACCACACCCACAGGATCAGAACAAACCCTG
CCATTGTTAAGACCGAGAATTCATGGAGCAATAAAGCGAAGAGCATTTGTCAACAGC
AAAAGCCACAAAGACGTCCCTGCTCAGAGCTTCTCAAGTATCTGACCACAAACGATG
ACCCTCCTCACACCAAACCCACAGAAAACAGGAACAGCAGCAGAGACAAATGTGCTT
CCAAAAAGAAGTCCCATACACAACCGCAGTCGCAACATGCTCAAGCCAAACCAACAA
CTTTATCTCTTCCTCTGACCCCAGAGTCACCAAATGACCCCAAGGGTTCCCCATTTG
AGAACAAGACTATTGAGCGAACCTTAAGTGTGGAACTCTCTGGAACTGCAGCTCCAC
TAGTGCCAAGGGAGCATCCATGCATCATTACATCCAGGTCGATATTGAATGTCTTCA
TGCAAAGATGTCTTTCTAATTTATAAATATGAACACATCACACAACTTGTGTTCATT
CTATTAAAGGTGTAAAAACTAATTTGATTTCAAAATAGCTGTTGTTAGTAAAGCAAG
ATGAGAGAAAGGAGAATGTTCTTGTGGCAGAAGGCATTTAAATCTATTGCATATGGA
GATTTTTTTTCAGACACTACCAACAGGATTTTATGTCTGAAATGGAAATGGAAAGGC
AATGTCAGCCTAACAAGGTGATGGCTTGAAACACAAGACATGAAGGAACTTTGTTAG
GGACCAAAATAACTGGTCCCCAATTTTATGTATATACATACATGTTTTGGCTATCAC
TATAAACATGGTGAAAGCAATGGAGCTGTTTTATAACTGATAAAAGATGAATAGAA
CAAAATAACCAGCTGTCTTTTTACTCTCGGACCACTGGGTTCTGCCCATATTTCCTT
CCATTCACATATCTTTGGTTACCTTGTTTGAAATGGGGTAGACATGCGGTTAATTTG
GTTTGTTATTATATTATTTGTTTGAGGATTTCATAAATAAGTGCAATATATTTGCAT
CATTTCCACCCCAACACCTCCCAAAACCACCCATCTCAAATTCATTTACTCTTTTTC
TATAATTGTTTTTGTCATATATTACACACACACAAAGGCGCATACACACACACGCAC
ACACAGGCACACACACACACACACACACACACACACACACACACACACACTGAGAGT
TGCCCTAATTTAGGGTTGACCACTTAGGGTTCAGGTCTCATCCCTGAAAAATGAAGA
AGAAGAAGAAGAAGAAGAAGAAGAAGAAGAAGAAGAAGAAGAAGAAGAAGAAGAAAA
AAAAAAAAAAAA
```

Fig. 1

PGC-1b

MAWDMCSQDSVWSDIECAALVGEDQPLCPDLPELDLSE
LDVNDLDTDSFLGGLKWCSDQSEIISNQYNNEPANIFE
KIDEENEANLLAVLTETLDSLPVDEDGLPSFDALTDGA
VTTDNEASPSSMPDGTPPPQEAEEPSLLKKLLLAPANT
QLSYNECSGLSTQNHAANHTHRIRTNPAIVKTENSWSN
KAKSICQQQKPQRRPCSELLKYLTTNDDPPHTKPTENR
NSSRDKCASKKKSHTQPQSQHAQAKPTTLSLPLTPESP
NDPKGSPFENKTIERTLSVELSGTAAPLVPREHPCIIT
SRSILNVFMQRCLSNL

Fig. 2

PGC-1c

```
GAATTCGGCACGAGGTCAGAGTGGATTGGAGTTGAAAAAGCTTGACTGGCGTCATTC
GGGAGCTGGATGGCTTGGGACATGTGCAGCCAAGACTCTGTATGGAGTGACATAGAG
TGTGCTGCTCTGGTTGGTGAGGACCAGCCTCTTTGCCCAGATCTTCCTGAACTTGAC
CTTTCTGAACTTGATGTGAATGACTTGGATACAGACAGCTTTCTGGGTGGATTGAAG
TGGTGTAGCGACCAATCGGAAATCATATCCAACCAGTACAACAATGAGCCTGCGAAC
ATATTTGAGAAGATAGATGAAGAGAATGAGGCAAACTTGCTAGCGGTCCTCACAGAG
ACACTGGACAGTCTCCCCGTGGATGAAGACGGATTGCCCTCATTTGATGCACTGACA
GATGGAGCCGTGACCACTGACAACGAGGCCAGTCCTTCCTCCATGCCTGACGGCACC
CCTCCCCCTCAGGAGGCAGAAGAGCCGTCTCTACTTAAGAAGCTCTTACTGGCACCA
GCCAACACTCAGCTCAGCTACAATGAATGCAGCGGTCTTAGCACTCAGAACCATGCA
GCAAACCACACCCACAGGATCAGAACAAACCCTGCCATTGTTAAGACCGAGAATTCA
TGGAGCAATAAAGCGAAGAGCATTTGTCAACAGCAAAAGCCACAAAGACGTCCCTGC
TCAGAGCTTCTCAAGTATCTGACCACAAACGATGACCCTCCTCACACCAAACCCACA
GAAAACAGGAACAGCAGCAGAGACAAATGTGCTTCCAAAAAGAAGTCCCATACACAA
CCGCAGTCGCAACATGCTCAAGCCAAACCAACAACTTTATCTCTTCCTCTGACCCCA
GAGTCACCAAATGACCCCAAGGGTTCCCCATTTGAGAACAAGACTATTGAGCGAACC
TTAAGTGTGGAACTCTCTGGAACTGCAGGTGTAAAAACTAATTTGATTTCAAAATAG
CTGTTGTTAGTTAAGCAAGATGAGAGAAAGGAGAATGTTCTTGTGGCAGAAGGCATT
TAAATCTATTGCATATGGAGATTTTTTTTCAGACACTACCAACAGGATTTTATGTCT
GAAATGGAAATGGAAAGGCAATGTCAGCCTAACAAGGTGATGGCTTGAAACACAAGA
CATGAAGGAACTTTGTTAGGGACCAAAATAACTGGTCCCAATTTTATGTATATACA
TACATGTTTTGGCTATCACTATAAACATGGTGAAAGCAATGGAGCTGTTTTATAACT
GATAAAAGATGAATAGAACAAAATAACCAGCTGTCTTTTTACTCTCGGACCACTGG
GTTCTGCCCATATTTCCTTCCATTCACATATCTTTGGTTACCTTGTTTGAAATGGGG
TAGACATGCGGTTAATTTGGTTTGTTATTATATTATTTGTTTGAGGATTTCATAAAT
AAGTGCAATATATTTGCATCATTTCCACCCCAACACCTCCCAAAACCACCCATCTCA
AATTCATTTACTCTTTTTCTATAATTGTTTTTGTCATATATTACACACACACAAAGG
CACNTACACACACACGCACACACAGGCACACACACACACACACACACACACACACAC
ACACACACACTGAGAATTGCCCTAATTTAGGGTTGACCACTTAGGGTTCAGTTTT
TTTCCCTGGAAAATGGGGGGGGGGAAAAAAAAAAAAAAAAAAAAAAAAAAAAAAAA
AAAAAAAAAAAAAAAAAAAAAAAAAAAAAAAA
```

Fig. 3

PGC-1c

MAWDMCSQDSVWSDIECAALVGEDQPLCPDLPELDLSEL
DVNDLDTDSFLGGLKWCSDQSEIISNQYNNEPANIFEKI
DEENEANLLAVLTETLDSLPVDEDGLPSFDALTDGAVTT
DNEASPSSMPDGTPPPQEAEEPSLLKKLLLAPANTQLSY
NECSGLSTQNHAANHTHRIRTNPAIVKTENSWSNKAKSI
CQQQKPQRRPCSELLKYLTTNDDPPHTKPTENRNSSRDK
CASKKKSHTQPQSQHAQAKPTTLSLPLTPESPNDPKGSP
FENKTIERTLSVELSGTAGVKTNLISK

Fig. 4

```
aaagcttgactggcgtcattcgggagctggATGGCTTGGGACATGTGCAGCCAAGACTCT
                               MetAlaTrpAspMetCysSerGlnAspSer GTATGGAGTGACATAGAGTGTGCTGCTCTGGTTGGTGAGGACCAGCCTCTTTGCCCAGAT
ValTrpSerAspIleGluCysAlaAlaLeuValGlyGluAspGlnProLeuCysProAsp CTTCCTGAACTTGACCTTTCTGAACTTGATGTGAATGACTTGGATACAGACAGCTTTCTG
LeuProGluLeuAspLeuSerGluLeuAapValAsnAspLeuAspThrAspSerPheLeu GGTGGATTGAAGTGGTGTAGCGACCAATCGGAAATCATATCCAACCAGTACAACAATGAG
GlyGlyLeuLysTrpCysSerAspGlnSerGluIleIleSerAsnGlnTyrAsnAsnGlu CCTGCGAACATATTTGAGAAGATAGATGAAGAGAATGAGGCAAACTTGCTAGCGGTCCTC
ProAlaAsnIlePheGluLysIleAspGluGluAsnGluAlaAsnLeuLeuAlaValLeu ACAGAGACACTGGACAGTCTCCCCGTGGATGAAGACGGATTGCCCTCATTTGATGCACTG
ThrGluThrLeuAspSerLeuProValAspGluAspGlyLeuProSerPheAspAlaLeu ACAGATGGAGCCGTGACCACTGACAACGAGGCCAGTCCTTCCTCCATGCCTGACGGCACC
ThrAspGlyAlaValThrThrAspAsnGluAlaSerProSerSerMetProAspGlyThr CCTCCCCCTCAGGAGGCAGAAGAGCCGTCTCTACTTAAGAAGCTCTTACTGGCACCAGCC
ProProProGlnGluAlaGluGluProSerLeuLeuLysLysLeuLeuLeuAlaProAla AACACTCAGCTCAGCTACAATGAATGCAGCGGTCTTAGCACTCAGAACCATGCAGCAAAC
AsnThrGlnLeuSerTyrAsnGluCysSerGlyLeuSerThrGlnAsnHisAlaAlaAsn CACACCCACAGGATCAGAACAAACCCTGCCATTGTTAAGACCGAGAATTCATGGAGCAAT
HisThrHisArgIleArgThrAsnProAlaIleValLysThrGluAsnSerTrpSerAsn AAAGCGAAGAGCATTTGTCAACAGCAAAAGCCACAAAGACGTCCCTGCTCAGAGCTTCTC
LysAlaLysSerIleCysGlnGlnGlnLysProGlnArgArgProCysSerGluLeuLeu AAGTATCTGACCACAAACGATGACCCTCCTCACACCAAACCCACAGAAAACAGGAACAGC
LysTyrLeuThrThrAsnAspAspProProHisThrLysProThrGluAsnArgAsnSer AGCAGAGACAAATGTGCTTCCAAAAAGAAGTCCCATACACAACCGCAGTCGCAACATGCT
SerArgAspLysCysAlaSerLysLysLysSerHisThrGlnProGlnSerGlnHisAla CAAGCCAAACCAACAACTTTATCTCTTCCTCTGACCCCAGAGTCACCAAATGACCCCAAG
GlnAlaLysProThrThrLeuSerLeuProLeuThrProGluSerProAsnAspProLys GGTTCCCCATTTGAGAACAAGACTATTGAGCGAACCTTAAGTGTGGAACTCTCTGGAACT
GlySerProPheGluAsnLysThrIleGluArgThrLeuSerValGluLeuSerGlyThr
    ↓
GCA
Ala
```

} COMMON TO ALL THREE ISOFORMS

Fig. 5A

```
_ GGCCTAACT_//_TTGCGCAGGTAAcgtgttcccaggctgaggaatgacagagagat
_ GlyLeuThr_//_LeuArgArg.                 PGC-1a protein 797 AAc
ggtcaatacctcatgggacagcgtgtcctttcccaagactcttgcaagtcatacttagga
Atttctcctactttacactctctgtacaaaaataaaacaaaacaaaacaacaataacaac
Aacaacaacaacaataacaacaacaaccataccagaacaagaacaacggtttacatgaac
Acagctgctgaagaggcaagagacagaatgataatccagtaagcacacgtttattcacgg
Gtgtcagctttgctttccctggaggctcttggtgacagtgtgtgtgcgtgtgtgtgtgtg
Ggtgtgcgtgtgtgtatgtgtgtgtgtgtacttgtttggaaagtacatatgtacacatgt
Gaggacttgggggcacctgaacagaacgaacaagggcgaccccttcaaatggcagcattt
Ccatgaagacacacttaaaacctacaacttcaaaatgttcgtattctatacaaaaggaaa
ataaataaatataaaaaaaaaaaaaaaaaaaa           PGC-1a mRNA
```
} PGC-1a SPECIFIC

```
_ GCTCCACTAGTGCCAAGGGAGCATCCATGCATCATTACATCCAGGTCGATATTGAAT
_ AlaProLeuValProArgGluHisProCysIleIleThrSerArgSerIleLeuAsn

GTCTTCATGCAAAGATGTCTTTCTAATTTATAAatatgaacacatcacacaacttgtgtt
ValPheMetGlnArgCysLeuSerAsnLeu.        PGC-1b protein 320 AAc
cattctattaaaggtgtaaaaactaatttgatttcaaaatagctgttgttagtaaagcaa
gatgagagaaaggagaatgttcttgtggcagaaggcatttaaatctattgcatatggaga
tttttttttcagacactaccaacaggatttatgtctgaaatggaaatggaaaggcaatgt
cagcctaacaaggtgatggcttgaaacacaagacatgaaggaactttgttagggaccaaa
ataactggtccccaatttatgtatatacatacatgttttggctatcactataaacatgg
tgaaagcaatggagctgttttataactgataaaaagatgaatagaacaaaataaccagct
gtcttttactctcggaccactgggttctgcccatatttccttccattcacatatctttg
gttaccttgtttgaaatggggtagacatgcggttaatttggtttgttattatattatttg
tttgaggatttcataaataagtgcaatatatttgcatcatttccaccccaacacctccca
aaaccacccatctcaaattcatttactcttttctataattgtttttgtcatatattaca
cacacacaaaggcgcatacacacacacgcacacacaggcacacacacacacacacacaca
cacacacacacacacacactgagagttgccctaatttagggttgaccacttagggttc
aggtctcatccctgaaaaatgaagaagaagaagaagaagaagaagaagaagaagaagaac
aagaagaagaagaagaaaaaaaaaaaaaaaaa         PGC-1b mRNA
```
} PGC-1b SPECIFIC

```
_ GGTGTAAAAACTAATTTGATTTCAAAATAGctgttgttagttaagcaagatgagaga
_ GlyValLysThrAsnLeuIleSerLys.          PGC-1c protein 300 AAc
aaggagaatgttcttgtggcagaaggcatttaaatctattgcatatggagattttttttc
agacactaccaacaggatttatgtctgaaatggaaatggaaaggcaatgtcagcctaac
aaggtgatggcttgaaacacaagacatgaaggaactttgttagggaccaaaataactggt
ccccaatttatgtatatacatacatgttttggctatcactataaacatggtgaaagcaa
tggagctgttttataactgataaaaagatgaatagaacaaaataaccagctgtcttttta
ctctcggaccactgggttctgcccatatttccttccattcacatatctttggttaccttg
tttgaaatggggtagacatgcggttaatttggtttgttattatattatttgtttgaggat
ttcataaataagtgcaatatatttgcatcatttccaccccaacacctcccaaaaccaccc
atctcaaattcatttactcttttctataattgtttttgtcatatattacacacacacaa
aggcacntacacacacacgcacacacaggcacacacacacacacacacacacacacacac
acacacacacactgagaattgccctaatttagggttgaccacttagggttcagttttttt
ccctggaaatggggggggggaaaaaaaaaaaaaaaaaaaaaaaaaaaaaaaaaaaaaaa
aaaaaaaaaaaaaaaaaaaaaaaaaaa             PGC-1c mRNA
```
} PGC-1c SPECIFIC

Fig. 5B

```
PGC-1a    -AATTCGGCACGAGGTTGCCTGCATGAGTGTGTGCTGTGTGTCAGAGTGGA
PGC-1b    GAATTCGGCACGAGG---CCTGCATGAGTGTGTGCTGTGTGTCAGAGTGGA
PGC-1c    GAATTCGGCACGAGG------------------------TCAGAGTGGA

PGC-1a    TTGGAGTTGAAAAAGCTTGACTGGCGTCATTCGGGAGCTGG (1-91)
PGC-1b    TTGGAGTTGAAAAAGCTTGACTGGCGTCATTCGGGAGCTGG (1-89)
PGC-1c    TTGGAGTTGAAAAAGCTTGACTGGCGTCATTCGGGAGCTGG (1-66)
```

Fig. 6

PGC-1 ISOFORMS AND USES THEREFOR

RELATED APPLICATIONS

This application claims the benefit of U.S. Provisional Application Ser. No. 60/303,468, filed Jul. 5, 2001, the entire contents of which are incorporated herein by this reference.

GOVERNMENT SUPPORT

Work described herein was supported under grant DK54477 awarded by the National Institutes of Health. The U.S. government may have certain rights in this invention.

BACKGROUND OF THE INVENTION

Heart and skeletal muscle rely primarily on fatty acid oxidation to support their energy needs. Fatty acids are transported between organs either as non-esterified fatty acid (NEFAs) or as triacylglycerols complexed to lipoproteins. Whereas the cellular uptake of NEFAs is thought to be facilitated by a protein facilitated mechanism involving a broad class of transporters (e.g., FABPm, FAT/CD36, and FATP), the uptake of lipoprotein borne fatty acids first requires the hydrolysis of the ester bond through the action of lipoprotein lipase (LPL). After becoming activated in the cytosol by acyl CoA synthetase, fatty-acyl-CoAs enter the beta oxidation pathway. Although mitochondria are the main site of oxidation for short and medium chain length fatty acids, longer chain fatty acids ($C_{22}$ and longer) are first oxidized in peroxisomes, until palmitoyl-CoA is formed, and further oxidized in the mitochondria. In addition to this chain shortening activity, peroxisomal beta oxidation is also responsible for the catabolism of a wide variety of fatty acid analogues such as dicarboxylic acids and prostaglandins.

Several animal models have stressed the importance of fatty acid oxidation in different tissues. For example, mice deficient in peroxisomal Acyl-CoA oxidase accumulate very long chain fatty acids (VLCFAs) in the blood, exhibit severe steatohepatitis (inflammation of the liver associated with fatty liver), and ultimately develop liver tumors (Fan, C. Y. et al. (1998) *J. Biol. Chem.* 273(25):15639-45). The fatty liver phenotype is also observed in response to fasting in mice lacking the transcription factor PPARα, highlighting its critical role for the induction of fatty acid oxidation enzymes in liver in response to nutritional challenge (Hashimoto, T. et al. (2000) *J. Biol. Chem.* 275(37):28918-28).

Conversely, uncontrolled fatty acid oxidation can also be detrimental. Transgenic mice overexpressing LPL in skeletal muscle and heart have increased free fatty acid (FFA) uptake in muscle and lower plasma triglyceride levels, but suffer from extensive mitochondrial and peroxisomal proliferation, leading to severe myopathy and premature death (Levak-Frank, S. et al. (1995) *J. Clin. Invest.* 96(2):976-86).

Although skeletal muscle is quantitatively the most important tissue for removing lipids from circulation, little is known about the factors that regulate fatty acid metabolism in this tissue. While compelling evidence supports the role of PPARα in the regulation of fatty acid oxidation in liver, recent data have shown that PPARα is not required for the constitutive expression of genes involved in peroxisomal beta oxidation in muscle (Djouadi, F. et al. (1998) *J. Clin. Invest.* 102(6):1083-91; Aoyama, T. et al. (1998) *J. Biol. Chem.* 273(10):5678-84; Watanabe, K. et al. (2000) *J. Biol. Chem.* 275(29):22293-9).

SUMMARY OF THE INVENTION

The present invention is based, at least in part, on the discovery of novel isoforms of the thermogenic co-activator PGC-1. These isoforms, referred to herein as PGC-1b and PGC-1c, encode two shorter proteins corresponding to the amino-terminal region of PGC-1, but lack the entirety of its carboxy-terminal RNA processing domain.

In one embodiment, the invention features an isolated nucleic acid molecule that includes the nucleotide sequence set forth in SEQ ID NO:6, 8, 9, 11, 12, 14, 15, or 17, or a complement thereof. In another embodiment, the invention features an isolated nucleic acid molecule which encodes a polypeptide which includes the amino acid sequence set forth in SEQ ID NO:7, 10, 13, or 16.

In other embodiments, the invention features nucleic acid molecules that are complementary to, antisense to, or hybridize under stringent conditions to the isolated nucleic acid molecules described herein.

In a related aspect, the invention provides vectors including the isolated nucleic acid molecules described herein (e.g., PGC-1-encoding nucleic acid molecules). Such vectors can optionally include nucleotide sequences encoding heterologous polypeptides. Also featured are host cells including such vectors (e.g., host cells including vectors suitable for producing PGC-1 nucleic acid molecules and polypeptides).

In another aspect, the invention features isolated PGC-1 polypeptides and/or biologically active or antigenic fragments thereof. Exemplary embodiments feature an isolated polypeptide including the amino acid sequence of SEQ ID NO:7, 10, 13, or 16.

The PGC-1 polypeptides and/or biologically active or antigenic fragments thereof, are useful, for example, as reagents or targets in assays applicable to treatment and/or diagnosis of PGC-1 associated disorders. In one embodiment, a PGC-1 polypeptide or fragment thereof has a PGC-1 activity. In another embodiment, a PGC-1 polypeptide or fragment thereof has at least one or more of the following domains or motifs: a tyrosine phosphorylation motif, a cAMP phosphorylation motif, an LXXLL motif, and/or a peroxisomal localization signal, and optionally, has a PGC-1 activity. In a related aspect, the invention features antibodies (e.g., antibodies which specifically bind to any one of the polypeptides, as described herein) as well as fusion polypeptides including all or a fragment of a polypeptide described herein.

The present invention further features methods for detecting PGC-1 polypeptides and/or PGC-1 nucleic acid molecules, such methods featuring, for example, a probe, primer or antibody described herein. Also featured are kits for the detection of PGC-1 polypeptides and/or PGC-1 nucleic acid molecules. In a related aspect, the invention features methods for identifying compounds which bind to and/or modulate the activity of a PGC-1 polypeptide or PGC-1 nucleic acid molecule described herein. Also featured are methods for modulating PGC-1 activity.

Other features and advantages of the invention will be apparent from the following detailed description and claims.

BRIEF DESCRIPTION OF THE DRAWINGS

FIG. 1 depicts the nucleotide sequence of PGC-1b (SEQ ID NO:6). The unique region is underlined.

FIG. 2 depicts the amino acid sequence of PGC-1b (SEQ ID NO:7). The unique region is underlined.

FIG. 3 depicts the nucleotide sequence of PGC-1c (SEQ ID NO:12). The unique region is underlined.

FIG. 4 depicts the amino acid sequence of PGC-1c (SEQ ID NO:13). The unique region is underlined.

FIG. 5 depicts the structural relationship between the PGC-1a, PGC-1b, and PGC-1c nucleotide and amino acid sequences. The common nucleotide region, most of which is shown at the top, corresponds to nucleotides 62-964 of SEQ ID NO:1 (PGC-1a), nucleotides 60-962 of SEQ ID NO:6 (PGC-1b), and 37-939 of SEQ ID NO:12 (PGC-1c). Only the last 30 nucleotides of the 5' untranslated region (immediately prior to the initiation codon) are shown. The common amino acid sequence (set forth as SEQ ID NO:5) corresponds to amino acid residues 1-291 of SEQ ID NO:2 (PGC-1a), SEQ ID NO:7 (PGC-1c), and SEQ ID NO:13 (PGC-1c). The PGC-1a specific sequences correspond to nucleotides 965-3066 of SEQ ID NO:1 and amino acid residues 292-797 of SEQ ID NO:2 (however, the entire specific nucleotide and amino acid sequences of PGC-1a are not shown in the figure). The PGC-1b specific sequences correspond to nucleotides 963-1893 of SEQ ID NO:6 (set forth as SEQ ID NO:9) and amino acid residues 292-320 of SEQ ID NO:7 (set forth as SEQ ID NO:10). The PGC-1c specific sequences correspond to nucleotides 940-1744 of SEQ ID NO:12 (set forth as SEQ ID NO:15) and amino acid residues 292-300 of SEQ ID NO:13 (set forth as SEQ ID NO:16).

FIG. 6 depicts an alignment of the 5' UTRs of PGC-1a, PGC-1b, and PGC-1c, corresponding to nucleotides 1-91 of SEQ ID NO:1 (PGC-1a), nucleotides 1-89 of SEQ ID NO:6 (PGC-1b), and nucleotides 1-66 of SEQ ID NO:12 (PGC-1c).

DETAILED DESCRIPTION OF THE INVENTION

Figure 7:
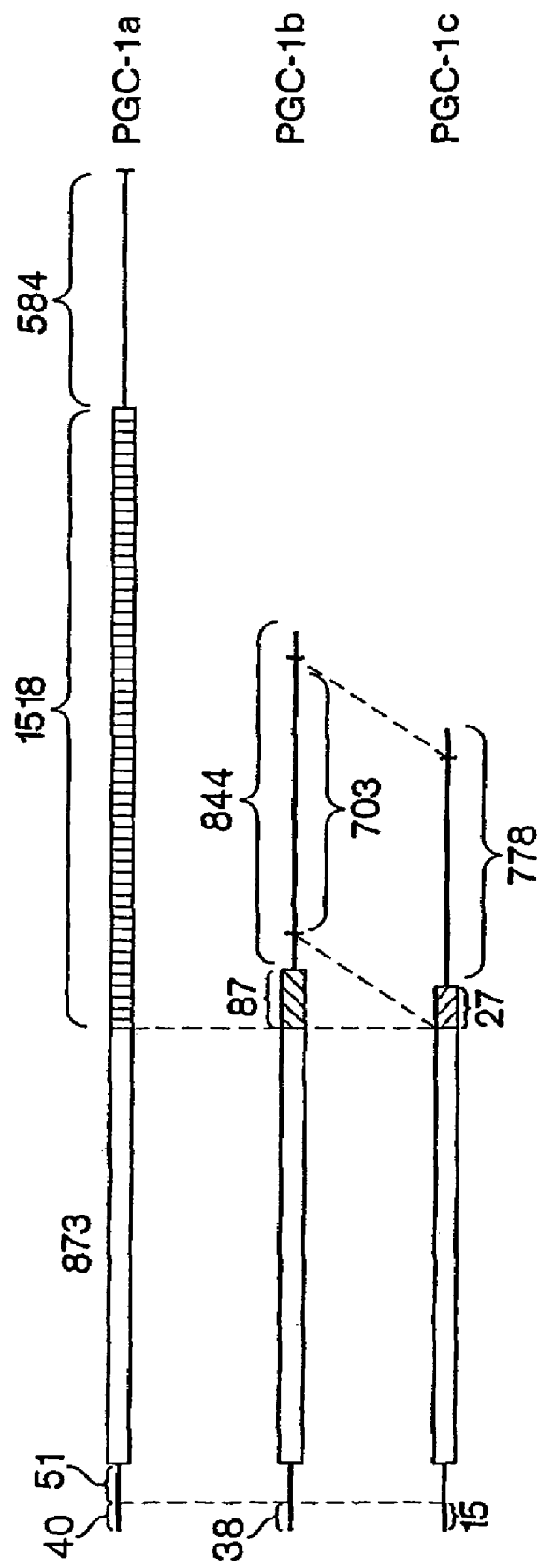
FIG. 7 depicts a schematic representation of the structural relationship between the nucleotide sequences of PGC-1a, PGC-1b, and PGC-1c. The coding regions are boxed. Open boxes represent the coding region common to all three isoforms, while hatched boxes represent the coding regions specific to each isoform. Dashed lines indicate points of divergence between the sequences of each isoform.

The present invention is based, at least in part, on the discovery of novel isoforms of the thermogenic co-activator PGC-1. These isoforms, referred to herein as PGC-1b and PGC-1c, encode two shorter proteins corresponding to the amino-terminal region of PGC-1, but lack the entirety of its carboxy-terminal RNA processing domain.

PGC-1 has been described previously (Puigserver, P. et al. (1998) *Cell* 92(6):829-39; U.S. Pat. No. 6,166,192; and PCT International Publication Nos. WO 98/54220; the contents of all of which are incorporated herein by reference). Based on the instant discovery of novel isoforms of PGC-1, the molecule previously referred to as "PGC-1" is referred to herein as "PGC-1a", and the term "PGC-1", as used herein, includes PGC-1a, PGC-1b, and PGC-1c. The nucleotide and amino acid sequences of PGC-1b are shown in FIGS. 1 and 2, respectively. The nucleotide and amino acid sequences of PGC-1c are shown in FIGS. 3 and 4, respectively. FIGS. 5 and 7 depict the structural relationship between PGC-1a, PGC-1b, and PGC-1c.

PGC-1b and PGC-1c are identical to PGC-1a at the 5' end of the nucleic acid sequence, although there are slight differences at the extreme 5' ends of the 5' untranslated regions (UTRs) of each isoform (see FIG. 6). Accordingly, the region common to all three isoforms (referred to herein as the "common region"; set forth as SEQ ID NO:4) corresponds to nucleotides 41-964 of PGC-1a (SEQ ID NO:1), nucleotides 39-962 of PGC-1b (SEQ ID NO:6), and nucleotides 16-939 of PGC-1c (SEQ ID NO:12). The nucleotide sequences of PGC-1b and PGC-1c each contain unique regions located 3' to the common region. The amino acid sequence common to all three isoforms (set forth as SEQ ID NO:5) corresponds to residues 1-291 of PGC-1a (SEQ ID NO:2), PGC-1b (SEQ ID NO:7), and PGC-1c (SEQ ID NO:13), and the unique region of each polypeptide starts at amino acid residue 292.

The unique region of PGC-1b corresponds to nucleotides 963-1893 of SEQ ID NO:6 (set forth as. SEQ ID NO.9). The entire coding region of PGC-1b, corresponding to nucleotides 90-1049 of SEQ ID NO:6, is set forth as SEQ ID NO:8 and encodes a polypeptide of 320 amino acid residues (set forth as SEQ ID NO:7). The unique coding region of PGC-1b, corresponding to nucleotides 963-1049 of SEQ ID NO:6, is set forth as SEQ ID NO:11 and encodes a unique C-terminus of 29 amino acid residues (set forth as SEQ ID NO:10).

The unique region of PGC-1c corresponds to nucleotides 940-1744 of SEQ ID NO:12 (set forth as SEQ ID NO:15). The entire coding region of PGC-1c, corresponding to nucleotides 67-966 of SEQ ID NO:12, is set forth as SEQ ID NO:14 and encodes a polypeptide of 300 amino acid residues (set forth as SEQ ID NO:13). The unique coding region of PGC-1c, corresponding to nucleotides 940-966 of SEQ ID NO:12, is set forth as SEQ ID NO:17 and encodes a unique C-terminus of 9 amino acid residues (set forth as SEQ ID NO:16). It should be noted that nucleotides 940-1648 of PGC-1c (SEQ ID NO:12) are actually present in the nucleotide sequence of PGC-1b (from nucleotides 1092-1859 of SEQ ID NO:6), but are not translated therein.

The instant discoveries indicate that unlike expression of PGC-1a, the expression of the PGC-1b isoform in C2C12 myotubes does not affect mitochondrial function, either directly or through an interference with PGC-1a However, PGC-1b induced the expression of several genes that regulate fatty acid uptake and utilization. The genes activated by PGC-1b in C2C12 cells are similar to the genes that are induced in skeletal muscle upon fasting, a condition known to shift muscle substrate utilization from glucose to fatty acids. Surprisingly, while some of these genes were induced by both PGC-1a and PGC-1b, lipoprotein lipase (LPL) and Acyl Co-A oxidase (AOX) were only induced by PGC-1b.

The-transcriptional co-activator PGC-1a plays a major role in regulating critical aspects of cellular metabolism. When expressed in muscle cells, PGC-1a stimulates mitochondrial biogenesis and simultaneously activates UCP-2, a mitochondrial membrane protein belonging to the uncoupling protein family (Wu, Z. et al. (1999) *Cell* 98(1): 115-24). In addition to stimulating the mitochondrial capacity in muscle cells, PGC-1a concurrently stimulates the expression of Glut4, resulting in increased glucose uptake (Michael, L. F. et al. (2001) *Proc. Natl. Acad. Sci. USA* 98(7):3820-5). Furthermore, PGC-1a was also shown to stimulate the expression in cardiomyocytes of MCAD and M-CPT-1, two regulatory factors of the mitochondrial beta oxidation pathway (Lehman, J. J. et al. (2000) *J. Clin. Invest.* 106(7):847-56).

The novel isoforms, PGC-1b and PGC-1c, provide novel targets for the regulation of cellular metabolism, including fatty acid metabolism. While both isoforms are excluded from the nucleus, PGC-1b, owing to its carboxy-terminal peroxisomal localization signal, is targeted to peroxisomes. In contrast to PGC-1a, PGC-1b lacks the ability to stimulate mitochondrial biogenesis and function in C2C12 myoblasts. However, this isoform specifically activates several critical genes involved in the uptake and utilization of fatty acids.

The rate of fatty acid oxidation in muscle is an important factor affecting whole-body metabolism. Altering this variable can have profound influence on pathologies such as obesity, diabetes and heart disease. This rate has been shown to be directly stimulated by several hormones, including thyroid and growth hormones, and more recently by adipsin, a protein secreted by the adipose tissue (Fruebis, J. et al. (2001) *Proc. Natl. Acad. Sci. USA* 98(4):2005-2010). In addition to these hormonal cues, the rate of fatty acid oxidation has also been shown to be regulated by the metabolic intermediate malonyl-CoA (Abu-Elheiga, L. et al. (2001) *Science* 291(5513):2613-6). Mice that were engineered to produce less malonyl-CoA in muscle (through disruption of the enzyme Acyl-CoA carboxylase (ACC)) had lower adiposity and exhibited an increased ability to oxidize fatty-acid in skeletal muscle as expected, but were also found to be hyperphagic, a phenotype that is strikingly similar to mice overexpressing the uncoupling protein UCP3 in muscle (Clapham, J. C. et al. (2000) *Nature* 406(6794): 415-8). PGC-1b activates malonyl CoA dehydrogenase (MCD), an enzyme whose action counters the effect of ACC, thereby promoting the flux of fatty acid through the beta oxidation pathway in mitochondria.

While increasing skeletal muscle fatty acid uptake by overexpressing LPL had a beneficial effect on adiposity in mice, it proved to be detrimental to muscle physiology if not accompanied by a parallel increase in fatty acid oxidation. Because PGC-1b appears to stimulate the whole program of fatty acid uptake and utilization, this molecule may represent a target for the development of anti-obesity drugs.

The term "family" when referring to the protein and nucleic acid molecules of the invention is intended to mean two or more proteins or nucleic acid molecules having a common structural domain or motif and having sufficient amino acid or nucleotide sequence homology as defined herein. Such family members can be naturally or non-naturally occurring and can be from either the same or different species. For example, a family can contain a first protein of human origin as well as other distinct proteins of human origin or alternatively, can contain homologues of non-human origin, e.g., rat or mouse proteins. Members of a family can also have common functional characteristics.

For example, the family of PGC-1 proteins, including the PGC-1 proteins of the present invention, include several domains and/or motifs. These domains/motifs include: a putative tyrosine phosphorylation site (at amino acid residues 204-212 of SEQ ID NO:7 and amino acid residues 204-212 of SEQ ID NO: 13), a putative cAMP phosphorylation site (at amino acid residues 238-241 of SEQ ID NO:7 and amino acid residues 238-241 of SEQ ID NO:13), an LXXLL motif (at amino acids 142-146 of SEQ ID NO:7 and amino acid residues 142-146 of SEQ ID NO:13) which mediates interaction with a nuclear receptor, and a peroxisomal localization signal (at amino acid residues 318-320 of SEQ ID NO:7). As used herein, a tyrosine phosphorylation site is an amino acid sequence which includes at least one tyrosine residue which can be phosphorylated by a tyrosine protein kinase. Typically, a tyrosine phosphorylation site is characterized by a lysine or an arginine about seven residues to the N-terminal side of the phosphorylated tyrosine. An acidic residue (asparagine or glutamine) is often found on either three or four residues to the N-terminal side of the tyrosine (Patschinsky, T. et al. (1982) *Proc. Natl. Acad. Sci. USA* 79:973-977); Hunter, T. (1982) *J. Biol. Chem.* 257: 4843-4848; Cooper, J. A. et al. (1984) *J. Biol. Chem.* 259:7835-7841). As used herein, a cAMP phosphorylation site is an amino acid sequence which includes a serine or threonine residue which can be phosphorylated by a cAMP-dependent protein kinase. Typically, the cAMP phosphorylation site is characterized by at least two consecutive basic residues to the N-terminal side of the serine or threonine (Fremisco, J. R. et al. (1980) *J. Biol. Chem.* 255:42404245; Glass, D. B. and Smith, S. B. (1983) *J. Biol. Chem.* 258:14797-14803; Glass, D. B. et al. (1986) *J. Biol. Chem.* 261:2987-2993). As used herein, an LXXLL motif refers to a motif wherein X can be any amino acid and which mediates an interaction between a nuclear receptor and a coactivator (Heery et al. (1997) *Nature* 397:733-736; Torchia et al. (1997) *Nature* 387:677-684). As used herein, a peroxisomal localization signal refers to a protein motif that, when present in a protein, is sufficient to direct localization of said protein to peroxisomes.

Isolated proteins of the present invention, preferably PGC-1 proteins, have an amino acid sequence sufficiently homologous to the amino acid sequence of SEQ ID NO:7, 10, 13, or 16, or are encoded by a nucleotide sequence sufficiently homologous to SEQ ID NO:6, 8, 9, 11, 12, 14, 15, or 17. As used herein, the term "sufficiently homologous" refers to a first amino acid or nucleotide sequence which contains a sufficient or minimum number of identical or equivalent (e.g., an amino acid residue which has a similar side chain) amino acid residues or nucleotides to a second amino acid or nucleotide sequence such that the first and second amino acid or nucleotide sequences share common structural domains or motifs and/or a common functional activity. For example, amino acid or nucleotide sequences which share common structural domains having at least 60%, 65%, 70%, 75%, 80%, 85%, 85%, 90%, 91%, 92%, 93%, 94%, 95%, 96%, 97%, 98%, 99%, 99.25%, 99.5%, 99.75% or more homology or identity across the amino acid sequences of the domains and contain at least one and preferably two structural domains or motifs, are defined herein as sufficiently homologous. Furthermore, amino acid or nucleotide sequences which share at least 60%, 65%, 70%, 75%, 80%, 85%, 85%, 90%, 91%, 92%, 93%, 94%, 95%, 96%, 97%, 98%, 99%, 99.25%, 99.5%, 99.75% or more homology or identity and share a common functional activity are defined herein as sufficiently homologous.

In a preferred embodiment, a PGC-1 protein includes at least one or more of the following domains or motifs: a tyrosine phosphorylation motif, a cAMP phosphorylation motif, an LXXLL motif, and/or a peroxisomal localization signal, and has an amino acid sequence at least about 60%, 65%, 70%, 75%, 80%, 85%, 85%, 90%, 91%, 92%, 93%, 94%, 95%, 96%, 97%, 98%, 99%, 99.25%, 99.5%, 99.75% or more homologous or identical to the amino acid sequence of SEQ ID NO: 7, 10, 13, or 16. In yet another preferred embodiment, a PGC-1 protein includes at least one or more of the following domains or motifs: a tyrosine phosphorylation motif, a cAMP phosphorylation motif, an LXXLL motif, and/or a peroxisomal localization signal, and is encoded by a nucleic acid molecule having a nucleotide sequence which hybridizes under stringent hybridization conditions to a complement of a nucleic acid molecule comprising the nucleotide sequence of SEQ ID NO: 6, 8, 9, 11, 12, 14, 15, or 17. In another preferred embodiment, a PGC-1 protein includes at least one or more of the following domains or motifs: a tyrosine phosphorylation motif, a cAMP phosphorylation motif, an LXXLL motif, and/or a peroxisomal localization signal, and has a PGC-1 activity.

As used interchangeably herein, a "PGC-1 activity", "biological activity of PGC-1" or "functional activity of PGC-1", includes an activity exerted or mediated by a PGC-1 protein, polypeptide or nucleic acid molecule when expressed in a cell or on a membrane, as determined in vivo or in vitro, according to standard techniques. In one embodiment, a PGC-1 activity is a direct activity, such as interaction with a PGC-1 target molecule. In another embodiment, a PGC-1 activity is an indirect activity mediated, for example, by interaction of a PGC-1 molecule with a PGC-1 target molecule or binding partner. As used herein, a "target molecule" or "binding partner" is a molecule with which a PGC-1 protein binds or interacts in nature, such that function of the target molecule or binding partner is modulated. In an exemplary embodiment, a PGC-1 target molecule or binding partner is a peroxisomal protein.

In a preferred embodiment, a PGC-1 activity is at least one of the following activities: (i) interaction with a PGC-1 target molecule; (ii) modulation of intracellular signaling; (iii) modulation of cellular metabolism; (iv) localization to peroxisomes; (v) modulation of the expression of genes involved in fatty acid uptake and/or oxidation (e.g., LPL, FAT/CD36, VLACS, AOX, MCAD, and/or MCD); (vi) modulation of fatty acid uptake and/or oxidation; (vii) modulation of energy homeostasis; and/or (viii) modulation of lipid homeostasis.

The nucleotide sequence of the isolated human PGC-1b cDNA and the predicted amino acid sequence encoded by the PGC-1b cDNA are shown in FIGS. 1 and 2, respectively, and in SEQ ID NOs: 6 and 7, respectively.

The human PGC-1b gene, which is approximately 1893 nucleotides in length, encodes a protein having a molecular weight of approximately 35.2 kD which is approximately 320 amino acid residues in length.

The nucleotide sequence of the isolated human PGC-1c cDNA and the predicted amino acid sequence encoded by the PGC-1 cDNA are shown in FIGS. 3 and 4, respectively, and in SEQ ID NOs :12 and 13, respectively.

The human PGC-1c gene, which is approximately 1744 nucleotides in length, encodes a protein having a molecular weight of approximately 33 kD which is approximately 300 amino acid residues in length.

Various aspects of the invention are described in further detail in the following subsections:

I. Isolated Nucleic Acid Molecules

One aspect of the invention pertains to isolated nucleic acid molecules that encode PGC-1 proteins or biologically active portions thereof, as well as nucleic acid fragments sufficient for use as hybridization probes to identity PGC-1-encoding nucleic acid molecules.(e.g., PGC-1 mRNA) and fragments for use as PCR primers for the amplification or mutation of PGC-1 nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

The term "isolated nucleic acid molecule" includes nucleic acid molecules which are separated from other nucleic acid molecules which are present in the natural source of the nucleic acid. For example, with regards to genomic DNA, the term "isolated" includes nucleic acid molecules which are separated from the chromosome with which the genomic DNA is naturally associated. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated PGC-1 nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

A nucleic acid molecule of the present invention, e.g., a nucleic acid molecule having the nucleotide sequence of SEQ ID NO: 6,8,9, 11, 12, 14, 15, or 17, or a portion thereof, can be isolated using standard molecular biology techniques and the sequence information provided herein. Using all or a portion of the nucleic acid sequence of SEQ ID NO: 6, 8, 9, 11, 12, 14, 15, or 17, as hybridization probes, PGC-1 nucleic acid molecules can be isolated using standard hybridization and cloning techniques (e.g., as described in Sambrook, J. et al., Molecular Cloning : A Laboratory Manual. 2nd ed., Cold Spring Harbor Laboratory, Cold Spring Harbor Laboratory Press, Cold Spring Harbor, N.Y., 1989).

Moreover, a nucleic acid molecule encompassing all or a portion of SEQ ID NO: 6, 8, 9, 11, 12, 14, 15, or 17, or the nucleotide sequence of the DNA insert of the plasmid deposited with ATCC as Accession Number or can be isolated by the polymerase chain reaction (PCR) using synthetic oligonucleotide primers designed based upon the sequence of SEQ ID NO: 6, 8, 9, 11, 12, 14, 15, or 17.

A nucleic acid of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to PGC-1 nucleotide sequences can be prepared by standard synthetic techniques, e.g., using an automated DNA synthesizer.

In one embodiment, an isolated nucleic acid molecule of the invention comprises the nucleotide sequence shown in SEQ ID NO:6, 8, 9, 11, 12, 14, 15, or 17. This cDNA may comprise sequences encoding the human PGC-1b protein (e.g., the "coding region", from nucleotides 90-1049), as well as 5' untranslated sequence (nucleotides 1-89) and 3' untranslated sequences (nucleotides 1050-1893) of SEQ ID NO:6. Alternatively, the nucleic acid molecule can comprise only the coding region of SEQ ID NO:6 (e.g., nucleotides 90-1049, corresponding to SEQ ID NO:8). Accordingly, in another embodiment, an isolated nucleic acid molecule of the invention comprises SEQ ID NO:8 and nucleotides 1-89 of SEQ ID NO:6. In yet another embodiment, the isolated nucleic acid molecule comprises SEQ ID NO:8 and nucleotides 1050-1893 of SEQ ID NO:6. In yet another embodiment, the nucleic acid molecule consists of the nucleotide sequence set forth as SEQ ID NO:6 or SEQ ID NO:8. In another embodiment, an isolated nucleic acid molecule of the invention comprises SEQ ID NO:8 and a stop codon (e.g., nucleotides 1050-1052 of SEQ ID NO:6).

In another embodiment, an isolated nucleic acid molecule of the invention comprises the "unique region" of the human PGC-1b gene (e.g., the "unique coding region", from nucleotides 963-1049, as well as 3' untranslated sequences (nucleotides 1050-1893) of SEQ ID NO:6), corresponding to SEQ ID NO:9. Alternatively, the nucleic acid molecule can comprise only the unique coding region of SEQ ID NO:6 (e.g., nucleotides 963-1049, corresponding to SEQ ID NO: 11). In another embodiment, the nucleic acid molecule consists of the nucleotide sequence set forth as SEQ ID NO:9 or SEQ ID NO:11. In another embodiment, an isolated nucleic acid molecule of the invention comprises SEQ ID NO:11 and a stop codon (e.g., nucleotides 1050-1052 of SEQ ID NO:6). In other embodiments, an isolated nucleic acid molecule of the invention comprises nucleotides 1-38 or nucleotides 1-89 of SEQ ID NO:6. In still other embodiments, an isolated nucleic acid molecule of the invention comprises nucleotides 1050-1893, nucleotides 963-1091, nucleotides 1092-1859, or nucleotides 1860-1893 of SEQ ID NO:6.

In another embodiment, the cDNA may comprise sequences encoding the human PGC-1c protein (e.g., the "coding region", from nucleotides 67-966), as well as 5' untranslated sequence (nucleotides 1-66) and 3' untranslated sequences (nucleotides 967-1744) of SEQ ID NO: 12. Alternatively, the nucleic acid molecule can comprise only the coding region of SEQ ID NO:12 (e.g., nucleotides 67-966, corresponding to SEQ ID NO:14). Accordingly, in another embodiment, an isolated nucleic acid molecule of the invention comprises SEQ ID NO:14 and nucleotides 1-66 of SEQ ID NO:12. In yet another embodiment, the isolated nucleic acid molecule comprises SEQ ID NO:14 and nucleotides 967-1744 of SEQ ID NO:12. In yet another embodiment, the nucleic acid molecule consists of the nucleotide sequence set forth as SEQ ID NO: 12 or SEQ ID NO:14. In another embodiment, an isolated nucleic acid molecule of the invention comprises SEQ ID NO:14 and a stop codon (e.g., nucleotides 967-969 of SEQ ID NO:12).

In another embodiment, an isolated nucleic acid molecule of the invention comprises the "unique region" of the human PGC-1c gene (e.g., the "unique coding region", from nucleotides 940-966, as well as 3' untranslated sequences (nucleotides 967-1744) of SEQ ID NO:12), corresponding to SEQ ID NO:15. Alternatively, the nucleic acid molecule can comprise only the unique coding region of SEQ ID NO:12 (e.g., nucleotides 940-966, corresponding to SEQ ID NO:17). In another embodiment, the nucleic acid molecule consists of the nucleotide sequence set forth as SEQ ID NO:15 or SEQ ID NO:17. In other embodiments, an isolated nucleic acid molecule of the invention comprises nucleotides 1-15 or nucleotides 1-66 of SEQ ID NO:12. In still other embodiments, an isolated nucleic acid molecule of the invention comprises nucleotides 940-1068, nucleotides 967-1744, nucleotides 967-1068, or nucleotides 1069-1744 of SEQ ID NO: 12.

In still another embodiment, an isolated nucleic acid molecule of the invention comprises a nucleic acid molecule which is a complement of the nucleotide sequence shown in SEQ ID NO: 6,8,9, 11, 12, 14, 15, or 17, or a portion of any of these nucleotide sequences. A nucleic acid molecule which is complementary to the nucleotide sequence shown in SEQ ID NO: 6, 8,9, 11, 12, 14, 15, or 17, is one which is sufficiently complementary to the nucleotide sequence shown in SEQ ID NO : 6, 8, 9, 11, 12, 14, 15, or 17, such that it can hybridize to the nucleotide sequence shown in SEQ ID NO : 6, 8, 9, 11, 12, 14, 15, or 17, thereby forming a stable duplex.

In still another embodiment, an isolated nucleic acid molecule of the present invention comprises a nucleotide sequence which is at least about 60%, 65%, 70%, 75%, 80%, 85%, 85%, 90%, 91%, 92%, 93%, 94%, 95%, 96%,97%, 98%, 99%, 99.25%, 99.5%, 99.75%, 99.5%, 99.75% or more identical to the nucleotide sequence shown in SEQ ID NO: 6, 8, 9,11, 12, 14, 15, or 17 (e. g., to the entire length of the nucleotide sequence), or a portion or complement of any of these nucleotide sequences. In one embodiment, a nucleic acid molecule of the present invention comprises a nucleotide sequence which is at least (or no greater than) 25, 26, 27, 28, 30, 30, 36, 38, 40, 50, 59, 61, 87, 100, 150, 200, 250, 300, 350, 400, 450, 500, 550, 600, 650, 700, 704, 750, 800, 843, 850, 873, 874, 875, 876, 877, 900, 904, 905, 906, 906, 907, 908, 909, 910, 911, 924, 925, 926, 927, 932, 933, 934, 939, 940, 941, 947, 948, 949, 950, 1000, 1150, 1200, 1250, 1300, 1350, 1400, 1450, 1500, 1550, 1600, 1650, 1700, 1750, 1800, 1850 or more nucleotides in length and hybridizes under stringent hybridization conditions to a complement of a nucleic acid molecule of SEQ ID NO: 6, 8, 9, 11, 12, 14, 15, or 17. In another embodiment, a nucleic acid molecule of the present invention comprises a fragment of at least 30 nucleotides, e.g., 30 contiguous nucleotides, of a nucleic acid molecule comprising the nucleotide sequence of SEQ ID NO : 6 and includes at least nucleotide 964 of SEQ ID NO : 6. In another embodiment, a nucleic acid molecule of the present invention comprises a fragment of at least 30 nucleotides, e.g., 30 contiguous nucleotides, of a nucleic acid molecule comprising the nucleotide sequence of SEQ ID NO:12 and includes at least nucleotide 942 of SEQ ID NO:12.

Moreover, the nucleic acid molecule of the invention can comprise only a portion of the nucleic acid sequence of SEQ ID NO: 6,8,9, 11, 12, 14, 15, or 17, for example, a fragment which can be used as a probe or primer or a fragment encoding a portion of a PGC-1 protein, e.g., a biologically active portion of a PGC-1 protein. The nucleotide sequence determined from the cloning of the PGC-1 gene allows for the generation of probes and primers designed for use in identifying and/or cloning other PGC-1 family members, as well as PGC-1 homologues from other species. The probe/primer (e.g., oligonucleotide) typically comprises substantially purified oligonucleotide. The oligonucleotide typically comprises a region of nucleotide sequence that hybridizes under stringent conditions to at least about 12 or 15, preferably about 20 or 25, more preferably about 30, 35, 40, 45, 50, 55, 60, 65, or 75 consecutive nucleotides of a sense sequence of SEQ ID NO: 6, 8, 9, 11, 12, 14, 15, or 17, of an anti-sense sequence of SEQ ID NO: 6, 8, 9, 11, 12, 14, 15, or 17, or of a naturally occurring allelic variant or mutant of SEQ ID NO: 6, 8, 9, 11, 12, 14, 15, or 17.

Exemplary probes or primers are at least (or no greater than) 12 or 15, 20 or 25, 30, 35, 40, 45, 50, 55, 60, 65, 70, 75 or more nucleotides in length and/or comprise consecutive nucleotides of an isolated nucleic acid molecule described herein. Also included within the scope of the present invention are probes or primers comprising contiguous or consecutive nucleotides of an isolated nucleic acid molecule described herein, but for the difference of 1, 2, 3, 4, 5, 6, 7, 8, 9 or 10 bases within the probe or primer sequence. Probes based on the PGC-1 nucleotide sequences can be used to detect (e.g., specifically detect) transcripts or genomic sequences encoding the same or homologous proteins. In preferred embodiments, the probe further comprises a label group attached thereto, e.g. the label group can be a radioisotope, a fluorescent compound, an enzyme, or an enzyme co-factor. In another embodiment a set of primers is provided, e.g., primers suitable for use in a PCR, which can be used to amplify a selected region of a PGC-1 sequence, e.g., a domain, region, site or other sequence described herein. The primers should be at least 5, 10, or 50 base pairs in length and less than 100, or less than 200, base pairs in length. The primers should be identical, or differ by no greater than 1, 2, 3, 4, 5, 6, 7, 8, 9 or 10 bases when compared to a sequence disclosed herein or to the sequence of a naturally occurring variant. Such probes can be used as a part of a diagnostic test kit for identifying cells or tissue which misexpress a PGC-1 protein, such as by measuring a level of a PGC-1-encoding nucleic acid in a sample of cells from a subject, e.g., detecting PGC-1 mRNA levels or determining whether a genomic PGC-1 gene has been mutated or deleted.

A nucleic acid fragment encoding a "biologically active portion of a PGC-1 protein" can be prepared by isolating a portion of the nucleotide sequence of SEQ ID NO: 6, 8, 9, 11, 12, 14, 15, or 17, which encodes a polypeptide having a PGC-1 biological activity (the biological activities of the PGC-1 proteins are described herein), expressing the encoded portion of the PGC-1 protein (e. g., by recombinant expression in vitro) and assessing the activity of the encoded portion of the PGC-1 protein. In an exemplary embodiment, the nucleic acid molecule is at least 25, 26, 27, 28, 30, 30, 36, 38, 40, 50, 59, 61, 87,100, 150, 200, 250, 300, 350, 400, 450, 500, 550, 600, 650, 700, 704, 750, 800, 843, 850, 873,874, 875, 876, 877, 900, 904, 905, 906, 906, 907, 908, 909, 910, 911,924, 925, 926, 927, 932, 933, 934, 939, 940, 941, 947, 948, 949, 950, 1000, 1150, 1200, 1250, 1300, 1350,1400, 1450, 1500, 1550, 1600, 1650, 1700, 1750, 1800, 1850 or more nucleotides in length and encodes a protein having a PGC-1 activity (as described herein).

In another embodiment, the nucleic acid molecule encodes a fragment of a polypeptide comprising the amino acid sequence of SEQ ID NO:10, wherein the fragment comprises at least 10-15, 15-20, 20-25, 25-28 or more contiguous amino acid residues of the amino acid sequence of SEQ ID NO:10. In another embodiment, the nucleic acid molecule encodes a fragment of a polypeptide comprising the amino acid sequence of SEQ ID NO:7 or 13, wherein the fragment comprises at least 9, 10, 15, 20, 25, 29, 30, 31, 35, 40, 45, 50, 75, 100, 125, 150, 175, 200, 225, 250, 275, 291, 292, 293, 294, 295, 300 or more contiguous amino acid residues of SEQ ID NO:7 or 13. In yet another embodiment, the nucleic acid molecule encodes a fragment of a polypeptide comprising the amino acid sequence of SEQ ID NO:7, wherein the fragment comprises at least 9, 10, 15, 20, 25, 29, 30, 31, 35, 40, 45, 50, 75, 100, 125, 150, 175, 200, 225, 250, 275, 292, 293, 294, 295, 300 or more contiguous amino acid residues of SEQ ID NO:7 and includes at least residue 292 of SEQ ID NO:7. In still another embodiment, the nucleic acid molecule encodes a fragment of a polypeptide comprising the amino acid sequence of SEQ ID NO:13, wherein the fragment comprises at least 9, 10, 15, 20, 25, 29, 30, 31, 35, 40, 45, 50, 75, 100, 125, 150, 175, 200, 225, 250, 275, 292, 293, 294, 295 or more contiguous amino acid residues of SEQ ID NO:13 and includes at least residue 293 of SEQ ID NO:13.

The invention further encompasses nucleic acid molecules that differ from the nucleotide sequence shown in SEQ ID NO: 6, 8,9,11, 12,14, 15, or 17, due to degeneracy of the genetic code and thus encode the same PGC-1 proteins as those encoded by the nucleotide sequence shown in SEQ ID NO: 6, 8, 9, 11, 12, 14, 15, or 17, or the nucleotide sequence of the DNA insert of the plasmid deposited with ATCC as Accession Number or. In another embodiment, an isolated nucleic acid molecule of the invention has a nucleotide sequence encoding a protein having an amino acid sequence which differs by at least 1, but no greater than 5, 10, 20, 50 or 100 amino acid residues from the amino acid sequence shown in SEQ ID NO: 7, 10, 13, or 16. In yet another embodiment, the nucleic acid molecule encodes the amino acid sequence of human PGC-1. If an alignment is needed for this comparison, the sequences should be aligned for maximum homology.

Nucleic acid variants can be naturally occurring such as allelic variants (same locus), homologues (different locus), and orthologues (different organism) or can be non naturally occurring. Non-naturally occurring variants can be made by mutagenesis techniques, including those applied to polynucleotides, cells, or organisms. The variants can contain nucleotide substitutions, deletions, inversions and insertions. Variation can occur in either or both the coding and non-coding regions. The variations can produce both conservative and non-conservative amino acid substitutions (as compared in the encoded product).

Allelic variants result, for example, from DNA sequence polymorphisms within a population (e.g., the human population) that lead to changes in the amino acid sequences of the PGC-1 proteins. Such genetic polymorphism in the PGC-1 genes may exist among individuals within a population due to natural allelic variation. As used herein, the terms "gene" and "recombinant gene" refer to nucleic acid molecules which include an open reading frame encoding a PGC-1 protein, preferably a mammalian PGC-1 protein, and can further include non-coding regulatory sequences, and introns.

Accordingly, in one embodiment, the invention features isolated nucleic acid molecules which encode a naturally occurring allelic variant of a polypeptide comprising the amino acid sequence of SEQ ID NO: 7, 10, 13, or 16, wherein the nucleic acid molecule hybridizes to a complement of a nucleic acid molecule comprising SEQ ID NO: 6, 8, 9, 11, 12, 14, 15, or 17, for example, under stringent hybridization conditions.

Allelic variants of PGC-1, e.g., human PGC-1, include both functional and non-functional PGC-1 proteins. Functional allelic variants are naturally occurring amino acid sequence variants of the PGC-1 protein that maintain the ability to, e.g., modulate expression of genes involved in fatty acid uptake and/or oxidation. Functional allelic variants will typically contain only conservative substitution of one or more amino acids of SEQ ID NO:7, 10, 13, or 16, or substitution, deletion or insertion of noncritical residues in non-critical regions of the protein.

Non-functional allelic variants are naturally occurring amino acid sequence variants of the PGC-1 protein, e.g., human PGC-1, that do not have the ability to, e.g., modulate expression of genes involved in fatty acid uptake and/or oxidation. Non-functional allelic variants will typically contain a non-conservative substitution, a deletion, or insertion, or premature truncation of the amino acid sequence of SEQ ID NO:7, 10, 13, or 16, or a substitution, insertion, or deletion in critical residues or critical regions of the protein.

The present invention further provides non-human orthologues (e.g., non-human orthologues of the human PGC-1 protein). Orthologues of the human PGC-1 protein are proteins that are isolated from non-human organisms and possess the same fatty acid uptake and/or oxidation modulating activities as human PGC-1. Orthologues of the human PGC-1 protein can readily be identified as comprising an amino acid sequence that is substantially homologous to SEQ ID NO:7, 10, 13, or 16.

Moreover, nucleic acid molecules encoding other PGC-1 family members and, thus, which have a nucleotide sequence which differs from the PGC-1 sequences of SEQ ID NO: 6, 8, 9, 11, 12, 14, 15, or 17, are intended to be within the scope of the invention. For example, another PGC-1 cDNA can be identified based on the nucleotide sequence of human PGC-1. Moreover, nucleic acid molecules encoding PGC-1 proteins from different species, and which, thus, have a nucleotide sequence which differs from the PGC-1 sequences of SEQ ID NO: 6, 8, 9, 11, 12, 14, 15, or 17, or the nucleotide sequence of the DNA insert of the plasmid deposited with ATCC as Accession Number or are intended to be within the scope of the invention. For example, a mouse or monkey PGC-1 cDNA can be identified based on the nucleotide sequence of a human PGC-1.

Nucleic acid molecules corresponding to natural allelic variants and homologues of the PGC-1 cDNAs of the invention can be isolated based on their homology to the PGC-1 nucleic acids disclosed herein using the cDNAs disclosed herein, or a portion thereof, as a hybridization probe according to standard hybridization techniques under stringent hybridization conditions. Nucleic acid molecules corresponding to natural allelic variants and homologues of the PGC-1 cDNAs of the invention can further be isolated by mapping to the same chromosome or locus as the PGC-1 gene.

Orthologues, homologues and allelic variants can be identified using methods known in the art (e.g., by hybridization to an isolated nucleic acid molecule of the present invention, for example, under stringent hybridization conditions). In one embodiment, an isolated nucleic acid molecule of the invention is at least 15, 20, 25, 30 or more nucleotides in length and hybridizes under stringent conditions to the nucleic acid molecule comprising the nucleotide sequence of SEQ ID NO:6, 8, 9, 11, 12, 14, 15, or 17. In other embodiment, the nucleic acid is at least 25, 26, 27, 28, 30, 30, 36, 38, 40, 50, 59, 61, 87, 100, 150, 200, 250, 300, 350, 400, 450, 500, 550, 600, 650, 700, 704, 750, 800, 843, 850, 873, 874, 875, 876, 877, 900, 904, 905, 906, 906, 907, 908, 909, 910, 911, 924, 925, 926, 927, 932, 933, 934, 939, 940, 941, 947, 948, 949, 950, 1000, 1150, 1200, 1250, 1300, 1350, 1400, 1450, 1500, 1550, 1600, 1650, 1700, 1750, 1800, 1850 or more nucleotides in length.

As used herein, the term "hybridizes under stringent conditions" is intended to describe conditions for hybridization and washing under which nucleotide sequences that are significantly identical or homologous to each other remain hybridized to each other. Preferably, the conditions are such that sequences at least about 70%, more preferably at least about 80%, even more preferably at least about 85% or 90% identical to each other remain hybridized to each other. Such stringent conditions are known to those skilled in the art and can be found in *Current Protocols in Molecular Biology*, Ausubel et al., eds., John Wiley & Sons, Inc. (1995), sections 2, 4 and 6. Additional stringent conditions can be found in *Molecular Cloning: A Laboratory Manual*, Sambrook et al., Cold. Spring Harbor Press, Cold Spring Harbor, N.Y. (1989), chapters 7, 9 and 11. A preferred, non-limiting example of stringent hybridization conditions includes hybridization in 4× or 6× sodium chloride/sodium citrate (SSC), at about 65-70° C. (or hybridization in 4×SSC plus 50% formamide at about 42-50° C.) followed by one or more washes in 1×SSC, at about 65-70° C. A further preferred, non-limiting example of stringent hybridization conditions includes hybridization at 6×SSC at 45° C., followed by one or more washes in 0.2×SSC, 0.1% SDS at 65° C. A preferred, non-limiting example of highly stringent hybridization conditions includes hybridization in 1×SSC, at about 65-70° C. (or hybridization in 1×SSC plus 50% formamide at about 42-50° C.) followed by one or more washes in 0.3×SSC, at about 65-70° C. A preferred, non-limiting example of reduced stringency hybridization conditions includes hybridization in 4× or 6×SSC, at about 50-60° C. (or alternatively hybridization in 6×SSC plus 50% formamide at about 40-45° C.) followed by one or more washes in 2×SSC, at about 50-60° C. Ranges intermediate to the above-recited values, e.g., at 65-70° C. or at 42-50° C. are also intended to be encompassed by the present invention. SSPE (1×SSPE is 0.15 M NaCl, 10 mM $NaH_2PO_4$, and 1.25 mM EDTA, pH 7.4) can be substituted for SSC (1×SSC is 0.15 M NaCl and 15 mM sodium citrate) in the hybridization and wash buffers; washes are performed for 15 minutes each after hybridization is complete. The hybridization temperature for hybrids anticipated to be less than 50 base pairs in length should be 5-10° C. less than the melting temperature ($T_m$) of the hybrid, where $T_m$ is determined according to the following equations. For hybrids less than 18 base pairs in length, $T_m(° C.) = 2(\# \text{ of A+T bases}) + 4(\# \text{ of G+C bases})$. For hybrids between 18 and 49 base pairs in length, $T_m(° C.) = 81.5 + 16.6(\log_{10}[Na^+]) + 0.41(\% \text{ G+C}) - (600/N)$, where N is the number of bases in the hybrid, and $[Na^+]$ is the concentration of sodium ions in the hybridization buffer ($[Na^+]$ for 1×SSC=0.165 M). It will also be recognized by the skilled practitioner that additional reagents may be added to hybridization and/or wash buffers to decrease non-specific hybridization of nucleic acid molecules to membranes, for example, nitrocellulose or nylon membranes, including but not limited to blocking agents (e.g., BSA or salmon or herring sperm carrier DNA), detergents (e.g., SDS), chelating agents (e.g., EDTA), Ficoll, PVP and the like. When using nylon membranes, in particular, an additional preferred, non-limiting example of stringent hybridization conditions is hybridization in 0.25-0.5M $NaH_2PO_4$, 7% SDS at about 65° C., followed by one or more washes at 0.02M $NaH_2PO_4$, 1% SDS at 65° C., see e.g., Church and Gilbert (1984) *Proc. Natl. Acad. Sci. USA* 81:1991-1995 (or alternatively 0.2×SSC, 1% SDS).

Preferably, an isolated nucleic acid molecule of the invention that hybridizes under stringent conditions to the sequence of SEQ ID NO:6, 8, 9, 11, 12, 14, 15, or 17 corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

In addition to naturally-occurring allelic variants of the PGC-1 sequences that may exist in the population, the skilled artisan will further appreciate that changes can be introduced by mutation into the nucleotide sequences of SEQ ID NO: 6, 8, 9, 11, 12, 14, 15, or 17, thereby leading to changes in the amino acid sequence of the encoded PGC-1 proteins, without altering the functional ability of the PGC-1 proteins. For example, nucleotide substitutions leading to amino acid substitutions at "non-essential" amino acid residues can be made in the sequence of SEQ ID NO: 6, 8, 9, 11, 12, 14, 15, or 17. A "nonessential" amino acid residue is a residue that can be altered from the wild-type sequence of PGC-1 (e.g., the sequence of SEQ ID NO: 7, 10, 13, or 16) without altering the biological activity, whereas an "essential" amino acid residue is required for biological activity. For example, amino acid residues that are conserved among the PGC-1 proteins of the present invention, e.g., those present in a peroxisomal localization signal, are predicted to be particularly unamenable to alteration. Furthermore, additional amino acid residues that are conserved between the PGC-1 proteins of the present invention and other members of the PGC-1 family are not likely to be amenable to alteration.

Accordingly, another aspect of the invention pertains to nucleic acid molecules encoding PGC-1 proteins that contain changes in amino acid residues that are not essential for activity. Such PGC-1 proteins differ in amino acid sequence from SEQ ID NO:7, 10, 13, or 16, yet retain biological activity. In one embodiment, the isolated nucleic acid molecule comprises a nucleotide sequence encoding a protein, wherein the protein comprises an amino acid sequence at least about 60%, 65%, 70%, 75%, 80%, 85%, 85%, 90%, 91%, 92%, 93%, 94%, 95%, 96%, 97%, 98%, 99%, 99.25%, 99.5%, 99.75% or more homologous to SEQ ID NO:7, 10, 13, or 16, e.g., to the entire length of SEQ ID NO:7, 10, 13, or 16.

An isolated nucleic acid molecule encoding a PGC-1 protein homologous to the protein of SEQ ID NO: 7, 10, 13, or 16 can be created by introducing one or more nucleotide substitutions, additions or deletions into the nucleotide sequence of SEQ ID NO: 6, 8, 9, 11, 12, 14, 15, or 17, such that one or more amino acid substitutions, additions or deletions are introduced into the encoded protein. Mutations can be introduced into SEQ ID NO: 6, 8, 9, 11, 12, 14, 15, or 17, by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e. g., lysine, arginine, histidine), acidic side chains (e.g., aspartic acid, glutamic acid), uncharged polar side chains (e. g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, a predicted nonessential amino acid residue in a PGC-1 protein is preferably replaced with another amino acid residue from the same side chain family. Alternatively, in another embodiment, mutations can be introduced randomly along all or part of a PGC-1 coding sequence, such as by saturation mutagenesis, and the resultant mutants can be screened for PGC-1 biological activity to identify mutants that retain activity. Following mutagenesis of SEQ ID NO: 6, 8, 9, 11, 12, 14, 15, or 17, the encoded protein can be expressed recombinantly and the activity of the protein can be determined.

In a preferred embodiment, a mutant PGC-1 protein can be assayed for the ability to (i) interact with a PGC-1 target molecule; (ii) modulate intracellular signaling; (iii) modulate cellular metabolism; (iv) localize to peroxisomes; (v) modulate the expression of genes involved in fatty acid uptake and/or oxidation (e.g., LPL, FAT/CD36, VLACS, AOX, MCAD, and/or MCD); (vi) modulate fatty acid uptake and/or oxidation; (vii) modulate energy homeostasis; and/or (viii) modulate lipid homeostasis.

In addition to the nucleic acid molecules encoding PGC-1 proteins described above, another aspect of the invention pertains to isolated nucleic acid molecules which are antisense thereto. In an exemplary embodiment, the invention provides an isolated nucleic acid molecule which is antisense to a PGC-1 nucleic acid molecule (e.g., is antisense to the coding strand of a PGC-1 nucleic acid molecule). An "antisense" nucleic acid comprises a nucleotide sequence which is complementary to a "sense" nucleic acid encoding a protein, e.g., complementary to the coding-strand of a double-stranded cDNA molecule or complementary to an mRNA sequence. Accordingly, an antisense nucleic acid can hydrogen bond to a sense nucleic acid. The antisense nucleic acid can be complementary to an entire PGC-1 coding strand, or to only a portion thereof. In one embodiment, an antisense nucleic acid molecule is antisense to "coding region sequences" of the coding strand of a nucleotide sequence encoding PGC-1. The term "coding region sequences" refers to the region of the nucleotide sequence comprising codons which are translated into amino acid residues (e.g., the coding region sequences of human PGC-1b corresponding to SEQ ID NO:8, or the coding region sequences of human PGC-1c corresponding to SEQ ID NO: 14). In another embodiment, the antisense nucleic acid molecule is antisense to a "noncoding region" of the coding strand of a nucleotide sequence encoding PGC-1. The term "noncoding region" refers to 5' and/or 3' sequences which flank the coding region sequences that are not translated into amino acids (also referred to as 5' and 3' untranslated regions).

Given the coding strand sequences encoding PGC-1 disclosed herein (e.g., SEQ ID NO:8 or 14), antisense nucleic acids of the invention can be designed according to the rules of Watson and Crick base pairing. The antisense nucleic acid molecule can be complementary to coding region sequences of PGC-1 mRNA, but more preferably is an oligonucleotide which is antisense to only a portion of the PGC-1 mRNA. An antisense oligonucleotide can be, for example, about 5, 10, 15, 20, 25, 30, 35, 40, 45, 50, 55, 60, 65, 70, 75, 80, or more nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xantine, 4acetylcytosine, 5-(carboxyhydroxylmethyl)uracil, 5 carboxymethylaminomethyl-2-thiouridine, 5-carboxymethylaminomethyluracil, dihydrouracil, beta-D-galactosylqueosine, inosine, N6isopentenyladenine, 1-methylguanine, 1-methylinosine, 2,2-direthylguanine, 2-methyladenine, 2-methylguanine, 3-methylcytosine, 5-methylcytosine, N6adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a PGC-1 protein to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention include direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g. by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids Res.* 15:6625-6641). The antisense nucleic acid molecule can also comprise a 2'-o-methyltribonucleotide (Inoue et al. (1987) *Nucleic Acids Res.* 15:6131-6148) or a chimeric RNA-DNA analogue (Inoue et al. (1987) *FEBS Lett.* 215: 327-330).

In still another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. Thus, ribozymes (e. g., hammerhead ribozymes (described in Haseloff and Gerlach (1988) *Nature* 334: 585-591)) can be used to catalytically cleave PGC-1 mRNA transcripts to thereby inhibit translation of PGC-1 mRNA. A ribozyme having specificity for a PGC-1-encoding nucleic acid can be designed based upon the nucleotide sequence of a PGC-1 cDNA disclosed herein (i.e., SEQ ID NO: 6, 8, 9, 11, 12, 14, 15, or 17). For example, a derivative of a Tetrahynaena L-19 IVS RNA can be constructed in which the nucleotide sequence of the active site is complementary to the nucleotide sequence to be cleaved in a PGC-1-encoding mRNA. See, e. g., Cech et al., U. S. Pat. No. 4,987, 071; and Cech et al., U. S. Pat. No. 5,116, 742. Alternatively, PGC-1 mRNA can be used to select a catalytic RNA having a specific ribonuclease activity from a pool of RNA molecules. See, e.g., Bartel, D. and Szostak, J. W. (1993) *Science* 261: 1411-1418.

Alternatively, PGC-1 gene expression can be inhibited by targeting nucleotide sequences complementary to the regulatory region of the PGC-1 gene (e.g., the PGC-1b or PGC-1c promoters and/or enhancers; e.g., nucleotides 1-89 of SEQ ID NO:6 or nucleotides 1-66 of SEQ ID NO: 12) to form triple helical structures that prevent transcription of the PGC-1 gene in target cells. In another embodiment, the sequences unique to PGC-1b or PGC-1c can be targeted (e.g, SEQ ID NO:9 or SEQ ID NO:15). See generally, Helene, C. (1991) *Anticancer Drug Des.* 6(6):569-84; Helene, C. et al. 1992) *Ann. N.Y. Acad. Sci.* 660:27-36;and Maher, L. J.(1992) *Bioessays* 14(12):807-15.

In yet another embodiment, the PGC-1 nucleic acid molecules of the present invention can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup, B. and Nielsen, P. E. (1996) *Bioorg. Med Chem.* 4(1):5-23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup and Nielsen (1996) supra and Perry-O'Keefe et al. (1996) *Proc. Natl. Acad. Sci. USA* 93:14670-675.

PNAs of PGC-1 nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of PGC-1 nucleic acid molecules can also be used in the analysis of single base pair mutations in a gene (e.g., by PNA-directed PCR clamping); as 'artificial restriction enzymes' when used in combination with other enzymes (e.g., S1 nucleases (Hyrup and Nielsen (1996) supra)); or as probes or primers for DNA sequencing or hybridization (Hyrup and Nielsen (1996) supra; Perry-O'Keefe et al. (1996) supra).

In another embodiment, PNAs of PGC-1 can be modified (e.g.,.to enhance their stability or cellular uptake), by attaching lipophilic or other helper groups to PNA, by *the formation of PNA-DNA chimeras, or by the use of liposomes or other techniques of drug delivery known in the art. For example, PNA-DNA chimeras of PGC-1 nucleic acid molecules can be generated which may combine the advantageous properties of PNA and DNA. Such chimeras allow DNA recognition enzymes (e.g., RNase H and DNA polymerases) to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup and Nielsen (1996) supra). The synthesis of PNA-DNA chimeras can be performed as described in Hyrup and Nielsen (1996) supra and Finn, P. J. et al. (1996) *Nucleic Acids Res.* 24(17):3357-63. For example, a DNA chain can be synthesized on a solid support using standard phosphoramidite coupling chemistry and modified nucleoside analogs, e.g., 5'-(4 -methoxytrityl)amino-5'-deoxy-thymidine phosphoramidite, can be used as a between the PNA and the 5' end of DNA (Mag, M. et al. (1989) *Nucleic Acids Res.* 17:5973-88). PNA monomers are then coupled in a stepwise manner to produce a chimeric molecule with a 5' PNA segment and a 3' DNA segment (Finn et al. (1996) supra). Alternatively, chimeric molecules can be synthesized with a 5' DNA segment and a 3' PNA segment (Peterser, K. H. et al. (1975) *Bioorganic Med Chem. Lett.* 5:1119-11124).

In other embodiments, the oligonucleotide may include other appended groups such as peptides (e.g., for targeting host cell receptors in vivo), or agents facilitating transport across the cell membrane (see, e.g., Letsinger et al. (1989) *Proc. Natl. Acad Sci. USA* 86:6553-6556; Lemaitre et al. (1987) *Proc. Natl. Acad. Sci. USA* 84:648-652; PCT Publication No. WO 88/09810) or the blood-brain barrier (see, e.g., PCT Publication No. WO 89/10134). In addition, oligonucleotides can be modified with hybridization-triggered cleavage agents (See, e.g., Krol et al. (1988) *Biotechniques* 6:958-976) or intercalating agents (See, e.g., Zon (1988) *Pharm. Res.* 5:539-549). To this end, the oligonucleotide may be conjugated to another molecule (e.g., a peptide, hybridization triggered cross-linking agent, transport agent, or hybridization-triggered cleavage agent).

II. Isolated PGC-1 Proteins and Anti-PGC-1 Antibodies

One aspect of the invention pertains to isolated or recombinant PGC-1 proteins and polypeptides, and biologically active portions thereof, as well as polypeptide fragments suitable for use as immunogens to raise anti-PGC-1 antibodies. In one embodiment, native PGC-1 proteins can be isolated from cells or tissue sources by an appropriate purification scheme using standard protein purification techniques. In another embodiment, PGC-1 proteins are produced by recombinant DNA techniques. Alternative to recombinant expression, a PGC-1 protein or polypeptide can be synthesized chemically using standard peptide synthesis techniques.

An "isolated" or "purified" protein or biologically active portion thereof is substantially free of cellular material or other contaminating proteins from the cell or tissue source from which the PGC-1 protein is derived, or substantially free from chemical precursors or other chemicals when chemically synthesized. The language "substantially free of cellular material" includes preparations of PGC-1 protein in which the protein is separated from cellular components of the cells from which it is isolated or recombinantly produced. In one embodiment, the language "substantially free of cellular material" includes preparations of PGC-1 protein having less than about 30% (by dry weight) of non-PGC-1 protein (also referred to herein as a "contaminating protein"), more preferably less than about 20% of non-PGC-1 protein, still more preferably less than about 10% of non-PGC-1 protein, and most preferably less than about 5% non-PGC-1 protein. When the PGC-1 protein or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of PGC-1 protein in which the protein is separated from chemical precursors or other chemicals which are involved in the synthesis of the protein. In one embodiment, the language "substantially free of chemical precursors or other chemicals" includes preparations of PGC-1 protein having less than about 30% (by dry weight) of chemical precursors or non-PGC-1 chemicals, more preferably less than about 20% chemical precursors or non-PGC-1 chemicals, still more preferably less than about 10% chemical precursors or non-PGC-1 chemicals, and most preferably less than about 5% chemical precursors or non-PGC-1 chemicals.

As used herein, a "biologically active portion" of a PGC-1 protein includes a fragment of a PGC-1 protein which participates in an interaction between a PGC-1 molecule and a non-PGC-1 molecule or which is capable of modulating expression of genes involved in fatty acid uptake and/or oxidation. Biologically active portions of a PGC-1 protein include peptides comprising amino acid sequences sufficiently homologous to or derived from the PGC-1 amino acid sequences, e.g. the amino acid sequences shown in SEQ ID NO:7, 10, 13, or 16, which include sufficient amino acid residues to exhibit at least one activity of a PGC-1 protein.

Typically, biologically active portions comprise a domain or motif with at least one activity of the PGC-1 protein, e.g., modulation of the expression of genes involved in fatty acid uptake and/or oxidation. A biologically active portion of a PGC-1 protein can be a polypeptide which is, for example, 9, 10, 25, 28, 29, 30, 31, 35, 40, 45, 50, 75, 100, 125, 150, 175, 200, 225, 250, 291, 292, 293, 294, 295, 300 or more amino acids in length. Biologically active portions of a PGC-1 protein can be used as targets for developing agents which modulate a PGC-1 mediated activity, e.g., modulation of the expression of genes involved in fatty acid uptake and/or oxidation.

In one embodiment, a biologically active portion of a PGC-1 protein comprises at least one tyrosine phosphorylation motif, one cAMP phosphorylation motif, one LXXLL motif, and/or one peroxisomal localization signal. Moreover, other biologically active portions, in which other regions of the protein are deleted, can be prepared by recombinant techniques and evaluated for one or more of the functional activities of a native PGC-1 protein.

Another aspect of the invention features fragments of the protein having the amino acid sequence of SEQ ID NO: 7, 10, 13, or 16, for example, for use as immunogens. In one embodiment, a fragment comprises at least 8 amino acids (e.g., contiguous or consecutive amino acids) of the amino acid sequence of SEQ ID NO: 7, 10, 13, or 16. In another embodiment, a fragment comprises at least 8, 9, 10, 15, 20, 25, 28, 29, 30, 31, 35, 40, 45, 50, 75, 100, 125, 150, 175, 200, 225, 250, 275, 291, 292, 293, 294, 295, 300 or more amino acids (e.g., contiguous or consecutive amino acids) of the amino acid sequence of SEQ ID NO: 7, 10, 13, or 16.

In another embodiment, a fragment comprises at least 8, 9, 10, 15, 20, 25, 28, 29, 30, 31, 35, 40, 45, 50, 75, 100, 125, 150, 175, 200, 225, 250, 275, 291, 292, 293, 294, 295, 300 or more contiguous amino acid residues of SEQ ID NO:7 and includes at least residue 292 of SEQ ID NO:7. In still another embodiment, a fragment comprises at least 8, 9, 10, 15, 20, 25, 28, 29, 30, 31, 35, 40, 45, 50, 75, 100, 125, 150, 175, 200, 225, 250, 275, 291, 292, 293, 294, 295 or more contiguous amino acid residues of SEQ ID NO:13 and includes at least residue 293of SEQ ID NO:13.

In a preferred embodiment, a PGC-1 protein has an amino acid sequence shown in SEQ ID NO:7, 10, 13, or 16. In other embodiments, the PGC-1 protein is substantially identical to SEQ ID NO:7, 10, 13, or 16, and retains the functional activity of the protein of SEQ ID NO:7, 10, 13, or 16, yet differs in amino acid sequence due to natural allelic variation or mutagenesis, as described in detail in subsection I above. In another embodiment, the PGC-1 protein is a protein which comprises an amino acid sequence at least about 60%, 65%, 70%, 75%, 80%, 85%, 85%, 90%, 91%, 92%, 93% 94%, 95%, 96%, 97%, 98%, 99%, 99.25%, 99.5%, 99.75% or more identical to SEQ ID NO:7, 10, 13, or 16.

In another embodiment, the invention features a PGC-1 protein which is encoded by a nucleic acid molecule consisting of a nucleotide sequence at least about 60%, 65%, 70%, 75%, 80%, 85%, 85%, 90%, 91%, 92%, 93%, 94%, 95%, 96%, 97%, 98%, 99%, 99.25%, 99.5%, 99.75% or more identical to a nucleotide sequence of SEQ ID NO:6, 8, 12, 14, 15, or 17, or a complement thereof. This invention further features a PGC-1 protein which is encoded by a nucleic acid molecule consisting of a nucleotide sequence which hybridizes under stringent hybridization conditions to a complement of a nucleic acid molecule comprising the nucleotide sequence of SEQ ID NO:6, 8, 9, 11, 12, 14, 15, or 17, or a complement thereof.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%; preferably at least 40%, more preferably at least 50%, even more preferably at least 60%, and even more preferably at least 70%, 80%, or 90% of the length of the reference sequence (eg., when aligning a second sequence to the PGC-1b amino acid sequence of SEQ ID NO:7 having 320 amino acid residues, at least 96, preferably at least 128, more preferably at least 160, even more preferably at least .192, and even more preferably at least 224, 256 or 288 amino acid residues are aligned; when aligning a second sequence to the PGC-1c amino acid sequence of SEQ ID NO:13 having 300 amino acid residues at least 90 preferably at least 120, more preferably at least 150, even more preferably at least 180, and even more preferably at least 210, 240 or 270 amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (*J. Mol. Biol.* (48):444-453 (1970)) algorithm which has been incorporated into the GAP program in the GCG software package (available online through the Genetics Computer Group) using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at (available online through the Genetics Computer Group), using a NWSgapdna. CMP matrix and a gap weight of 40, 50, 60, 70, or 80 and a length weight of 1, 2, 3, 4, 5, or 6. A preferred, non-limiting example of parameters to be used in conjunction with the GAP program include a Blossum 62 scoring matrix with a gap penalty of 12, a gap extend penalty of 4, and a frame shift gap penalty of 5.

In another embodiment, the percent identity between two amino acid or nucleotide sequences is determined using the algorithm of Meyers and Miller (*Comput. Appl. Biosci.* 4:11-17 (1988)) which has been incorporated into the ALIGN program (version 2.0 or version 2.0U), using a PAM120 weight residue table, a gap length penalty of 12 and a gap penalty of 4.

The nucleic acid and protein sequences of the present invention can further be used as a "query sequence" to perform a search against public databases to, for example, identify other family members or related sequences. Such searches can be performed using the NBLAST and XBLAST programs (version 2.0) of Altschul et al. (1990) *J. Mol. Biol* 215:403-10. BLAST nucleotide searches can be performed with the NBLAST program, score=100, wordlength=12 to obtain nucleotide sequences homologous to PGC-1 nucleic acid molecules of the invention. BLAST protein searches can be performed with the XBLAST program, score=50, wordlength=3 to obtain amino acid sequences homologous to PGC-1 protein molecules of the invention. To obtain gapped alignments for comparison purposes, Gapped BLAST can be utilized as described in Altschul et al. (1997) *Nucleic Acids Res.* 25(17):3389-3402. When utilizing BLAST and Gapped BLAST programs, the default parameters of the respective programs (e.g., XBLAST and NBLAST can be used. See the website for the National Center for Biotechnology Information.

The invention also provides PGC-1 chimeric or fusion proteins. As used herein, a PGC-1 "chimeric protein" or "fusion protein" comprises a PGC-1 polypeptide operatively linked to a non-PGC-1 polypeptide. A "PGC-1 polypeptide" refers to a polypeptide having an amino acid sequence corresponding to PGC-1 (e.g., PGC-1 or PGC-1), whereas a "non-PGC-1 polypeptide" refers to a polypeptide having an amino acid sequence corresponding to a protein which is not substantially homologous to the PGC-1 protein, e.g., a protein which is different from the PGC-1 protein and which is derived from the same or a different organism Within a PGC-1 fusion protein the PGC-1 polypeptide can correspond to all or a portion of a PGC-1 protein. In a preferred embodiment, a PGC-1 fusion protein comprises at least one biologically active portion of a PGC-1 protein. In another preferred embodiment, a PGC-1 fusion protein comprises at least two biologically active portions of a PGC-1 protein. Within the fusion protein, the term "operatively linked" is intended to indicate that the PGC-1 polypeptide and the non-PGC-1 polypeptide are fused in frame to each other. The non-PGC-1 polypeptide can be fused to the N-terminus or C-terminus of the PGC-1 polypeptide.

For example, in one embodiment, the fusion protein is a GST-PGC-1 fusion protein in which the PGC-1 sequences are fused to the C-terminus of the GST sequences. Such fusion proteins can facilitate the purification of recombinant PGC-1. In another embodiment, the fusion protein is a PGC-1 protein containing a heterologous signal sequence at its N-terminus. In certain host cells (e.g., mammalian host cells), expression and/or secretion of PGC-1 can be increased through use of a heterologous signal sequence. In another embodiment the fusion protein is a GFP-PGC-1 fusion protein in which the PGC-1 sequences are fused to the green fluorescent protein (GFP), which allows visualization of the PGC-1 fusion protein in live cells.

The PGC-1 fusion proteins of the invention can be incorporated into pharmaceutical compositions and administered to a subject in vivo. The PGC-1 fusion proteins can be used to affect the bioavailability of a PGC-1 target molecule. Use of PGC-1 fusion proteins may be useful therapeutically for the treatment of disorders caused by, for example, (i) aberrant modification or mutation of a gene encoding a PGC-1 protein; (ii) mis-regulation of the PGC-1 gene; and (iii) aberrant post-translational modification of a PGC-1 protein.

Moreover, the PGC-1-fusion proteins of the invention can be used as immunogens to produce anti-PGC-1 antibodies in a subject, to purify PGC-1 target molecules, and in screening assays to identify molecules which inhibit or enhance the transport of a PGC-1 substrate or the interaction of PGC-1 with a PGC-1 target molecule.

Preferably, a PGC-1 chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992). Moreover, many expression vectors are commercially available that already encode a fusion moiety (e.g., a GST or GFP polypeptide). A PGC-1-encoding nucleic acid can be cloned into such an expression vector such that the fusion moiety is linked in-frame to the PGC-1 protein.

The present invention also pertains to variants of the PGC-1 proteins which function as either PGC-1 agonists (mimetics) or as PGC-1 antagonists. Variants of the PGC-1 proteins can be generated by mutagenesis, e.g., discrete point mutation or truncation of a PGC-1 protein. An agonist of the PGC-1 proteins can retain substantially the same, or a subset, of the biological activities of the naturally occurring form of a PGC-1 protein. An antagonist of a PGC-1 protein can inhibit one or more of the activities of the naturally occurring form of the PGC-1 protein by, for example, competitively modulating a PGC-1-mediated activity of a PGC-1 protein. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring form of the PGC-1 protein.

In one embodiment, variants of a PGC-1 protein which function as either PGC-1 agonists (mimetics) or as PGC-1 antagonists can be identified by screening combinatorial libraries of mutants, e.g., truncation mutants, of a PGC-1 protein for PGC-1 protein agonist or antagonist activity. In one embodiment, a variegated library of PGC-1 variants is generated by combinatorial mutagenesis at the nucleic acid level and is encoded by a variegated gene library. A variegated library of PGC-1 variants can be produced by, for example, enzymatically ligating a mixture of synthetic oligonucleotides into gene sequences such that a degenerate set of potential PGC-1 sequences is expressible as individual polypeptides, or alternatively, as a set of larger fusion proteins (e.g., for phage display) containing the set of PGC-1-sequences therein. There are a variety of methods which can be used to produce libraries of potential PGC-1 variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential PGC-1 sequences. Methods for synthesizing degenerate oligonucleotides are known in the art (see, e.g.,.Narang, S. A. (1983) *Tetrahedron* 39:3; Itakura et al. (1984) *Annu. Rev. Biochem.* 53:323; Itakura et al. (1984) *Science* 198:1056; Ike et al. (1983) *Nucleic. Acids Res.* 11:477).

In addition, libraries of fragments of a PGC-1 protein coding sequence can be used to generate a variegated population of PGC-1 fragments for screening and subsequent selection of variants of a PGC-1 protein. In one embodiment, a library of coding sequence fragments can be generated by treating a double stranded PCR fragment of a PGC-1 coding sequence with a nuclease under conditions wherein nicking occurs only about once per molecule, denaturing the double stranded DNA, renaturing the DNA to form double stranded DNA which can include sense/antisense pairs from different nicked products removing single stranded portions from reformed duplexes by treatment with S1 nuclease, and ligating the resulting fragment library into an expression vector. By this method, an expression library can be derived which encodes N-terminal, C-terminal and internal fragments of various sizes of the PGC-1 protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of PGC-1 proteins. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique which enhances the frequency of functional mutants in the libraries, can be used in combination with the screening assays to identify PGC-1 variants (Arkin and Youvan (1992) *Proc. Natl. Acad. Sci. USA* 89:7811-7815; Delagrave et al. (1993) *Protein Eng.* 6(3): 327-331).

In one embodiment, cell based assays can be exploited to analyze a variegated PGC-1 library. For example, a library of expression vectors can be transfected into a cell line which ordinarily responds to PGC-1 in a particular PGC-1 dependent manner. The transfected cells are then contacted with PGC-1 and the effect of the expression of the mutant on signaling by the PGC-1 can be detected, e.g, by measuring expression of genes involved in fatty acid uptake and/or oxidation. Plasmid DNA can then be recovered from the cells which score for inhibition, or alternatively, potentiation of signaling by the PGC-1 mutant, and the individual clones further characterized.

An isolated PGC-1 protein, or a portion or fragment thereof, can be used as an immunogen to generate antibodies that bind PGC-1 using standard techniques for polyclonal and monoclonal antibody preparation. A full-length PGC-1 protein can be used or, alternatively, the invention provides antigenic peptide fragments of PGC-1 for use as immunogens. The antigenic peptide of PGC-1 comprises at least 8 amino acid residues of the amino acid sequence shown in SEQ ID NO:7, 10, 13, or 16 and encompasses an epitope of PGC-1 such that an antibody raised against the peptide forms a specific immune complex with PGC-1. Preferably, the antigenic peptide comprises at least 10 amino acid residues, more preferably at least 15 amino acid residues, even more preferably at least 20 amino acid residues, and most preferably at least 30 amino acid residues. In another preferred embodiment, the antigenic peptide comprises an amino acid sequence unique to PGC-1b or PGC-1c, for example, a peptide comprising at least 8 amino acid residues of the amino acid sequence shown in SEQ ID NO:10 or 16.

Preferred epitopes encompassed by the antigenic peptide are regions of PGC-1 that are located on the surface of the protein, e.g., hydrophilic regions, as well as regions with high antigenicity.

A PGC-1 immunogen typically is used to prepare antibodies by immunizing a suitable subject (e.g., rabbit, goat, mouse, or other mammal) with the immunogen. An appropriate immunogenic preparation can contain, for example, recombinantly expressed PGC-1 protein or a chemically-synthesized PGC-1 polypeptide. The preparation can further include an adjuvant, such as Freund's complete or incomplete adjuvant, or similar immunostimulatory agent Immunization of a suitable subject with an immunogenic PGC-1 preparation induces a polyclonal anti-PGC-1 antibody response.

Accordingly, another aspect of the invention pertains to anti-PGC-1 antibodies. The term "antibody" as used herein refers to immunoglobulin molecules and immunologically active portions of immunoglobulin molecules, i.e., molecules that contain an antigen binding site which specifically binds (immunoreacts with) an antigen, such as PGC-1. Examples of immunologically active portions of immunoglobulin molecules include F(ab) and F(ab')₂ fragments which can be generated by treating the antibody with an enzyme such as pepsin. The invention provides polyclonal and monoclonal antibodies that bind PGC-1. The term "monoclonal antibody" or "monoclonal antibody composition", as used herein, refers to a population of antibody molecules that contain only one species of an antigen binding site capable of immunoreacting with a particular epitope of PGC-1. A monoclonal antibody composition thus typically displays a single binding affinity for a particular PGC-1 protein with which it immunoreacts.

Polyclonal anti-PGC-1 antibodies can be prepared as described above by immunizing a suitable subject with a PGC-1 immunogen. The anti-PGC-1 antibody titer in the immunized subject can be monitored over time by standard techniques, such as with an enzyme linked immunosorbent assay (ELISA) using immobilized PGC-1. If desired, the antibody molecules directed against PGC-1 can be isolated from the mammal (e.g., from the blood) and further purified by well known techniques, such as protein A chromatography to obtain the IgG fraction. At an appropriate time after immunization, e.g., when the anti-PGC-1 antibody titers are highest, antibody-producing cells can be obtained from the subject and used to prepare monoclonal antibodies by standard techniques, such as the hybridoma technique originally described by Kohler and Mulstein (1975) *Nature* 256:495-497 (see also Brown et al. (1981) *J. Immunol.* 127:539-46; Brown et al. (1980) *J. Biol. Chem.* 255:4980-83; Yeh et al. (1976) *Proc. Natl. Acad. Sci. USA* 76:2927-31; and Yeh et al. (1982) *Int. J. Cancer* 29:269-75), the more recent human B cell hybridoma technique (Kozbor et al. (1983) *Immunol. Today* 4:72), the EBV-hybridoma technique (Cole et al. (1985), *Monoclonal Antibodies and Cancer Therapy*, Alan R Liss, Inc., pp. 77-96) or trioma techniques. The technology for producing monoclonal antibody hybridomas is well known (see generally Kenneth, R H. in *Monoclonal Antibodies: A New Dimension In Biological Analyses*, Plenum Publishing Corp., New York, N.Y. (1980); Lerner, E. A. (1981) *Yale J. Biol. Med* 54:387402; Gefter, M. L. et al. (1977) *Somatic Cell Genet.* 3:231-36). Briefly, an immortal cell line (typically a myeloma) is fused to lymphocytes (typically splenocytes) from a mammal immunized with a PGC-1 immunogen as described above, and the culture supernatants of the resulting hybridoma cells are screened to identify a hybridoma producing a monoclonal antibody that binds PGC-1.

Any of the many well known protocols used for fusing lymphocytes and immortalized cell lines can be applied for the purpose of generating an anti-PGC-1 monoclonal antibody (see, e.g., Galfre, G. et al. (1977) *Nature* 266:55052; Gefter et al. (1997) supra; Lerner (1981) supra; Kenneth (1980) supra). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind PGC-1, e.g., using a standard ELISA assay.

Alternative to preparing monoclonal antibody-secreting hybridomas, a monoclonal anti-PGC-1 antibody can be identified and isolated by screening a recombinant combinatorial immunoglobulin library (e.g. an antibody phage display library) with PGC-1 to thereby isolate immunoglobulin library members that bind PGC-1. Kits for generating and screening phage display libraries are commercially available (e.g., the Pharmacia *Recombinant Phage Antibody System*, Catalog No. 27-9400-01; and the Stratagene SurfZAP™ Phage Display Kit, Catalog No. 240612). Additionally, examples of methods and reagents particularly amenable for use in generating and screening antibody display library can be found in, for example, Ladner et al., U.S. Pat. No. 5,223,409; Kang et al., PCT International Publication No. WO 92/18619; Dower et al., PCT International Publication No. WO 91/17271; Winter et al., PCT International Publication No. WO 92/20791; Markland et al., PCT International Publication No. WO 92/15679; Breitling et al., PCT International Publication No. WO 93/01288; McCafferty et al., PCT International Publication No. WO 92/01047; Garrard et al., PCT International Publication No. WO 92/09690; Ladner et al., PCT International Publication. No. WO 90/02809; Fuchs et al. (1991) *Biotechnology (NY)* 9:1369-1372; Hay et al. (1992) *Hum. Antibod. Hybridomas* 3:81-85; Huse et al. (1989) *Science* 246:1275-1281; Griffiths et al. (1993) *EMBO J.* 12:725-734; Hawkins et al. (1992) *J. Mol. Biol.* 226:889-896; Clackson et al. (1991) *Nature* 352:624-628; Gram et al. (1992) *Proc. Natl. Acad. Sci. USA* 89:3576-3580; Garrard et al. (1991) *Biotechnology* (NY) 9:1373-1377; Hoogenboom et al. (1991) *Nucleic Acids Res.* 19:4133-4137; Barbas et al. (1991) *Proc. Natl. Acad. Sci. USA* 88:7978-7982; and McCafferty et al. (1990) *Nature* 348:552-554.

Additionally, recombinant anti-PGC-1 antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al., International Application No. PCT/US86/02269; Akira et al., European Patent Application No. 184,187; Taniguchi, M., European Patent Application No. 171,496; Morrison et al., European Patent Application No. 173,494; Neuberger et al., PCT International Publication No. WO 86/01533; Cabilly et al., U.S. Pat. No. 4,816,567; Cabilly et al., European Patent Application No. 125,023; Better et al. (1988) *Science* 240:1041-1043; Liu et al. (1987) *Proc. Natl. Acad. Sci. USA* 84:3439-3443; Liu et al. (1987) *J. Immunol.* 139:3521-3526; Sun et al. (1987) *Proc. Natl. Acad. Sci. USA* 84:214-218; Nishimura et al. (1987) *Cancer Res.* 47:999-1005; Wood et al. (1985) *Nature* 314:446-449; and Shaw et al. (1988) *J. Natl. Cancer Inst.* 80:1553-1559); Morrison, S. L. (1985) *Science* 229:1202-1207; Oi et al. (1986) *Biotechniques* 4:214; Winter, U.S. Pat. No. 5,225,539; Jones et al. (1986) *Nature* 321:552-525; Verhoeyen et al. (1988) *Science* 239:1534; and Beidler et al. (1988) *J. Immunol.* 141:4053-4060.

An anti-PGC-1 antibody (e.g., monoclonal antibody) can be used to isolate PGC-1 by standard techniques, such as affinity chromatography or immunoprecipitation. An anti-PGC-1 antibody can facilitate the purification of natural PGC-1 from cells and of recombinantly produced PGC-1 expressed in host cells. Moreover, an anti-PGC-1 antibody can be used to detect PGC-1 protein (e.g., in a cellular lysate or cell supernatant) in order to evaluate the abundance and pattern of expression of the PGC-1 protein. Anti-PGC-1 antibodies can be used diagnostically to monitor protein levels in tissue as part of a clinical testing procedure, e.g., to, for example, determine the efficacy of a given treatment regiment. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerytlrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

II. Recombinant Expression Vectors and Host Cells

Another aspect of the invention pertains to vectors, for example recombinant expression vectors, containing a PGC-1 nucleic acid molecule or vectors containing a nucleic acid molecule which encodes a PGC-1 protein (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel (1990) *Methods Enzymol.* 185:3-7. Regulatory sequences include those which direct constitutive expression of a nucleotide sequence in many types of host cells and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the invention can be introduced into host cells to thereby produce proteins or peptides, including fusion proteins or peptides, encoded by nucleic acids as described herein (e.g., PGC-1 proteins, mutant forms of PGC-1 proteins, fusion proteins, and the like).

Accordingly, an exemplary embodiment provides a method for producing a protein, preferably a PGC-1 protein, by culturing in a suitable medium a host cell of the invention (e.g., a mammalian host cell such as a non-human mammalian cell) containing a recombinant expression vector, such that the protein is produced.

The recombinant expression vectors of the invention can be designed for expression of PGC-1 proteins in prokaryotic or eukaryotic cells. For example, PGC-1 proteins can be expressed in bacterial cells such as *E. coli*, insect cells (using baculovirus expression vectors) yeast cells or mammalian cells. Suitable host cells are discussed further in Goeddel (1990) supra. Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) Gene 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be utilized in PGC-1 activity assays (e.g., direct assays or competitive assays described in detail below), or to generate antibodies specific for PGC-1 proteins, for example. In a preferred embodiment, a PGC-1 fusion protein expressed in a retroviral expression vector of the present invention can be utilized to infect bone marrow cells, which are subsequently transplanted into irradiated recipients. The pathology of the subject recipient is, then examined after sufficient time has passed (e.g., six (6) weeks).

Examples of suitable inducible non-fusion E. coli expression vectors include pTrc (Amann et al. (1988) Gene 69:301-315) and pETI 11d (Studier et al. (1990) Methods Enzymol. 185:60-89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21 (DE3) or HMS174(DE3) from a resident prophage harboring a T7 gn1 gene under the transcriptional control of the lacUV 5 promoter.

One strategy to maximize recombinant protein expression in E. coli is to express the protein in a host bacteria with an impaired capacity to proteolytically cleave the recombinant protein (Gottesman, S. (1990) Methods Enzymol. 185:119-128). Another strategy is to alter the nucleic acid sequence of the nucleic acid to be inserted into an expression vector so that the individual codons for each amino acid are those preferentially utilized in E. coli (Wada et al. (1992) Nucleic Acids Res. 20:2111-2118). Such alteration of nucleic acid sequences of the invention can be carried out by standard DNA synthesis techniques.

In another embodiment, the PGC-1 expression vector is a yeast expression vector. Examples of vectors for expression in yeast S. cerevisiae include pYepSec1 (Baldari et al. (1987) EMBO J. 6:229-234), pMFa (Kurjan and Herskowitz (1982) Cell 30:933-943), pJRY88 (Schultz et al. (1987) Gene 54:113-123), pYES2 (Invitrogen Corp., San Diego, Calif.), and picZ (Invitrogen Corp., San Diego, Calif.).

Alternatively, PGC-1 proteins can be expressed in insect cells using baculovirus expression vectors. Baculovirus vectors available for expression of proteins in cultured insect cells (e.g., Sf9 cells) include the pAc series (Smith et al. (1983) Mol. Cell Biol. 3:2156-2165) and the pVL series (Lucklow and Summers (1989) Virology 170:31-39).

In yet another embodiment, a nucleic acid of the invention is expressed in mammalian cells using a mammalian expression vector. Examples of mammalian expression vector's include pCDM8 (Seed, B. (1987) Nature 329:840) and pMT2PC (Kaufman et al. (1987) EMBO J. 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17. of Sambrook, J. et al. Molecular Cloning: A Laboratory Manual. $2^{nd}$ ed, Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) Genes Dev. 1:268-277), lymphoid-specific promoters (Calame and Eaton (1988) Adv. Immunol. 43:235-275), in particular promoters of T cell receptors (Winoto and Baltimore (1989) EMBO J. 8:729-733) and immunoglobulins (Baneiji et al. (1983) Cell 33:729-740; Queen and Baltimore (1983) Cell 33:741-748), neuron-specific promoters (e.g., the neurofilament promoter, Byrne and Ruddle (1989) Proc. Natl. Acad. Sci. USA 86:5473-5477), pancreas-specific promoters (Edlund et al. (1985) Science 230:912-916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) Science 249:374-379) and the α-fetoprotein promoter (Campes and Tilghman (1989) Genes Dev. 3:537-546).

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to PGC-1 mRNA. Regulatory sequences operatively linked to a nucleic acid cloned into the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub, H. et al. "Antisense RNA as a molecular tool for genetic analysis", Reviews—Trends in Genetics, Vol. 1(1) 1986.

Another aspect of the invention pertains to host cells into which a PGC-1 nucleic acid molecule of the invention is introduced, e.g., a PGC-1 nucleic acid molecule within a vector (e.g., a recombinant expression vector) or a PGC-1 nucleic acid molecule containing sequences which allow it to homologously recombine into a specific site of the host cell's genome. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a PGC-1 protein can be expressed in bacterial cells such as E. coli, insect cells, yeast or mammalian cells (such as Chinese hamster ovary cells (CHO), COS cells, or C2C12 cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transecting host cells can be found in Sambrook et al. (*Molecular Cloning: A Laboratory Manual.* $2^{nd}$ ed, Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding a PGC-1 protein or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) a PGC-1 protein. Accordingly, the invention further provides methods for producing a PGC-1 protein using the host cells of the invention. In one embodiment, the method comprises culturing the host cell of the invention (into which a recombinant expression vector encoding a PGC-1 protein has been introduced) in a suitable medium such that a PGC-1 protein is produced. In another embodiment, the method further comprises isolating a PGC-1 protein from the medium or the host cell.

The host cells of the invention can also be used to produce non-human transgenic animals. For example, in one embodiment, a host cell of the invention is a fertilized oocyte or an embryonic stem cell into which PGC-1-coding sequences have been introduced. Such host cells can then be used to create non-human transgenic animals in which exogenous PGC-1 sequences have been introduced into their genome or homologous recombinant animals in which endogenous PGC-1 sequences have been altered. Such animals are useful for studying the function and/or activity of a PGC-1 protein and for identifying and/or evaluating modulators of PGC-1 activity. As used herein, a "transgenic animal" is a non-human animal, preferably a mammal, more preferably a rodent such as a rat or mouse, in which one or more of the cells of the animal includes a tangerine. Other examples of transgenic animals include non-human primates, sheep, dogs, cows, goats, chickens, amphibians, and the like. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous PGC-1 gene has been altered by homologous recombination between the endogenous gene and an exogenous DNA molecule introduced into a cell of the animal, e.g., an embryonic cell of the animal, prior to development of the animal.

A transgenic animal of the invention can be created by introducing a PGC-1- encoding nucleic acid into the male pronuclei of a fertilized oocyte, e.g., by microinjection or retroviral infection, and allowing the oocyte to develop in a pseudopregnant female foster animal. The PGC-1 cDNA sequence of SEQ ID NO: 6, 8, 12, or 14 can be introduced as a transgene into the genome of a non-human animal. Alternatively, a non-human homologue of a human PGC-1 gene, such as a rat or mouse PGC-1 gene, can be used as a transgene. Alternatively, a PGC-1 gene homologue, such as another PGC-1 family member, can be isolated based on hybridization to the PGC-1 cDNA sequences of SEQ ID NO: 6, 8, 9, 11, 12, 14, 15, or 17, (described further in subsection I above) and used as a transgene. Intronic sequences and polyadenylation signals can also be included in the transgene to increase the efficiency of expression of the transgene. A tissue-specific regulatory sequence (s) can be operably linked to a PGC-1 transgene to direct expression of a PGC-1 protein to particular cells. Methods for generating transgenic animals via embryo manipulation and microinjection, particularly animals such as mice, have become conventional in the art and are described, for example, in U. S. Pat. Nos. 4,736, 866 and 4,870, 009, both by Leder et al., U. S. Pat. No. 4,873, 191 by Wagner et al. and in Hogan, B., Manipulatis 1 g the Mouse Embryo (Cold Spring Harbor Laboratory Press, Cold Spring Harbor, N. Y., 1986). Similar methods are used for production of other transgenic animals. A transgenic founder animal can be identified based upon the presence of a PGC-1 transgene in its genome and/or expression of PGC-1 mRNA in tissues or cells of the animals. A transgenic founder animal can then be used to breed additional animals carrying the transgene. Moreover, transgenic animals carrying a transgene encoding a PGC-1 protein can further be bred to other transgenic animals carrying other transgenes.

To create a homologous recombinant animal, a vector is prepared which contains at least a portion of a PGC-1 gene into which a deletion, addition or substitution has been introduced to thereby alter, e.g., functionally disrupt, the PGC-1 gene. The PGC-1 gene can be a human gene (e.g., the cDNA of SEQ ID NO:6, 8, 12, or 14), but more preferably, is a non-human homologue of a human PGC-1 gene (e.g., a cDNA isolated by stringent hybridization with the nucleotide sequence of SEQ ID NO:6, 8, 12, or 14), For example, a mouse PGC-1 gene can be used to construct a homologous recombination nucleic acid molecule, e.g., a vector, suitable for altering an endogenous PGC-1 gene in the mouse genome. In a preferred embodiment, the homologous recombination nucleic acid molecule is designed such that, upon homologous recombination, the endogenous PGC-1 gene is functionally disrupted (i.e., no longer encodes a functional protein; also referred to as a "knock out" vector). Alternatively, the homologous recombination nucleic acid molecule can be designed such that, upon homologous recombination, the endogenous PGC-1 gene is mutated or otherwise altered but still encodes functional protein (e.g., the upstream regulatory region can be altered to thereby alter the expression of the endogenous PGC-1 protein). In the homologous recombination nucleic acid molecule, the altered portion of the PGC-1 gene is flanked at its 5' and 3' ends by additional nucleic acid sequence of the PGC-1 gene to allow for homologous recombination to occur between the exogenous PGC-1 gene carried by the homologous recombination nucleic acid molecule and an endogenous PGC-1 gene in a cell, e.g., an embryonic stem cell. The additional flanking PGC-1 nucleic acid sequence is of sufficient length for successful homologous recombination with the endogenous gene. Typically, several kilobases of flanking DNA (both at the 5' and 3' ends) are included in the homologous recombination nucleic acid molecule (see, e.g., Thomas, K. R and Capecchi, M. R. (1987) *Cell* 51:503 for a description of homologous recombination vectors). The homologous recombination nucleic acid molecule is introduced into a cell, e.g., an embryonic stem cell line (e.g., by electroporation) and cells in which the introduced PGC-1 gene has homologously recombined with the endogenous PGC-1 gene are selected (see e.g., Li, E. et al. (1992) *Cell* 69:915). The selected cells can then be injected into a blastocyst of an animal (e.g., a mouse) to form aggregation chimeras (see e.g., Bradley, A. in *Teratocarcinomas and Embryonic Stem Cells: A Practical Approach*, Robertson, E. J. ed. (IRL, Oxford, 1987)pp. 113-152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined. DNA by germline transmission of the transgene. Methods for constructing homologous recombination nucleic acid molecules, e.g., vectors, or homologous recombinant animals are described further in Bradley, A. (1991) *Current Opin. Biotechnol.* 2:823-829 and in PCT International Publication Nos.: WO 90/11354 by Le Mouellec et al.; WO 91/01140 by Smithies et al.; WO 92/0968 by Zijlstra et al.; and WO 93/04169 by Berns et al.

In another embodiment, transgenic non-humans animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) *Proc. Natl. Acad. Sci. USA* 89:6232-6236. Another example of a recombinase system is the FLP recombinase system of *Saccharomyces cerevisiae* (O'Gorman et al. (1991) *Science* 251:1351-1355). If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. (1997) *Nature* 385:810-813and PCT International Publication Nos. WO 97/07668 and WO 97/07669. In brief, a cell, e.g., a somatic cell, from the transgenic animal can be isolated and induced to exit the growth cycle and enter $G_O$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyte and then transferred to pseudopregnant female foster animal. The offspring borne of this female foster animal will be a clone of the animal from which the cell, e.g. the somatic cell, is isolated.

IV. Pharmaceutical Compositions

The PGC-1 nucleic acid molecules, of PGC-1 proteins, fragments thereof, anti-PGC-1 antibodies, and PGC-1 modulators (also referred to herein as "active compounds") of the invention can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols,.glycerine, propyleneglycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example; glycerol, propylene glycol, and liquid, polyetheylene glycol, and the like), and suitable mixtures thereof. The proper fluidity can be maintained, for example; by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a fragment of a PGC-1 protein or an anti-PGC-1 antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or cornstarch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and micro encapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms, of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

In a preferred example, a subject is treated with antibody, protein, or polypeptide in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody, protein, or polypeptide used for treatment may increase or decrease over the course of a particular treatment. Changes in dosage may result and become apparent from the results of diagnostic assays as described herein.

The present invention encompasses agents which modulate expression or activity. An agent may, for example, be a small molecule. For example, such small molecules include, but are not limited to, peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds. It is understood that appropriate doses of small molecule agents depends upon a number of factors within the ken of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention.

Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. Such appropriate doses may be determined using the assays described herein. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

In certain embodiments of the invention, a modulator of PGC-1 activity is administered in combination with other agents (e.g., a small molecule), or in conjunction with another, complementary treatment regime. For example, in one embodiment, a modulator of PGC-1 activity is used to treat PGC-1 associated disorder. Accordingly, modulation of PGC-1 activity may be used in conjunction with, for example, another agent used to treat the disorder.

Further, an antibody (or fragment thereof) may be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, germicide D, ethidium bromide, emetine, mitomycin, etoposide, tenoposide, vincristine, vinblastine, colchicin, doxorubicin, daunorubicin, dihydroxy anthracin dione, mitoxantrone, midiramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomrannitol, streptozotocin, mitomycin C, and cis-dichlorodiamine platinum (II) (DDP) cisplatin), anthracyclines (e.g., daunonibicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, alpha-interferon, beta-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Techniques for conjugating such therapeutic moiety to antibodies are well known, see, e.g., Amon et al. "Monoclonal Antibodies For Immunotargeting Of Drugs In Cancer Therapy" in *Monoclonal Antibodies And Cancer Therapy*, Reisfeld et al. (eds.), pp. 243-56 (Alan R Liss, Inc. 1985); Hellstrom et al. "Antibodies For Drug Delivery" in *Controlled Drug Delivery* (2nd Ed.), Robinson et al. (eds.), pp. 623-53 (Marcel Dekker, Inc. 1987); Thorpe "Antibody Carriers Of Cytotoxic Agents In Cancer Therapy: A Review" in *Monoclonal Antibodies '84: Biological And Clinical Applications*, Pinchera et al. (eds.), pp. 475-506 (1985); "Analysis, Results, And Future Prospective Of The Therapeutic Use Of Radiolabeled Antibody In Cancer Therapy" in *Monoclonal Antibodies For Cancer Detection And Therapy*, Baldwin et al. (eds.), pp. 303-16 (Academic Press 1985); and Thorpe et al. "The Preparation And Cytotoxic Properties Of Antibody-Toxin Conjugates" *Immunol. Rev.* 62:119-58 (1982). Alternatively, an antibody can be conjugated to a second antibody to form an antibody heteroconjugate as described by Segal in U.S. Pat. No. 4,676,980.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *Proc. Natl. Acad. Sci. USA* 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

V. Uses and Methods of the Invention

The nucleic acid molecules, proteins, protein homologues, protein fragments, antibodies, peptides, peptidomimetics, and small molecules described herein can be used in one or more of the following methods: a) screening assays; b) predictive medicine (e.g., diagnostic assays, prognostic assays, monitoring clinical trials, and pharmacogenetics); and c) methods of treatment (e.g.,therapeutic and prophylactic). As described herein, a PGC-1 protein of the invention has one or more of the following activities (i) interaction with a PGC-1 target molecule; (ii) modulation of intracellular signaling; (iii) modulation of cellular metabolism; (iv) localization to peroxisomes; (v) modulation of the expression of genes involved in fatty acid uptake and/or oxidation (e.g., LPL, FAT/CD36, VLACS, AOX, MCAD, and/or MCD); (vi) modulation of fatty acid uptake and/or oxidation; (vii) modulation of energy homeostasis; and/or (viii) modulation of lipid homeostasis.

The isolated nucleic acid molecules of the invention can be used, for example, to express PGC-1 protein (e.g., via a recombinant expression vector in a host cell in gene therapy applications), to detect PGC-1 mRNA (e.g., in a biological sample) or a genetic alteration in a PGC-1 gene, and to modulate PGC-1 activity, as described further below. The PGC-1 proteins can be used to treat disorders characterized by insufficient or excessive production or transport of a PGC-1 target molecule or production of PGC-1 inhibitors, for example, PGC-1 associated disorders.

As used herein, a "PGC-1 associated disorder" includes a disorder, disease or condition which is caused or characterized by a misregulation (e.g., downregulation or upregulation) of PGC-1 activity. PGC-1 associated disorders include disorders, diseases, or conditions related to misregulation (e.g., downregulation or upregulation) of fatty acid uptake and/or oxidation, for example, triglyceride storage disease, steatohepatitis, liver tumors, fatty liver, liver disease, myopathy, hyperlipidemia, hyperlipidemia, dyslipidemia, hypercholesterolemia, hypercholesterolemia, hypertension, stroke, hypertryglyceridemia, hypotriglyceridemia, hyperlipoproteinemia, hypolipoproteinemia, Niemann Pick disease, atherosclerosis, cardiovascular disease, coronary artery disease, obesity, overweight, anorexia, cachexia, diabetes, insulin resistance, hypertension, stroke, pancreatitis, diffuse idiopathic skeletal hyperostosis (DISH), atherogenic lipoprotein phenotype (ALP), epilepsy, and polycystic ovarian syndrome, as well as any disorders, diseases, or conditions which are secondary to those described above.

PGC-1 associated or related disorders also include disorders affecting tissues (e.g., heart or muscle) in which PGC-1 protein is expressed.

In addition, the PGC-1 proteins can be used to screen for naturally occurring PGC-1 target molecules, to screen for drugs or compounds which modulate PGC-1 activity, as well as to treat disorders characterized by insufficient or excessive production of PGC-1 protein or production of PGC-1 protein forms which have decreased, aberrant or unwanted activity compared to PGC-1 wild type protein (e.g., a PGC-1-associated disorder).

Moreover, the anti-PGC-1 antibodies of the invention can be used to detect and isolate PGC-1 proteins, regulate the bioavailability of PGC-1 proteins, and modulate PGC-1 activity.

A. Screening Assays:

The invention provides a method (also referred to herein as a "screening assay") for identifying modulators, i.e., candidate or test compounds or agents (e.g., peptides, peptidomimetics, small molecules or other drugs)which bind to PGC-1 proteins, have a stimulatory or inhibitory effect on, for example, PGC-1 expression or PGC-1 activity, or have a stimulatory or inhibitory effect on, for example, the expression or activity of a PGC-1 target molecule.

In one embodiment, the invention provides assays for screening candidate or test compounds which are target molecules of a PGC-1 protein or polypeptide or biologically active portion thereof In another embodiment, the invention provides assays for screening candidate or test compounds which bind to or modulate the activity of a PGC-1 protein or polypeptide or biologically active portion thereof. The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.* 12:45).

Examples of methods for the synthesis of molecular libraries can be found in the art, for example, in: DeWitt et al. (1993) *Proc. Natl. Acad. Sci. USA* 90:6909; Erb et al. (1994) *Proc. Natl. Acad. Sci. USA* 91:11422; Zuckermann et al. (1994) *J. Med Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed Engl.* 33:2061; and Gallop et al. (1994) *J. Med Chem.* 37:1233.

Libraries of compounds may be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner U.S. Pat. No. 5,223, 409), spores (Ladner U.S. Pat. No. '409), plasmids (Cull et al. (1992) *Proc. Natl. Acad. Sci. USA* 89:1865-1869) or on phage (Scott and Smith (1990) *Science* 249:386390); (Devlin (1990) *Science* 249:404-406); (Cwirla et al. (1990) *Proc. Natl. Acad. Sci. USA* 87:6378-382); (Felici (1991) *J. Mol. Biol* 222:301-310); (Ladner supra).

In one embodiment, an assay is a cell-based assay in which a cell which expresses a PGC-1 protein or biologically active portion thereof is contacted with a test compound and the ability of the test compound to modulate PGC-1 activity is determined. Determining the ability of the test compound to modulate PGC-1-activity can be accomplished by monitoring, for example, expression of genes involved in fatty acid uptake and/or oxidation (e.g., LPL, FAT/CD36, VLACS, AOX, MCAD, and/or MCD), in a cell which expresses PGC-1. The cell, for example, can be of mammalian origin, e.g., a muscle cell such as a primary muscle cell or a C2C12 myoblast or myotube, or a heart cell such as a cardiomyocyte.

The ability of the test compound to modulate PGC-1 binding to a target molecule or to bind to PGC-1 can also be determined. Determining the ability of the test compound to modulate PGC-1 binding to a target molecule can be accomplished, for example, by coupling the PGC-1 target molecule with a radioisotope or enzymatic label such that binding of the PGC-1 target molecule to PGC-1 can be determined by detecting the labeled PGC-1 target molecule in a complex. Alternatively, PGC-1 could be coupled with a radioisotope or enzymatic label to monitor the ability of a test compound to modulate PGC-1 binding to a PGC-1 target molecule in a complex. Determining the ability of the test compound to bind PGC-1 can be accomplished, for example, by coupling the compound with a radioisotope or enzymatic label such that binding of the compound to PGC-1 can be determined by detecting the labeled PGC-1 compound in a complex. For example, compounds (e.g., PGC-1 target molecules) can be labeled with $^{125}I$, $^{35}S$, $^{14}C$, or $^{3}H$, either directly or indirectly, and the radioisotope detected by direct counting of radioemission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

It is also within the scope of this invention to determine the ability of a compound (e.g., a PGC-1 target molecule) to interact with PGC-1 without the labeling of any of the interactants. For example, a microphysiometer can be used to detect the interaction of a compound with PGC-1 without the labeling of either the compound or the PGC-1. McConnell, H. M. et al. (1992) *Science* 257:1906-1912. As used herein, a "microphysiometer" (e.g., Cytosensor) is an analytical instrument that measures the rate at which a cell acidifies its environment using a light-addressable potentiometer sensor (LAPS). Changes in this acidification rate can be used as an indicator of the interaction between a compound and PGC-1.

In another embodiment, an assay is a cell-based assay comprising contacting a cell expressing a PGC-1 target molecule (e.g., a PGC-1 polypeptide or a non-PGC-1 potassium channel subunit) with a test compound and determining the ability of the test compound to modulate (e.g., stimulate or inhibit) the activity of the PGC-1 target molecule. Determining the ability of the test compound to modulate the activity of a PGC-1 target molecule can be accomplished, for example, by determining the ability of a PGC-1 protein to bind to or interact with the PGC-1 target molecule, or by determining the ability of a PGC-1 protein to modulate expression of genes involved in fatty acid uptake and/or oxidation (e.g., LPL, FAT/CD36, VLACS, AOY, MCAD, and/or MCD).

Determining the ability of the PGC-1 protein, or a biologically active fragment thereof, to bind to or interact with a PGC-1 target molecule can be accomplished by one of the methods described above for determining direct binding. In a preferred embodiment, determining the ability of the PGC-1 protein to bind to or interact with a PGC-1 target molecule can be accomplished by determining the activity of the target molecule. For example, the activity of the target molecule can be determined by detecting induction of a cellular response, detecting catalytic/enzymatic activity of the target molecule upon an appropriate substrate, detecting the induction of a reporter gene (comprising a target-responsive regulatory element operatively linked to a nucleic acid encoding a detectable marker, e.g., luciferase), or detecting a target-regulated cellular response (i.e., modulation of fatty acid uptake and/or oxidation).

In yet another embodiment, an assay of the present invention is a cell-free assay in which a PGC-1 protein or biologically active portion thereof is contacted with a test compound and the ability of the test compound to bind to the PGC-1 protein or biologically active portion thereof is determined. Preferred biologically active portions of the PGC-1 proteins to be used in assays of the present invention include fragments which participate in interactions with non-PGC-1 molecules, e.g., fragments with high surface probability scores. Further preferred PGC-1 proteins include amino acid sequences which are unique to PGC-1b or PGC-1c, e.g., SEQ ID NO:10 or SEQ ID NO:16, or fragments thereof. Binding of the test compound to the PGC-1 protein can be determined either directly or indirectly as described above. In a preferred embodiment, the assay includes contacting the PGC-1 protein or biologically active portion thereof with a known compound which binds PGC-1 to form an assay mixture, contacting the assay mixture with a test compound, and determining the ability of the test compound to interact with a PGC-1 protein, wherein determining the ability of the test compound to interact with a PGC-1 protein comprises determining the ability of the test compound to referentially bind to PGC-1 or biologically active portion thereof as compared to the known compound.

In another embodiment, the assay is a cell-free assay in which a PGC-1 protein or biologically active portion thereof is contacted with a test compound and the ability of the test compound to modulate (e.g., stimulate or inhibit) the activity of the PGC-1 protein or biologically active portion thereof is determined. Determining the ability of the test compound to modulate the activity of a PGC-1 protein can be accomplished, for example, by determining the ability of the PGC-1 protein to bind to a PGC-1 target molecule by one of the methods described above for determining direct binding. Determining the ability of the PGC-1 protein to bind to a PGC-1 target molecule can also be accomplished using a technology such as real-time Biomolecular Interaction Analysis (BIA). Sjolander, S. and Urbaniczky, C. (1991) *Anal. Chem.* 63:2338-2345 and Szabo et al. (1995) *Curr. Opin. Struct. Biol.* 5:699-705. As used herein, "BIA" is a technology for studying biospecific interactions in real time, without labeling any of the interactants (e.g., BIAcore). Changes in the optical phenomenon of surface plasmon resonance (SPR) can be used as an indication of real-time reactions between biological molecules.

In an alternative embodiment, determining the ability of the test compound to modulate the activity of a PGC-1 protein can be accomplished by determining the ability of the PGC-1 protein to further modulate the activity of a downstream effector of a PGC-1 target molecule. For example, the activity of the effector molecule on an appropriate target can be determined or the binding of the effector to an appropriate target can be determined as previously described.

In yet another embodiment, the cell-free assay involves contacting a PGC-1 protein or biologically active portion thereof with a known compound which binds the PGC-1 protein to form an assay mixture, contacting the assay mixture with a test compound, and determining the ability of the test compound to interact with the PGC-1 protein, wherein determining the ability of the test compound to interact with the PGC-1 protein comprises determining the ability of the PGC-1 protein to preferentially bind to or modulate the activity of a PGC-1 target molecule.

In more than one embodiment of the above assay methods of the present invention, it may be desirable to immobilize either PGC-1 or its target molecule to facilitate separation of complexed from uncomplexed forms of one or both of the proteins, as well as to accommodate automation of the assay. Binding of a test compound to a PGC-1 protein, or interaction of a PGC-1 protein with a target molecule in the presence and absence of a candidate compound, can be accomplished in any vessel suitable for containing the reactants. Examples of such vessels include microtiter plates, test tubes, and micro-centrifuge tubes. In one embodiment, a fusion protein can be provided which adds a domain that allows one or both of the proteins to be bound to a matrix. For example, glutathione-S-transferase/PGC-1 fusion proteins or glutathione-S-transferase/target fusion proteins can be adsorbed onto glutathione sepharose beads (Sigma Chemical, St. Louis, Mo.) or glutathione derivatized micrometer plates, which are then combined with the test compound or the test compound and either the non-adsorbed target protein or PGC-1 protein, and the mixture incubated under conditions conducive to complex formation (e.g., at physiological conditions for salt and pH). Following incubation, the beads or microtiter plate wells are washed to remove any unbound components, the matrix immobilized in the case, of beads, complex determined either directly or indirectly, for example, as described above. Alternatively, the complexes can be dissociated from the matrix, and the level of PGC-1 binding or activity determined using standard techniques.

Other techniques for immobilizing proteins on matrices can also be used in the screening assays of the invention. For example, either a PGC-1 protein or a PGC-1 target molecule can be immobilized utilizing conjugation of biotin and streptavidin. Biotinylated PGC-1 protein or target molecules can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical). Alternatively, antibodies reactive with PGC-1 protein or target molecules but which do not interfere with binding of the PGC-1 protein to its target molecule can be derivatized to the wells of the plate, and unbound target or PGC-1 protein trapped in the wells by antibody conjugation. Methods for detecting such complexes, in addition to those described above for the GST-immobilized complexes, include immunodetection of complexes using antibodies reactive with the PGC-1 protein or target molecule, as well as enzyme-linked assays which rely on detecting an enzymatic activity associated with the PGC-1 protein or target molecule.

In another embodiment, modulators of PGC-1 expression are identified in a method wherein a cell is contacted with a candidate compound and the expression of PGC-1 mRNA or protein in the cell is determined. The level of expression of PGC-1 mRNA or protein in the presence of the candidate compound is compared to the level of expression of PGC-1 mRNA or protein in the absence of the candidate compound. The candidate compound can then be identified as a modulator of PGC-1 expression based on this comparison. For example, when expression of PGC-1 mRNA or protein is greater (statistically significantly greater) in the presence of the candidate compound than in its absence, the candidate compound is identified as a stimulator of PGC-1 mRNA or protein expression. Alternatively, when expression of PGC-1 mRNA or protein is less (statistically significantly less) in the presence of the candidate compound than in its absence, the candidate compound is identified as an inhibitor of PGC-1 mRNA or protein expression. The level of PGC-1 mRNA or protein expression in the cells can be determined by methods described herein for detecting PGC-1 mRNA or protein.

In yet another aspect of the invention, the PGC-1 proteins can be used as "bait proteins" in a two-hybrid assay or three-hybrid assay (see, e.g, U.S. Pat. No. 5,283,317; Zervos et al. (1993) Cell 72:223-232; Madura et al. (1993) J. Biol. Chem. 268:12046-12054; Bartel et al. (1993) Biotechniques 14:920-924; Iwabuchi et al. (1993). Oncogene 8:1693-1696; and Brent WO 94/10300) to identify other proteins which bind to or interact with PGC-1 ("PGC-1-binding proteins" or "PGC-1-bp") and are involved in PGC-1 activity. Such PGC-1-binding proteins are also likely to be involved in the propagation of signals by the PGC-1 proteins or PGC-1 targets as, for example, downstream elements of a PGC-1-mediated signaling pathway. Alternatively, such PGC-1-binding proteins may be PGC-1 inhibitors.

The two-hybrid system is based on the modular nature of most transcription factors, which consist of separable DNA-binding and activation domains. Briefly, the assay utilizes two different-DNA constructs. In one construct, the gene that codes for a PGC-1 protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a PGC-1-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the PGC-1 protein.

In another aspect, the invention pertains to a combination of two or more of the assays described herein. For example, a modulating agent can be identified using a cell-based or a cell-free assay, and the ability of the agent to modulate the activity of a PGC-1 protein can be confirmed in vivo, e.g., in an animal such as an animal model for fatty acid metabolism. Such animal models are known in the art and include mice deficient in various genes involved in fatty acid uptake and/or oxidation, for example, mice deficient for peroxisomal Acyl-CoA oxidase (Fan, C. Y. et al. (1998) J. Biol. Chem. 273(25):15639-45) or the transcription factor PPARα, or mice overexpressing lipoprotein lipase in skeletal muscle and heart.

This invention further pertains to novel agents identified by the above-described screening assays. Accordingly, it is within the scope of this invention to further use an agent identified as described herein in an appropriate animal model. For example, an agent identified as described herein (e.g., a PGC-1 modulating agent, an antisense PGC-1 nucleic acid molecule, a PGC-1-specific antibody, or a PGC-1 binding partner) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

B. Detection Assays

Portions or fragments of the cDNA sequences identified herein (and the corresponding complete gene sequences) can be used in numerous ways as polynucleotide reagents. For example, these sequences can be used to: (i) map their respective genes on a chromosome; and, thus, locate gene regions associated with genetic disease; (ii) identify an individual from a minute biological sample (tissue typing); and (iii) aid in forensic identification of a biological sample. These applications are described in the subsections below.

1. Chromosome Mapping

Once the sequence (or a portion of the sequence) of a gene has been isolated, this sequence can be used to map the location of the gene on a chromosome. This process is called chromosome mapping. Accordingly, portions or fragments of the PGC-1 nucleotide sequences, described herein, can be used to map the location of the PGC-1 genes on a chromosome. The mapping of the PGC-1 sequences to chromosomes is an important first step in correlating these sequences with genes associated with disease.

Briefly, PGC-1 genes can be mapped to chromosomes by preparing PCR primers (preferably 15-25 nucleotides in length) from the PGC-1 nucleotide sequences. Computer analysis of the PGC-1 sequences can be used to predict primers that do not span more than one exon in the genomic DNA, thus complicating the amplification process. These primers can then be used for PCR screening of somatic cell hybrids containing individual human chromosomes. Only those hybrids containing the human gene corresponding to the PGC-1 sequences will yield an amplified fragment.

Somatic cell hybrids are prepared by fusing somatic cells from different mammals (e.g., human and mouse cells). As hybrids of human and mouse cells grow and divide, they gradually lose human chromosomes in random order, but retain the mouse chromosomes. By using media in which mouse cells cannot grow, because they lack a particular enzyme, but human cells can, the one human chromosome that contains the gene encoding the needed enzyme, will be retained. By using various media, panels of hybrid cell lines can be established. Each cell line in a panel contains either a single human chromosome or a small number of human chromosomes, and a fill set of mouse chromosomes, allowing easy mapping of individual genes to specific human chromosomes (D'Eustachio P. et al. (1983) *Science* 220: 919-924). Somatic cell hybrids containing only fragments of human chromosomes can also be produced by using human chromosomes with translocations and deletions.

PCR mapping of somatic cell hybrids is a rapid procedure for assigning a particular sequence to a particular chromosome. Three or more sequences can be assigned per day using a single thermal cycler. Using the PGC-1 nucleotide sequences to design oligonucleotide primers, sublocalization can be achieved with panels of fragments from specific chromosomes. Other mapping strategies which can similarly be used to map a PGC-1 sequence to its chromosome include in situ hybridization (described in Fan, Y. et al. (1990) *Proc. Natl. Acad. Sci. USA* 87:6223-27), pre-screening with labeled flow-sorted chromosomes, and pre-selection by hybridization to chromosome-specific cDNA libraries.

Fluorescence in situ hybridization (FISH) of a DNA sequence to a metaphase chromosomal spread can further be used to provide a precise chromosomal location in one step. Chromosome spreads can be made using cells whose division has been blocked in metaphase by a chemical such as colcemid that disrupts the mitotic spindle. The chromosomes can be treated briefly with trypsin, and then stained with Giemsa. A pattern of light and dark bands develops on each chromosomes so that the chromosomes can be identified individually. The FISH technique can be used with a DNA sequence as short as 500 or 600bases. However, clones larger than 1,000 bases have a higher likelihood of binding to a unique chromosomal location with sufficient signal intensity for simple detection. Preferably 1000 bases, and more preferably 2,000 bases will suffice to get good results at a reasonable amount of time. For a review of this technique, see Verma et al., *Human Chromosomes: A Manual of Basic Technique* (Pergamon Press, New York 1988).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data (such data are found, for example, in McKusick, V., Mendelian Inheritance in Man, available on-line through Johns Hopkins University Welch Medical Library). The relationship between a gene and a disease, mapped to the same chromosomal region, can then be identified through linkage analysis (co-inheritance of physically adjacent genes), described in, for example, Egeland, J. et al. (1987) *Nature* 325:783-787.

Moreover, differences in the DNA sequences between individuals affected and unaffected with a disease associated with the PGC-1 gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

2. Tissue Typing

The PGC-1 sequences of the present invention can also be used to identify individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identification. This method does not suffer from the current limitations of "Dog Tags" which can be lost, switched, or stolen, making positive identification difficult. The sequences of the present invention are useful us additional DNA markers for RFLP (described in U.S. Pat. No. 5,272,057).

Furthermore, the sequences of the present invention can be used to provide an alternative technique which determines the actual base-by-base DNA sequence of selected portions of an individual's genome. Thus, the PGC-1nucleotide sequences described herein can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the present invention can be used to obtain such identification sequences from individuals and from tissue. The PGC-1 nucleotide sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ I) NO:6, 9, 12, or 15 can comfortably provide positive individual identification with a panel of perhaps 10 to 1,000 primers which each yield a noncoding amplified sequence of 100 bases. If predicted coding sequences, such as those in SEQ ID NO:8, 11, 14, or 17 are used, a more appropriate number of primers for positive individual identification would be 500-2,000.

If a panel of reagents from PGC-1 nucleotide sequences described herein is used to generate a unique identification database for an individual, those same reagents can later be used to identify tissue from that individual. Using the unique identification database, positive identification of the individual, living or dead, can be made from extremely small tissue samples.

3. Use of Partial PGC-1 Sequences in Forensic Biology

DNA-based identification techniques can also be used in forensic biology. Forensic biology is a scientific field employing genetic typing of biological evidence found at a crime scene as a means for positively identifying, for example, a perpetrator of a crime. To make such an identification, PCR technology can be used to amplify DNA sequences taken from very small biological samples such as tissues; e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e., another DNA sequence that is unique to a particular individual). As mentioned above, actual base sequence information can be used for identification as an accurate alternative to patterns formed by restriction enzyme generated fragments. Sequences targeted to noncoding regions of SEQ ID NO:1 are particularly appropriate for this use as greater numbers of polymorphisms occur in the noncoding regions, making it easier to differentiate individuals using this technique. Examples of polynucleotide reagents include the PGC-1 nucleotide sequences or portions thereof, e.g., fragments derived from the noncoding regions of SEQ ID NO:1 having a length of at least 20 bases, preferably at least 30 bases.

The PGC-1 nucleotide sequences described herein can further be used to provide polynucleotide reagents, e.g., labeled or labelable probes which can be used in, for example, an in situ hybridization technique, to identify a specific tissue, e.g. a tissue which expresses PGC-1, such as heart or muscle. This can be very useful in cases where a forensic pathologist is presented with a tissue of unknown origin. Panels of such PGC-1 probes can be used to identify tissue by species and/or by organ type.

In a similar fashion, these reagents, e.g., PGC-1 primers or probes can be used to screen tissue culture for contamination (i.e., screen for the presence of a mixture of different types of cells in a culture).

C. Predictive Medicine:

The present invention also pertains to the field of predictive medicine in which diagnostic assays, prognostic assays, and monitoring clinical trials are used for prognostic (predictive) purposes to thereby treat an individual prophylactically. Accordingly, one aspect of the present invention relates to diagnostic assays for determining PGC-1 protein and/or nucleic acid expression as well as PGC-1 activity, in the context of a biological sample (e.g. blood, serum, cells, or tissue) to thereby determine whether an individual is afflicted with a disease or disorder (e.g., a PGC-1 associated disorder), or is at risk of developing a disorder, associated with aberrant or unwanted PGC-1 expression or activity. The invention also provides for prognostic (or predictive) assays for determining whether an individual is at risk of developing a disorder associated with PGC-1 protein, nucleic acid expression, or activity. For example, mutations in a PGC-1 gene can be assayed in a biological sample. Such assays can be used for prognostic or predictive purpose to thereby prophylactically treat an individual prior to the onset of a disorder characterized by or associated with PGC-1 protein, nucleic acid expression or activity.

Another aspect of the invention pertains to monitoring the influence of agents (e.g., drugs, compounds) on the expression or activity of PGC-1 in clinical trials.

These and other agents are described in further detail in the following sections.

1. Diagnostic Assays

An exemplary method for detecting the presence or absence of PGC-1 protein, polypeptide or nucleic acid in a biological sample involves obtaining a biological sample from a test subject and contacting the biological sample with a compound or an agent capable of detecting PGC-1 protein, polypeptide or nucleic acid (e.g., mRNA, genomic DNA) that encodes PGC-1 protein such that the presence of PGC-1 protein or nucleic acid is detected in the biological sample. In another aspect, the present invention provides a method for detecting the presence of PGC-1 activity in a biological sample by contacting the biological sample with an agent capable of detecting an indicator of PGC-1 activity such that the presence of PGC-1 activity is detected in the biological sample. A preferred agent for detecting PGC-1 mRNA or genomic DNA is a labeled nucleic acid probe capable of hybridizing to PGC-1 mRNA or genomic DNA. The nucleic acid probe can be, for example, a full-length PGC-1 nucleic acid, such as the nucleic acid of SEQ ID NO: 6, 8, 9, 11, 12, 14, 15, or 17, or a portion thereof such as an oligonucleotide of at least 15,30, 50,100, 250 or 500 nucleotides in length and sufficient to specifically hybridize under stringent conditions to PGC-1 mRNA or genomic DNA. Other suitable probes for use in the diagnostic assays of the invention are described herein.

A preferred agent for detecting PGC-1 protein is an antibody capable of binding to PGC-1 protein, preferably an antibody with a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect PGC-1 mRNA, protein, or genomic DNA in a biological sample in vitro as well as in vivo. For example, in vitro techniques for detection of PGC-1 mRNA include Northern hybridizations and in situ hybridizations. In vitro techniques for detection of PGC-1 protein include enzyme linked immunosorbent assays (ELISAs), Western blots, immunoprecipitations and immunofluorescence. In vitro techniques for detection of PGC-1 genomic DNA include Southern hybridizations. Furthermore, in vivo techniques for detection of a PGC-1 protein include introducing into a subject a labeled anti-PGC-1 antibody. For example, the antibody can be labeled with a radioactive marker whose presence and location in a subject can be detected by standard imaging techniques.

The present invention also provides diagnostic assays for identifying the presence or absence of a genetic alteration characterized by at least one of (i) aberrant modification or mutation of a gene encoding a PGC-1 protein; (ii) aberrant expression of a gene encoding a PGC-1 protein; (iii) miss-regulation of the gene; and (iii) aberrant post-translational modification of a PGC-1 protein, wherein a wild-type form of the gene encodes a protein with a PGC-1 activity. "Misexpression or aberrant expression", as used herein, refers to a non-wild type pattern of gene expression, at the RNA or protein level. It includes, but is not limited to, expression at non-wild type levels (e.g., over or under expression); a pattern of expression that differs from wild type in terms of the time or stage at which the gene is expressed (e.g., increased or decreased expression (as compared with wild type) at a predetermined developmental period or stage); a pattern of expression that differs from wild type in terms of decreased expression (as compared with wild type) in a predetermined cell type or tissue type; a pattern of expression that differs from wild type in terms of the splicing size, amino acid sequence, post-transitional modification, or biological activity of the expressed polypeptide; a pattern of expression that differs from wild type in terms of the effect of an environmental stimulus or extracellular stimulus on expression of the gene (e.g., a pattern of increased or decreased expression (as compared with wild type) in the presence of an increase or decrease in the strength of the stimulus).

In one embodiment, the biological sample contains protein molecules from the test subject. Alternatively, the biological sample can contain mRNA molecules from the test subject or genomic DNA molecules from the test subject A preferred biological sample is a serum sample isolated by conventional means from a subject.

In another embodiment, the methods further involve obtaining a control biological sample from a control subject, contacting the control sample with a compound or agent capable of detecting PGC-1 protein, mRNA, or genomic DNA, such that the presence of PGC-1 protein, mRNA or genomic DNA is detected in the biological sample, and comparing the presence of PGC-1 protein, mRNA or genomic DNA in the control sample with the presence of PGC-1 protein, mRNA or genomic DNA in the test sample.

The invention also encompasses kits for detecting the presence of PGC-1 in a biological sample. For example, the kit can comprise a labeled compound or agent capable of detecting PGC-1 protein or mRNA in a biological sample; means for determining the amount of PGC-1 in the sample; and means for comparing the amount of PGC-1 in the sample with a standard. The compound or agent can be packaged in a suitable container. The kit an further comprise instructions for using the kit to detect PGC-1 protein or nucleic acid.

2. Prognostic Assays

The diagnostic methods described herein can furthermore be utilized to identify subjects having or at risk of developing a disease or disorder (e.g., a PGC-1 associated disorder) associated with aberrant or unwanted PGC-1 expression or activity. As used herein, the term "aberrant" includes a PGC-1 expression or activity which deviates from the wild type PGC-1 expression or activity. Aberrant expression or activity includes increased or decreased expression or activity, as well as expression or activity which does not follow the wild type developmental pattern of expression or the subcellular pattern of expression. For example, aberrant PGC-1 expression or activity is intended to include the cases in which a mutation in the PGC-1 gene causes the PGC-1 gene to be under-expressed or over-expressed and situations in which such mutations result in a non-functional PGC-1 protein or a protein which does not function in a wild-type fashion, e.g., a protein which does not interact with a PGC-1 target molecule, or one which interacts with a non-PGC-1 target molecule. As used herein, the term "unwanted" includes an unwanted phenomenon involved in a biological response such as deregulated fatty acid uptake and/or oxidation. For example, the term unwanted includes a PGC-1 expression or activity which is undesirable in a subject.

The assays described herein, such as the preceding diagnostic assays or the following assays, can be utilized to identify a subject having or at risk of developing a disorder associated with a misregulation in PGC-1 protein activity or nucleic acid expression, such as a PGC-1 associated. Alternatively, the prognostic assays can be utilized to identify a subject having or at risk for developing a disorder associated with a misregulation in PGC-1 protein activity or nucleic acid expression, such as a PGC-1 associated. Thus, the present invention provides a method for identifying a disease or disorder associated with aberrant or unwanted PGC-1 expression or activity in which a test sample is obtained from a subject and PGC-1 protein or nucleic acid (e.g, mRNA or genomic DNA) is detected, wherein the presence of PGC-1 protein or nucleic acid is diagnostic for a subject having or at risk of developing a disease or disorder associated with aberrant or unwanted PGC-1 expression or activity. As used herein, a "test sample" refers to a biological sample obtained from a subject of interest. For example, a test sample can be a biological fluid (e.g., serum), cell sample, or tissue.

Furthermore, the prognostic assays described herein can be used to determine whether a subject can be administered an agent (e.g., anagonist, antagonist, peptidomimetic, protein; peptide, nucleic acid, small molecule, or other drug candidate) to treat a disease or disorder associated with aberrant or unwanted PGC-1 expression or activity. For example, such methods can be used to determine whether a subject can be effectively treated with an agent for a drug or toxin sensitivity disorder or a cell proliferation and/or differentiation disorder. Thus, the present invention provides methods for determining whether a subject can be effectively treated with an agent for a disorder associated with aberrant or unwanted PGC-1 expression or activity in which a test sample is obtained and PGC-1 protein or nucleic acid expression or activity is detected (e.g., wherein the abundance of PGC-1 protein or nucleic acid expression or activity is diagnostic for a subject that can be administered the agent to treat a disorder associated with aberrant or unwanted PGC-1 expression or activity).

The methods of the invention can also be used to detect genetic alterations in a PGC-1 gene, thereby determining if a subject with the altered gene is at risk for a disorder characterized by misregulation in PGC-1 protein activity or nucleic acid expression, such as a PGC-1 associated disorder. In preferred embodiments, the methods include detecting, in a sample of cells from the subject, the presence or absence of a genetic alteration characterized by at least one of an alteration affecting the integrity of a gene encoding a PGC-1-protein, or the mis-expression of the PGC-1 gene. For example, such genetic alterations can be detected by ascertaining the existence of at least one of 1) a deletion of one or more nucleotides from a PGC-1 gene; 2) an addition of one or more nucleotides to a PGC-1 gene; 3) a substitution of one or more nucleotides of a PGC-1 gene, 4) a chromosomal rearrangement of a PGC-1 gene; 5) an alteration in the level of a messenger RNA transcript of a PGC-1 gene, 6) aberrant modification of a PGC-1 gene, such as of the methylation pattern of the genomic DNA, 7) the presence of a non-wild type splicing pattern of a messenger RNA transcript of a PGC-1 gene, 8) a non-wild type level of a PGC-1-protein, 9) allelic loss of a PGC-1 gene, and 10) inappropriate post-translational modification of a PGC-1-protein As described herein, there are a large number of assays known in the art which can be used for detecting alterations in a PGC-1 gene. A preferred biological samplers a tissue or serum sample isolated by conventional means from a subject.

In certain embodiments, detection of the alteration involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077-1080; and Nakazawa et al. (1994) *Proc. Natl. Acad. Sci. USA* 91:360-364), the latter of which can be particularly useful for detecting point mutations in the PGC-1-gene (see Abravaya et al. (1995) *Nucleic Acids Res.* 23:675-682). This method can include the steps of collecting a sample of cells from a subject, isolating nucleic acid (e.g., genomic, mRNA or both) from the cells of the sample, contacting the nucleic acid sample with one or more primers which specifically hybridize to a PGC-1 gene under conditions such that hybridization and amplification of the PGC-1-gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al. (1990) *Proc. Natl. Acad. Sci. USA* 87:1874-1878), transcriptional amplification system (Kwoh, D. Y. et al. (1989) *Proc. Natl. Acad. Sci. USA* 86:1173-1177), Q-Beta Replicase (Lizardi, P. M. et al. (1988) *Bio-Technology* 6:1.197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a PGC-1 gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in PGC-1 can be identified by hybridizing a sample and control nucleic acids, e.g., DNA or RNA, to high density arrays containing hundreds or thousands of oligonucleotides probes (Cronin, M. T. et al. (1996) *Hum. Mutat.* 7:244-255; Kozal, M. J. et al. (1996) *Nat. Med* 2:753-759). For example, genetic mutations in PGC-1 can be identified in two dimensional arrays containing light-generated DNA probes as described in Cronin et al. (1996) supra Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the PGC-1 gene and detect mutations by comparing the sequence of the sample PGC-1 with the corresponding wild-type (control) sequence. Examples of sequencing reactions include those based on techniques developed by Maxam and Gilbert ((1977) *Proc. Natl. Acad. Sci. USA* 74:560) or Sanger ((1977) *Proc. Natl. Acad. Sci. USA* 74:5463). It is also contemplated that any of a variety of automated sequencing procedures can be utilized when performing the diagnostic assays (Naeve, C. W. (1995) *Biotechniques* 19:448), including sequencing by mass spectrometry (see, e.g., PCT International Publication No. WO 94/16101; Cohen et al. (1996) *Adv. Chromatogr.* 36:127-162; and Griffin et al. (1993) *Appl. Biochem. Biotechnol.* 38:147-159).

Other methods for detecting mutations in the PGC-1 gene include methods in which protection from cleavage agents is used to detect mismatched bases in RNA/RNA or RNA/DNA heteroduplexes (Myers et al. (1985) *Science* 230:1242). In general, the art technique of "mismatch cleavage" starts by providing heteroduplexes formed by hybridizing (labeled) RNA or DNA containing the wild-type PGC-1 sequence with potentially mutant RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) *Proc. Natl. Acad. Sci. USA* 85:4397; Saleeba et al. (1992) *Methods Enzymol.* 217:286-295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes).in defined systems for detecting and mapping point mutations in PGC-1 cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657-1662). According to an exemplary embodiment, a probe based on a PGC-1 sequence, e.g., a wild-type PGC-1 sequence, is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations in PGC-1 genes. For example, single strand conformation polymorphism (SSCP) maybe used to detect differences in electrophoretic mobility between mutant and wild type nucleic acids (Orita et al. (1989) *Proc. Natl. Acad. Sci. USA* 86:2766; see also Cotton (1993) *Mutat. Res.* 285:125-144; and Hayashi (1992) *Genet. Anal. Tech. Appl.* 9:73-79). Single-stranded DNA fragments of sample and control PGC-1 nucleic acids will be denatured and allowed to renature. The secondary structure of single-stranded nucleic acids varies according to sequence, the resulting alteration in electrophoretic mobility enables the detection of even a single base change The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet.* 7:5).

In yet another embodiment the movement of mutant or wild-type fragments in polyacrylamide gels containing a gradient of denaturant is assayed using denaturing, gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR In a further embodiment, a temperature gradient is used in place of a denaturing gradient to identify differences in the mobility of control and sample DNA (Rosenbaum and Reissner (1987) *Biophys. Chem.* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature* 324:163); Saiki et al. (1989) *Proc. Natl. Acad. Sci. USA* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids. Res.* 17:2437-2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci. USA* 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a PGC-1 gene.

Furthermore, any cell type or tissue in which PGC-1 is expressed (e.g., heart or muscle) may be utilized in the prognostic assays described herein.

3. Monitoring of Effects During Clinical Trials

Monitoring the influence of agents (e.g., drugs) on the expression or activity of a PGC-1 protein (e.g., the modulation of PGC-1 activity, expression of fatty acid uptake and/or oxidation genes, and/or fatty acid uptake and/or oxidation mechanisms) can be applied not only in basic drug screening, but also in clinical trials. For example, the effectiveness of an agent determined by a screening assay as described herein to increase PGC-1 gene expression, protein levels, or upregulate PGC-1 activity, can be monitored in clinical trials of subjects exhibiting decreased PGC-1 gene expression, protein levels, or downregulated PGC-1 activity. Alternatively, the effectiveness of an agent determined by a screening assay to decrease PGC-1 gene expression, protein levels, or downregulate PGC-1 activity, can be monitored in clinical trials of subjects exhibiting increased PGC-1 gene expression, protein levels, or unregulated PGC-1 activity. In such clinical trials, the expression or activity of a PGC-1 gene, and preferably, other genes that have been implicated in, for example, a PGC-1-associated disorder can be used as a "read out" or markers of the phenotype of a particular cell.

For example, and not by way of limitation, genes, including PGC-1, that are modulated in cells by treatment with an agent (e.g., compound, drug or small molecule) which modulates PGC-1 activity (e.g., identified in a screening assay as described herein) can be identified. Thus, to study the effect of agents on PGC-1-associated disorders (e.g., disorders characterized by deregulated PGC-1 activity, expression of fatty acid uptake and/or oxidation genes, and/or fatty acid uptake and/or oxidation mechanisms), for example, in a clinical trial, cells can be isolated and RNA prepared and analyzed for the levels of expression of PGC-1 and other genes implicated in the PGC-1-associated disorder, respectively. The levels of gene expression (e.g., a gene expression pattern) can be quantified by northern blot analysis or RT-PCR, as described herein, or alternatively by measuring the amount of protein produced, by one of the methods as described herein, or by measuring the levels of activity of PGC-1 or other genes. In this way, the gene expression pattern can serve as a marker, indicative of the physiological response of the cells to the agent. Accordingly, this response state may be determined before, and at various points during treatment of the individual with the agent.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) including the steps of (i) obtaining a pre-administration sample from a subject prior to administration of the agent; (ii) detecting the level of expression of a PGC-1 protein, mRNA, or genomic DNA in the preadministration sample; (iii) obtaining one or more post-administration samples from the subject; (iv) detecting the level of expression or activity of the PGC-1 protein, mRNA, or genomic DNA in the post-adminisration samples; (v) comparing the level of expression or activity of the PGC-1 protein, mRNA, or genomic DNA in the pre-administration sample with the PGC-1 protein, mRNA, or genomic DNA in the post administration sample or samples; and (vi) altering the administration of the agent to the subject accordingly. For example, increased administration of the agent may be desirable to increase the expression or activity of PGC-1 to higher levels than detected, i.e., to increase the effectiveness of the agent. Alternatively, decreased administration of the agent may be desirable to decrease expression or activity of PGC-1 to lower levels than detected, i.e., to decrease the effectiveness of the agent. According to such an embodiment, PGC-1 expression or activity may be used as an indicator of the effectiveness of an agent, even in the absence of an observable phenotypic response.

D. Methods of Treatment:

The present invention provides for both prophylactic and therapeutic methods of treating a subject at risk of (or susceptible to) a disorder or having a PGC-1-associated disorder, e.g., a disorder associated with aberrant or unwanted PGC-1 expression or activity (e.g., a PGC-1 associated disorder). As used herein, "treatment" of a subject includes the application or administration of a therapeutic agent to a subject, or application or administration of a therapeutic agent to a cell or tissue from a subject, who has a diseases or disorder, has a symptom of a disease or disorder, or is at risk of (or susceptible to) a disease or disorder, with the purpose to cure, heal, alleviate, relieve, alter, remedy, ameliorate, improve, or affect the disease or disorder, the symptom of the disease or disorder, or the risk of (or susceptibility to) the disease or disorder. As used herein, a "therapeutic agent" includes, but is not limited to, small molecules, peptides, polypeptides, antibodies, ribozymes, and antisense oligonucleotides.

With regards to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype"). Thus, another aspect of the invention provides methods for tailoring an individual's prophylactic or therapeutic treatment with either the PGC-1 molecules of the present invention or PGC-1 modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

1. Prophylactic Methods

In one aspect, the invention provides a method for preventing in a subject, a disease or condition associated with an aberrant or unwanted PGC-1 expression or activity, by administering to the subject a PGC-1 or an agent which modulates PGC-1 expression or at least one PGC-1 activity. Subjects at risk for a disease which is caused or contributed to by aberrant or unwanted PGC-1 expression or activity can be identified by, for example, any or a combination of diagnostic or prognostic assays as described herein. Administration of a prophylactic agent can occur prior to the manifestation of symptoms characteristic of the PGC-1 aberrancy, such that a disease or disorder is prevented or, alternatively, delayed in its progression. Depending on the type of PGC-1 aberrancy, for example, a PGC-1, PGC-1 agonist or PGC-1 antagonist agent can be used for treating the subject. The appropriate agent can be determined based on screening assays described herein.

2. Therapeutic Methods

Another aspect of the invention pertains to methods of modulating PGC-1 expression or activity for therapeutic purposes. Accordingly, in an exemplary embodiment, the modulatory method of the invention involves contacting a cell capable of expressing PGC-1 with an agent that modulates one or more of the activities of PGC-1 protein activity associated with the cell, such that PGC-1 activity in the cell is modulated. An agent that modulates PGC-1 protein activity can be an agent as described herein, such as a nucleic acid or a protein, a naturally-occurring target molecule of a PGC-1 protein (e.g., a PGC-1 target molecule), a PGC-1 antibody, a PGC-1 agonist or antagonist, a peptidomimetic of a PGC-1 agonist or antagonist, or other small molecule. In one embodiment, the agent stimulates one or more PGC-1 activities. Examples of such stimulatory agents include active PGC-1 protein and a nucleic acid molecule encoding PGC-1 that has been introduced into the cell. In another embodiment, the agent inhibits one or more PGC-1 activities. Examples of such inhibitory agents include antisense PGC-1 nucleic acid molecules, anti-PGC-1 antibodies, and PGC-1 inhibitors. These modulatory methods can be performed in vitro (e.g., by culturing the cell with the agent) or, alternatively, in vivo (e.g. by administering the agent to a subject). As such, the present invention provides methods of treating an individual afflicted with a disease or disorder character by aberrant or unwanted expression or activity of a PGC-1 protein or nucleic acid molecule. In one embodiment, the method involves administering an agent (e.g., an agent identified by a screening assay described herein), or combination of agents that modulates (e.g., upregulates or downregulates) PGC-1 expression or activity. In another embodiment, the method involves administering a PGC-1 protein or nucleic acid molecule as therapy to compensate for reduced, aberrant, or unwanted PGC-1 expression or activity. Stimulation of PGC-1 activity is desirable in situations in which PGC-1 is abnormally downregulated and/or in which increased PGC-1 activity is likely to have a beneficial effect. For example, stimulation of PGC-1 activity is desirable in situations in which a PGC-1 is downregulated and/or in which increased PGC-1 activity is likely to have a beneficial effect. Likewise, inhibition of PGC-1 activity is desirable in situations in which PGC-1 is abnormally upregulated and/or in which decreased PGC-1 activity is likely to have a beneficial effect.

This invention is further illustrated by the following examples, which should not be construed as limiting. The contents of all references, patent applications, patents, and published patent applications, as well as the Figures and the Sequence Listing, cited throughout this application are hereby incorporated by reference.

EXAMPLES

Materials and Methods

Library Screening and cDNA Cloning

The PGC-1b and PGC-1c cDNAs were isolated by screening an oligo-dT primed cDNA λZAP library prepared from HIB-1B polyA+ mRNA. This library was screened using the 297 bp NheI-EcoRI fragment derived from the PGC-1a cDNA After three rounds of screening under low stringency (2×SSC, 0.5% SDS at 42° C.), the inserts of thirty-one positive clones were excised into pBluescript and sequenced by standard methods. Seven of the positive clones turned out to be one of two novel isoforms of PGC-1, referred to herein as PGC-1b and PGC-1c.

pEGFP-PGC-1b and pEGFP-PGC-1c were constructed by replacing the 1866 bp EcoRI-BamHI fragment of pEGFP-PGC-1a with an EcoRI-BamHI PCR fragment corresponding to nucleotide 643-1100 of the PGCI-1b cDNA (SEQ ID NO:6) or 620-973 of the PGC-1c cDNA (SEQ ID NO:12), respectively. The vector used was pEGFP-C1 (Clontech).

To construct adensviral vectors, PCR was used to introduce a BamHI restriction site upstream of the first ATG codon of the PGC-1a and PGC-1b cDNAs. Their respective full length cDNAs were then excised from the pEGFP vectors with BamHI and XbaI restriction enzymes and cloned into pShuttle-CMV cut with BglII and XbaI. The final adenoviral vectors were obtained by in vivo-recombination between the pShuttle-CMV-PGC-1a or pShuttleCMV-PGC-1b constructs and the adenovirus backbone, as described in He, T. et al. (1998) *Proc. Natl. Acad. Sci. USA* 95:2509-2514. Adenoviruses were produced in 293 cells and purified by double cesium chloride gradient as described in He et al. (1998) supra.

Cell Culture

C2C12 myoblast cells were maintained in subconfluent culture in DMEM supplemented with 10% fetal bovine serum (FBS (CellGro)). Differentiation into myotubes was induced when cells reached confluence by switching the culture to differentiation medium (DMEM containing 2% heat inactivated horse serum (Life Technologies)). Cells were refed with differentiation medium daily until complete differentiation was observed (typically by day 4). These cells were then infected overnight with purified adenoviruses at a multiplicity of infection (MOI) of 500. This MOI was sufficient to infect about 90% of the differentiated myotubes, as determined using GFP-expressing adenovirus.

Immunofluorescence $1\times10^6$ C2C12 myoblasts were seeded on glass coverslips in 6 well plates and transfected 18 hours later with 1 μg of expression vector encoding the indicated GFP fusion protein, using Fugene 6 as transfection reagent (Roche Molecular Biochemicals). 24 to 48 hours after transfection, cells were fixed in 4% paraformaldehyde, and the coverslips were mounted on glass slides and examined by epifluorescence. For catalase staining, cells were permeabilized after fixation with 0.1% Triton-X100 in PBS, blocked in 3% bovine serum albumin (BSA) for 30 minutes, and sequentially incubated with a sheep polyclonal antibody raised against human catalase (The Binding Site, Birmingham, U.K) for 1 h at 37° C. and a Texas-Red conjugated secondary antibody.

Respiration Measurements in Intact Cells

C2C12 myoblasts were seeded in 100 mm dishes, differentiated into myotubes for 4 days, and infected with the different adenoviruses at equivalent MOIs. Oxygen consumption was measured 48 hours post-infection as follows: cells were washed with PBS once, mechanically detached from the plates using a cell lifter, and centrifuged for 2min at 500×g, and resuspended in 0.75 ml of differentiation medium.

0.5 ml cell suspension was transferred to a 1 ml Clark-type oxygen electrode chamber (Rank Bros., Bottisham, Cambridge, U.K) maintained at 37° C. and calibrated with air-saturated differentiation medium. Basal respiration was measured immediately after transfer, for about 10 minutes. State 4 (non-phosphorylating) respiration was induced by addition of 320 ng/ml oligomycin (an inhibitor of mitochondrial ATPase and phosphoryl group transfer), and the rate measured after steady state oxygen consumption was reached. After another 10 minutes, 8 μM FCCP (carbonyl cyanide 4-trifluoromethoxyphenylhydrazone, an uncoupler of oxidative phosphorylation) was added to determine uncoupled respiration in the cells. All respiration rates were expressed relative to basal respiration as determined at the beginning of each experiment.

Northern Blotting

Infected C2C12 myotubes grown in 60 mm dishes were lysed in 1.5 ml of Trizol reagent (Life Technologies) and total RNA was purified according to the manufacturer's instructions. RNA were resolved on 1.2% agarose/formaldehyde gel before transfer to nylon membranes (ICN). Hybridization was performed in UltraHyb solution (Ambion) according to the manufacturer's instructions. Certain cDNA probes were described in Wu, Z. et al. (1999) *Cell* 98(1):115-24. The following mouse cDNA fragments were used as probes for northern blot analysis: Lipoprotein lipase (LPL; GenBank Accession No. J03302): 400 nucleotide fragment (the 400 nucleotides at the 3' end of the coding region);. FAT/CD36 (GenBank Accession No. L23108): 962 nucleotide fragment (nucleotides 686 to 1647); MCD (GenBank Accession No. BC004764): 696 nucleotide fragment (nucleotides 860 to 1555); VLACS (GenBank Accession No. AJ223958): 934 nucleotide fragment (nucleotides 864 to 1797). AOX was detected using a 1.4 kb fragment derived from the rat cDNA (GenBank Accession No. J02752). MCAD (GenBank Accession No. NM_007382) was detected using the full length cDNA fragment.

Example 1

Identification of Two Novel Isoforms of PGC-1

PCC-1a was previously identified in a yeast two-hybrid screen aimed at identifying brown fat specific PPARγ transcriptional co-activators (Puigserver, P. et al. (1998) *Cell* 92(6):829-39; U.S. Pat. No. 6,166,192; PCT International Publication No.

WO 98/54220). The nucleotide and amino acid sequences of PGC-1a are shown in SEQ ID NOs:1 and 2, respectively. The coding region of PGC-1a is shown in SEQ ID NO:3.

Two shorter PGC-1 have now been identified. These clones, referred to herein as PGC-1b and PGC-1c, contained inserts of 1893 and 1744 nucleotides, respectively (SEQ ID NO:6 and SEQ ID NO:12, respectively). PGC-1a, PGC-1b, and PGC-1c are identical through their 5' regions (except for a short region of nucleotides at the extreme 3' UTR of each isoform; see FIG. 6) but diverge after nucleotide 964 of PGC-1a (SEQ ID NO:1), corresponding to nucleotide 962 of PGC-1b (SEQ ID NO:6) and nucleotide 939 of PGC-1c (SEQ ID NO:12). See FIGS. 5 and 7. This corresponds to the junction between exon 7 and 8 of the human PGC-1a genomic sequence, suggesting that PGC-1b and PGC-1c could arise from alternative splicing. PGC-1b and PGC-1c contain predicted open reading frames of 960 and 900 nucleotides, respectively, and therefore lack the C-terminal SR and RRM RNA processing motifs identified in PGC-1a (Monsalve, M. et al. (2000) *Mol. Cell* 6(2):307-1.6). The proteins encoded by PGC-1b and PGC-1c are identical to the PGC-1a protein (SEQ ID:NO.2) through amino acid residues 1-291 of SEQ ID NO:7 (PGC-1b) and SEQ ID NO:13 (PGC-1c), but each contains a unique C-terminal region (see FIGS. 5 and 7).

Example 2

Expression Pattern of PGC-1b

To determine the expression pattern of PGC-1b, two oligonucleotides in the 3' region specific to PGC-1b were designed, and expression level of PGC-1b was determined by quantitative rt-PCR. The results of the rt-PCR analysis demonstrated that PGC-1b is highly expressed in heart and hypothalamus, with intermediate levels of expression found in kidney, skeletal muscle and brown fat. No signal could be detected in white fat or spleen. This pattern of expression closely overlaps the one described for PGC-1a (Puigserver, P. et al. (1998) *Cell* 92(6):829-39).

Example 3

PGC-1c dose not Promote Mitochondrial Biogenesis or Function

PGC-1a promotes mitochondrial biogenesis and respiration in C2C12 cells (Wu, Z. et al. (1999) *Cell* 98(1):115-24). In order to determine whether PGC-1b can also do so, C2C12 myoblasts (at day five of differentiation) were infected with adenoviruses expressing either GFP (as a control), PGC-1a, or PGC-1b. Oxygen consumption was measured 48 hours after infection. While PGC-1a stimulated both total and oligomycin-dependent respiration, as well as overall mitochondrial capacity (as assessed by the O2 consumption in the presence of the uncoupler FCCP), PGC-1b expression did not significantly affect any of these variables.

The effect of PGC-1a on mitochondrial respiration has been linked to its ability to induce components of the respiratory chain (B ATP synthetase, CytC, CoxII and CoxIV). In agreement with its lack of effect on mitochondrial respiration, PGC-1b did not stimulate the expression of any of the respiratory chain genes, nor did it induce the mRNA for mTFA or NRF-1, two key factors involved in mitochondrial biogenesis.

Since PGC-1a orchestrates mitochondrial biogenesis and the induction of several respiratory genes by co-activating NRF-1 (Wu, Z. et al. (1999) *Cell* 98(1):115-24), the ability of PGC-1b to co-activate this transcription factor in transient transfection was tested. However, despite the fact that PGC-1b contains the N-terminal transcription activation domain and most of the transcription factor interaction motifs present in PGC-1a (Puigserver, P. et al. (1999) *Science* 286(5443):1368-71), it failed to activate the NRF-1 reporter gene.

The fact that PGC-1b appears to be, based on the data above, an inactive variant of the full length PGC-1a, prompted an evaluation of whether it could act as a dominant negative regulator of PGC-1a. C2C12 myoblasts were infected with a constant MOI for PGC-1-a adenovirus and an increasing MOI of GFP (as a control) or PGC-1b viruses. Increasing the expression of PGC-1b did not prevent the induction of Cytochrome C, a direct target of the NRF-1/PGC-1a complex.

Taken together, these results demonstrate that PGC-1b does not influence mitochondrial biogenesis or function, either directly or through interference with PGC-1a, and suggest that PGC-1b has a specific function distinct from the role of PGC-1a.

Example 4

PGC-1b is Localized to Peroxisomes

The inability of PGC-1b to activate known PGC-1a target genes, despite the presence of both the N-terminal activation domain and most of the transcription factor interaction motifs prompted examination of its subcellular localization. A GFP-PGC-1b fusion protein was localized to the cytoplasm and showed a striking punctate pattern, in contrast with the nuclear and cytoplasmic localization observed for GFP-PGC-1a and GFP-PGC-1c, respectively. Because PGC-1b and PGC-1c differ only in their unique C-termini, it was hypothesized that the unique C-terminus of PGC-1b might dictate its punctate localization within the cytoplasm. To test this hypothesis directly, the C-terminal 29 amino acids of PGC-1b (the unique region, corresponding to amino acid residues 292-320 of SEQ ID NO:7, set forth as SEQ ID NO:10) were fused to GFP. The resulting fusion protein localized to cytoplasmic dots, demonstrating that these 29 amino acids are sufficient to direct the punctate localization of PGC-1b.

Analysis of the PGC-1b unique C-terminal domain revealed the presence of a carboxy-terminal tripeptide (at residues 318-320 of SEQ ID NO:7 and residues 27-29 of SEQ ID NO:10) resembling the peroxisomal localization signal found in the enzyme d-aspartate oxidase (Ser-Asn-Leu-COOH; Amery, L. et al. (1998) *Biochem. J.* 336(Pt. 2):367-71).

To determine if the punctate localization corresponded to peroxisomes, cells transfected with GFP-PGC-1b were stained with an antibody specific for the peroxisomal marker catalase. The results of this analysis indicated that the GFP-PGC-1b and catalase signals colocalized, demonstrating that PGC-1b is indeed targeted to peroxisomes. Finally, using an antibody specific for the amino-terminal region of PGC-1, the peroxisomal localization was confirmed with an non-tagged form of PGC-1b. This analysis further showed that PGC-1b remained localized to peroxisomes in fully differentiated C2C12 myotubes.

Example 5

PGC-1b Induces Genes Involved in Fatty-Acid Uptake and Oxidation

The peroxisomal localization of PGC-1b prompted examination of its potential involvement as a regulator of fatty-acid oxidation genes. The expression of PGC-1b in fully differentiated C2C12 myotubes induced a panel of key regulatory genes along the fatty-acid metabolic pathway: lipoprotein lipase (LPL), which hydrolyses the core triglycerides of circulating chylomicron; fatty acid translocase (FAT/CD36), which is part of a specialized, protein-facilitated membrane transport system for long chain fatty-acids; very long chain acyl-CoA synthetase (VLACS), a peroxisomal membrane protein involved in the import of very long chain fatty acids in peroxisomes; acyl Co-A oxidase (AOX), the rate limiting enzyme in peroxisomal fatty acid oxidation; medium chain acyl-CoA dehydrogenase (MCAD), which catalyzes a pivotal step in mitochondrial fatty acid oxidation; and malonyl-CoA dehydrogenase (MCD), whose action lowers the steady state level of malonyl-CoA, an allosteric inhibitor of carnitine palmitoyltransferase-1 (CPT-1), an enzyme which promotes fatty acid oxidation. Some of these genes were specifically induced by PGC-1b (LPL and AOX), while others were activated by both PGC-1b and PGC-1a (FAT/CD36, VLACS, MCD and MCAD).

Despite the role of PPARα in the induction of most of these genes in the liver, and the fact that PGC-1a coactivates PPARα (Vega, R. B. et al. (2000) *Mol. Cell. Biol.* 20(5): 1868-76), treatment with the PPARα ligand WY, even at saturating doses, did not result in any further stimulation of their expression. These results were confirmed in C2C12 myoblasts which overexpressed PPARα. Although treatment with WY ligand could induce some PPARα targets (e.g., UCP3), no cooperativity was observed between PGC-1b-mediated gene activation and PPARα, suggesting that in C2C12 cells, PGC-1b activates AOX and LPL in a PPARα independent manner.

Equivalents

Those skilled in the art will recognize, or be able to ascertain using no more than routine experimentation, many equivalents to the specific embodiments of the invention described herein Such equivalents are intended to be encompassed by the following claims.

What is claimed is:

1. An isolated nucleic acid molecule comprising the nucleotide sequence set forth in SEQ ID NO:6 or a full complement thereof.

2. An isolated nucleic acid molecule which encodes a polypeptide comprising the amino acid sequence set forth in SEQ ID NO:7 or a full complement thereof.

3. An isolated nucleic acid molecule selected from the group consisting of:
   a) a nucleic acid molecule comprising a nucleotide sequence which is at least 95% identical to the nucleotide sequence of SEQ ID NO:6 over the full length and
   b) a nucleic acid molecule which encodes a polypeptide comprising an amino acid sequence at least about 95% identical to the amino acid sequence of SEQ ID NO:7 over the full length,
   wherein the nucleic acid molecule encodes a polypeptide with the ability having one or more of the following biological activities: interaction with a nuclear receptor, UCP-2 expression, Acyl Co-A Oxidase expression, thermogenesis in adipose cells, differentiation of adipose cells, and insulin sensitivity of adipose cells.

4. The isolated nucleic acid molecule of claim 3, wherein the polypeptide comprises one or more of the following domains or motifs:
   a) a cAMP phosphorylation site;
   b) a tyrosine phosphorylation site; and
   c) an LXXLL motif.

5. An isolated nucleic acid molecule comprising the nucleic acid molecule of any one of claims 1, 2, 3, or 4, and a nucleotide sequence encoding a heterologous polypeptide.

6. A vector comprising the nucleic acid molecule of any one of claims 1, 2, 3, or 4.

7. The vector of claim 6, which is an expression vector.

8. An isolated host cell transfected with the expression vector of claim 7.

9. A method of producing a polypeptide comprising culturing the host cell of claim 8 in an appropriate culture medium to, thereby, produce the polypeptide.

10. An isolated polypeptide selected from the group consisting of:
    a) a polypeptide which is encoded by a nucleic acid molecule comprising a nucleotide sequence which is at least 60% identical to a nucleic acid molecule comprising the nucleotide sequence of SEQ ID NO:6 over the full length; and
    b) a polypeptide comprising an amino acid sequence which is at least 95% identical to the amino acid sequence of SEQ ID NO:7 over the full length,
    wherein the polypeptide maintains the ability of one or more of the following biological activities: interaction with a nuclear receptor, UCP-2 expression, Acyl Co-A Oxidase expression, thermogenesis in adipose cells, differentiation of adipose cells, and insulin sensitivity of adipose cells.

11. The isolated polypeptide of claim 10, wherein the polypeptide comprises one or more of the following domains or motifs:
    a) a cAMP phosphorylation site;
    b) a tyrosine phosphorylation site; and
    c) an LXXLL motif.

12. The isolated polypeptide of claim 10 comprising the amino acid sequence of SEQ ID NO:7.

13. The polypeptide of claim 10, further comprising heterologous amino acid sequences.

\* \* \* \* \*

SEQUENCE LISTING

```
<160> NUMBER OF SEQ ID NOS: 17

<210> SEQ ID NO 1
<211> LENGTH: 3066
<212> TYPE: DNA
<213> ORGANISM: Mus musculus
<220> FEATURE:
<221> NAME/KEY: CDS
<222> LOCATION: (92)...(2482)

<400> SEQUENCE: 1
aattcggcac gaggttgcct gcatgagtgt gtgctgtgtg tcagagtgga ttggagttga        60
aaaagcttga ctggcgtcat tcgggagctg g atg gct tgg gac atg tgc agc         112
                                   Met Ala Trp Asp Met Cys Ser
                                     1               5 caa gac tct gta tgg agt gac ata gag tgt gct gct ctg gtt ggt gag        160
Gln Asp Ser Val Trp Ser Asp Ile Glu Cys Ala Ala Leu Val Gly Glu
        10                  15                  20 gac cag cct ctt tgc cca gat ctt cct gaa ctt gac ctt tct gaa ctt        208
Asp Gln Pro Leu Cys Pro Asp Leu Pro Glu Leu Asp Leu Ser Glu Leu
    25                  30                  35 gat gtg aat gac ttg gat aca gac agc ttt ctg ggt gga ttg aag tgg        256
Asp Val Asn Asp Leu Asp Thr Asp Ser Phe Leu Gly Gly Leu Lys Trp
40                  45                  50                  55 tgt agc gac caa tcg gaa atc ata tcc aac cag tac aac aat gag cct        304
Cys Ser Asp Gln Ser Glu Ile Ile Ser Asn Gln Tyr Asn Asn Glu Pro
                60                  65                  70 gcg aac ata ttt gag aag ata gat gaa gag aat gag gca aac ttg cta        352
Ala Asn Ile Phe Glu Lys Ile Asp Glu Glu Asn Glu Ala Asn Leu Leu
            75                  80                  85 gcg gtc ctc aca gag aca ctg gac agt ctc ccc gtg gat gaa gac gga        400
Ala Val Leu Thr Glu Thr Leu Asp Ser Leu Pro Val Asp Glu Asp Gly
        90                  95                 100 ttg ccc tca ttt gat gca ctg aca gat gga gcc gtg acc act gac aac        448
Leu Pro Ser Phe Asp Ala Leu Thr Asp Gly Ala Val Thr Thr Asp Asn
   105                 110                 115 gag gcc agt cct tcc tcc atg cct gac ggc acc cct ccc cct cag gag        496
Glu Ala Ser Pro Ser Ser Met Pro Asp Gly Thr Pro Pro Pro Gln Glu
120                 125                 130                 135
```

-continued

| | | |
|---|---|---|
| gca gaa gag ccg tct cta ctt aag aag ctc tta ctg gca cca gcc aac<br>Ala Glu Glu Pro Ser Leu Leu Lys Lys Leu Leu Leu Ala Pro Ala Asn<br>140                        145                        150 | | 544 |
| act cag ctc agc tac aat gaa tgc agc ggt ctt agc act cag aac cat<br>Thr Gln Leu Ser Tyr Asn Glu Cys Ser Gly Leu Ser Thr Gln Asn His<br>          155                        160                        165 | | 592 |
| gca gca aac cac acc cac agg atc aga aca aac cct gcc att gtt aag<br>Ala Ala Asn His Thr His Arg Ile Arg Thr Asn Pro Ala Ile Val Lys<br>          170                        175                        180 | | 640 |
| acc gag aat tca tgg agc aat aaa gcg aag agc att tgt caa cag caa<br>Thr Glu Asn Ser Trp Ser Asn Lys Ala Lys Ser Ile Cys Gln Gln Gln<br>185                        190                        195 | | 688 |
| aag cca caa aga cgt ccc tgc tca gag ctt ctc aag tat ctg acc aca<br>Lys Pro Gln Arg Arg Pro Cys Ser Glu Leu Leu Lys Tyr Leu Thr Thr<br>200                        205                        210                        215 | | 736 |
| aac gat gac cct cct cac acc aaa ccc aca gaa aac agg aac agc agc<br>Asn Asp Asp Pro Pro His Thr Lys Pro Thr Glu Asn Arg Asn Ser Ser<br>          220                        225                        230 | | 784 |
| aga gac aaa tgt gct tcc aaa aag aag tcc cat aca caa ccg cag tcg<br>Arg Asp Lys Cys Ala Ser Lys Lys Lys Ser His Thr Gln Pro Gln Ser<br>               235                        240                        245 | | 832 |
| caa cat gct caa gcc aaa cca aca act tta tct ctt cct ctg acc cca<br>Gln His Ala Gln Ala Lys Pro Thr Thr Leu Ser Leu Pro Leu Thr Pro<br>250                        255                        260 | | 880 |
| gag tca cca aat gac ccc aag ggt tcc cca ttt gag aac aag act att<br>Glu Ser Pro Asn Asp Pro Lys Gly Ser Pro Phe Glu Asn Lys Thr Ile<br>          265                        270                        275 | | 928 |
| gag cga acc tta agt gtg gaa ctc tct gga act gca ggc cta act cct<br>Glu Arg Thr Leu Ser Val Glu Leu Ser Gly Thr Ala Gly Leu Thr Pro<br>280                        285                        290                        295 | | 976 |
| ccc aca act cct cct cat aaa gcc aac caa gat aac cct ttc aag gct<br>Pro Thr Thr Pro Pro His Lys Ala Asn Gln Asp Asn Pro Phe Lys Ala<br>               300                        305                        310 | | 1024 |
| tcg cca aag ctg aag ccc tct tgc aag acc gtg gtg cca ccg cca acc<br>Ser Pro Lys Leu Lys Pro Ser Cys Lys Thr Val Val Pro Pro Pro Thr<br>          315                        320                        325 | | 1072 |
| aag agg gcc cgg tac agt gag tgt tct ggt acc caa ggc agc cac tcc<br>Lys Arg Ala Arg Tyr Ser Glu Cys Ser Gly Thr Gln Gly Ser His Ser<br>330                        335                        340 | | 1120 |
| acc aag aaa ggg ccc gag caa tct gag ttg tac gca caa ctc agc aag<br>Thr Lys Lys Gly Pro Glu Gln Ser Glu Leu Tyr Ala Gln Leu Ser Lys<br>          345                        350                        355 | | 1168 |
| tcc tca ggg ctc agc cga gga cac gag gaa agg aag act aaa cgg ccc<br>Ser Ser Gly Leu Ser Arg Gly His Glu Glu Arg Lys Thr Lys Arg Pro<br>360                        365                        370                        375 | | 1216 |
| agt ctc cgg ctg ttt ggt gac cat gac tac tgt cag tca ctc aat tcc<br>Ser Leu Arg Leu Phe Gly Asp His Asp Tyr Cys Gln Ser Leu Asn Ser<br>               380                        385                        390 | | 1264 |
| aaa acg gat ata ctc att aac ata tca cag gag ctc caa gac tct aga<br>Lys Thr Asp Ile Leu Ile Asn Ile Ser Gln Glu Leu Gln Asp Ser Arg<br>          395                        400                        405 | | 1312 |
| caa cta gac ttc aaa gat gcc tcc tgt gac tgg cag ggg cac atc tgt<br>Gln Leu Asp Phe Lys Asp Ala Ser Cys Asp Trp Gln Gly His Ile Cys<br>410                        415                        420 | | 1360 |
| tct tcc aca gat tca ggc cag tgc tac ctg aga gag act ttg gag gcc<br>Ser Ser Thr Asp Ser Gly Gln Cys Tyr Leu Arg Glu Thr Leu Glu Ala<br>          425                        430                        435 | | 1408 |
| agc aag cag gtc tct cct tgc agc acc aga aaa cag ctc caa gac cag<br>Ser Lys Gln Val Ser Pro Cys Ser Thr Arg Lys Gln Leu Gln Asp Gln<br>440                        445                        450                        455 | | 1456 |

```
                                                      -continued gaa atc cga gcg gag ctg aac aag cac ttc ggt cat ccc tgt caa gct    1504
Glu Ile Arg Ala Glu Leu Asn Lys His Phe Gly His Pro Cys Gln Ala
            460                 465                 470 gtg ttt gac gac aaa tca gac aag acc agt gaa cta agg gat ggc gac    1552
Val Phe Asp Asp Lys Ser Asp Lys Thr Ser Glu Leu Arg Asp Gly Asp
    475                 480                 485 ttc agt aat gaa caa ttc tcc aaa cta cct gtg ttt ata aat tca gga    1600
Phe Ser Asn Glu Gln Phe Ser Lys Leu Pro Val Phe Ile Asn Ser Gly
490                 495                 500 cta gcc atg gat ggc cta ttt gat gac agt gaa gat gaa agt gat aaa    1648
Leu Ala Met Asp Gly Leu Phe Asp Asp Ser Glu Asp Glu Ser Asp Lys
        505                 510                 515 ctg agc tac cct tgg gat ggc acg cag ccc tat tca ttg ttc gat gtg    1696
Leu Ser Tyr Pro Trp Asp Gly Thr Gln Pro Tyr Ser Leu Phe Asp Val
520                 525                 530                 535 tcg cct tct tgc tct tcc ttt aac tct ccg tgt cga gac tca gtg tca    1744
Ser Pro Ser Cys Ser Ser Phe Asn Ser Pro Cys Arg Asp Ser Val Ser
            540                 545                 550 cca ccg aaa tcc tta ttt tct caa aga ccc caa agg atg cgc tct cgt    1792
Pro Pro Lys Ser Leu Phe Ser Gln Arg Pro Gln Arg Met Arg Ser Arg
    555                 560                 565 tca aga tcc ttt tct cga cac agg tcg tgt tcc cga tca cca tat tcc    1840
Ser Arg Ser Phe Ser Arg His Arg Ser Cys Ser Arg Ser Pro Tyr Ser
570                 575                 580 agg tca aga tca agg tcc cca ggc agt aga tcc tct tca aga tcc tgt    1888
Arg Ser Arg Ser Arg Ser Pro Gly Ser Arg Ser Ser Ser Arg Ser Cys
        585                 590                 595 tac tac tat gaa tca agc cac tac aga cac cgc aca cac cgc aat tct    1936
Tyr Tyr Tyr Glu Ser Ser His Tyr Arg His Arg Thr His Arg Asn Ser
600                 605                 610                 615 ccc ttg tat gtg aga tca cgt tca agg tca ccc tac agc cgt agg ccc    1984
Pro Leu Tyr Val Arg Ser Arg Ser Arg Ser Pro Tyr Ser Arg Arg Pro
            620                 625                 630 agg tac gac agc tat gaa gcc tat gag cac gaa agg ctc aag agg gat    2032
Arg Tyr Asp Ser Tyr Glu Ala Tyr Glu His Glu Arg Leu Lys Arg Asp
    635                 640                 645 gaa tac cgc aaa gag cac gag aag cgg gag tct gaa agg gcc aaa cag    2080
Glu Tyr Arg Lys Glu His Glu Lys Arg Glu Ser Glu Arg Ala Lys Gln
650                 655                 660 aga gag agg cag aag cag aaa gca att gaa gag cgc cgt gtg att tac    2128
Arg Glu Arg Gln Lys Gln Lys Ala Ile Glu Glu Arg Arg Val Ile Tyr
        665                 670                 675 gtt ggt aaa atc aga cct gac aca acg cgg aca gaa ttg aga gac cgc    2176
Val Gly Lys Ile Arg Pro Asp Thr Thr Arg Thr Glu Leu Arg Asp Arg
680                 685                 690                 695 ttt gaa gtt ttt ggt gaa att gag gaa tgc acc gta aat ctg cgg gat    2224
Phe Glu Val Phe Gly Glu Ile Glu Glu Cys Thr Val Asn Leu Arg Asp
            700                 705                 710 gat gga gac agc tat ggt ttc atc acc tac cgt tac acc tgt gac gct    2272
Asp Gly Asp Ser Tyr Gly Phe Ile Thr Tyr Arg Tyr Thr Cys Asp Ala
    715                 720                 725 ttc gct gct ctt gag aat gga tat act tta cgc agg tcg aac gaa act    2320
Phe Ala Ala Leu Glu Asn Gly Tyr Thr Leu Arg Arg Ser Asn Glu Thr
730                 735                 740 gac ttc gag ctg tac ttt tgt gga cgg aag caa ttt ttc aag tct aac    2368
Asp Phe Glu Leu Tyr Phe Cys Gly Arg Lys Gln Phe Phe Lys Ser Asn
        745                 750                 755 tat gca gac cta gat acc aac tca gac gat ttt gac cct gct tcc acc    2416
Tyr Ala Asp Leu Asp Thr Asn Ser Asp Asp Phe Asp Pro Ala Ser Thr
```

-continued

```
                760              765              770             775
aag agc aag tat gac tct ctg gat ttt gat agt tta ctg aag gaa gct      2464
Lys Ser Lys Tyr Asp Ser Leu Asp Phe Asp Ser Leu Leu Lys Glu Ala
                780                      785                  790 cag aga agc ttg cgc agg taacgtgttc ccaggctgag gaatgacaga              2512
Gln Arg Ser Leu Arg Arg
                795 gagatggtca atacctcatg ggacagcgtg tcctttccca agactcttgc aagtcatact     2572 taggaatttc tcctacttta cactctctgt acaaaaataa acaaaacaa aacaacaata      2632 acaacaacaa caacaacaat aacaacaaca accataccag aacaagaaca acggtttaca    2692 tgaacacagc tgctgaagag gcaagagaca gaatgataat ccagtaagca cacgtttatt    2752 cacgggtgtc agctttgctt tccctggagg ctcttggtga cagtgtgtgt gcgtgtgtgt    2812 gtgtgggtgt gcgtgtgtgt atgtgtgtgt gtgtacttgt ttggaaagta catatgtaca    2872 catgtgagga cttgggggca cctgaacaga acgaacaagg gcgacccctt caaatggcag    2932 catttccatg aagacacact taaaacctac aacttcaaaa tgttcgtatt ctatacaaaa    2992 ggaaaataaa taaatataaa aaaaaaaaaa aaaaactcg agagatctat gaatcgtaga     3052 tactgaaaaa cccc                                                      3066
```

<210> SEQ ID NO 2
<211> LENGTH: 797
<212> TYPE: PRT
<213> ORGANISM: Mus musculus

<400> SEQUENCE: 2

```
Met Ala Trp Asp Met Cys Ser Gln Asp Ser Val Trp Ser Asp Ile Glu
1               5                   10                  15

Cys Ala Ala Leu Val Gly Glu Asp Gln Pro Leu Cys Pro Asp Leu Pro
            20                  25                  30

Glu Leu Asp Leu Ser Glu Leu Asp Val Asn Asp Leu Asp Thr Asp Ser
        35                  40                  45

Phe Leu Gly Gly Leu Lys Trp Cys Ser Asp Gln Ser Glu Ile Ile Ser
    50                  55                  60

Asn Gln Tyr Asn Asn Glu Pro Ala Asn Ile Phe Glu Lys Ile Asp Glu
65                  70                  75                  80

Glu Asn Glu Ala Asn Leu Leu Ala Val Leu Thr Glu Thr Leu Asp Ser
                85                  90                  95

Leu Pro Val Asp Glu Asp Gly Leu Pro Ser Phe Asp Ala Leu Thr Asp
            100                 105                 110

Gly Ala Val Thr Thr Asp Asn Glu Ala Ser Pro Ser Ser Met Pro Asp
        115                 120                 125

Gly Thr Pro Pro Pro Gln Glu Ala Glu Glu Pro Ser Leu Leu Lys Lys
    130                 135                 140

Leu Leu Leu Ala Pro Ala Asn Thr Gln Leu Ser Tyr Asn Glu Cys Ser
145                 150                 155                 160

Gly Leu Ser Thr Gln Asn His Ala Ala Asn His Thr His Arg Ile Arg
                165                 170                 175

Thr Asn Pro Ala Ile Val Lys Thr Glu Asn Ser Trp Ser Asn Lys Ala
            180                 185                 190

Lys Ser Ile Cys Gln Gln Gln Lys Pro Gln Arg Arg Pro Cys Ser Glu
        195                 200                 205

Leu Leu Lys Tyr Leu Thr Thr Asn Asp Asp Pro Pro His Thr Lys Pro
    210                 215                 220
```

-continued

```
Thr Glu Asn Arg Asn Ser Ser Arg Asp Lys Cys Ala Ser Lys Lys
225                 230                 235                 240

Ser His Thr Gln Pro Gln Ser Gln His Ala Gln Ala Lys Pro Thr Thr
            245                 250                 255

Leu Ser Leu Pro Leu Thr Pro Glu Ser Pro Asn Asp Pro Lys Gly Ser
                260                 265                 270

Pro Phe Glu Asn Lys Thr Ile Glu Arg Thr Leu Ser Val Glu Leu Ser
            275                 280                 285

Gly Thr Ala Gly Leu Thr Pro Pro Thr Thr Pro Pro His Lys Ala Asn
290                 295                 300

Gln Asp Asn Pro Phe Lys Ala Ser Pro Lys Leu Lys Pro Ser Cys Lys
305                 310                 315                 320

Thr Val Val Pro Pro Thr Lys Arg Ala Arg Tyr Ser Glu Cys Ser
                325                 330                 335

Gly Thr Gln Gly Ser His Ser Thr Lys Lys Gly Pro Glu Gln Ser Glu
            340                 345                 350

Leu Tyr Ala Gln Leu Ser Lys Ser Ser Gly Leu Ser Arg Gly His Glu
            355                 360                 365

Glu Arg Lys Thr Lys Arg Pro Ser Leu Arg Leu Phe Gly Asp His Asp
370                 375                 380

Tyr Cys Gln Ser Leu Asn Ser Lys Thr Asp Ile Leu Ile Asn Ile Ser
385                 390                 395                 400

Gln Glu Leu Gln Asp Ser Arg Gln Leu Asp Phe Lys Asp Ala Ser Cys
            405                 410                 415

Asp Trp Gln Gly His Ile Cys Ser Ser Thr Asp Ser Gly Gln Cys Tyr
            420                 425                 430

Leu Arg Glu Thr Leu Glu Ala Ser Lys Gln Val Ser Pro Cys Ser Thr
            435                 440                 445

Arg Lys Gln Leu Gln Asp Gln Glu Ile Arg Ala Glu Leu Asn Lys His
450                 455                 460

Phe Gly His Pro Cys Gln Ala Val Phe Asp Asp Lys Ser Asp Lys Thr
465                 470                 475                 480

Ser Glu Leu Arg Asp Gly Asp Phe Ser Asn Glu Gln Phe Ser Lys Leu
            485                 490                 495

Pro Val Phe Ile Asn Ser Gly Leu Ala Met Asp Gly Leu Phe Asp Asp
            500                 505                 510

Ser Glu Asp Glu Ser Asp Lys Leu Ser Tyr Pro Trp Asp Gly Thr Gln
            515                 520                 525

Pro Tyr Ser Leu Phe Asp Val Ser Pro Ser Cys Ser Ser Phe Asn Ser
            530                 535                 540

Pro Cys Arg Asp Ser Val Ser Pro Pro Lys Ser Leu Phe Ser Gln Arg
545                 550                 555                 560

Pro Gln Arg Met Arg Ser Arg Ser Arg Ser Phe Ser Arg His Arg Ser
            565                 570                 575

Cys Ser Arg Ser Pro Tyr Ser Arg Ser Arg Ser Arg Ser Pro Gly Ser
            580                 585                 590

Arg Ser Ser Ser Arg Ser Cys Tyr Tyr Tyr Glu Ser Ser His Tyr Arg
            595                 600                 605

His Arg Thr His Arg Asn Ser Pro Leu Tyr Val Arg Ser Arg Ser Arg
            610                 615                 620

Ser Pro Tyr Ser Arg Arg Pro Arg Tyr Asp Ser Tyr Glu Ala Tyr Glu
625                 630                 635                 640
```

-continued

```
His Glu Arg Leu Lys Arg Asp Glu Tyr Arg Lys Glu His Lys Arg
                645                 650                 655

Glu Ser Glu Arg Ala Lys Gln Arg Glu Arg Gln Lys Gln Lys Ala Ile
            660                 665                 670

Glu Glu Arg Arg Val Ile Tyr Val Gly Lys Ile Arg Pro Asp Thr Thr
        675                 680                 685

Arg Thr Glu Leu Arg Asp Arg Phe Glu Val Phe Gly Glu Ile Glu Glu
    690                 695                 700

Cys Thr Val Asn Leu Arg Asp Asp Gly Asp Ser Tyr Gly Phe Ile Thr
705                 710                 715                 720

Tyr Arg Tyr Thr Cys Asp Ala Phe Ala Ala Leu Glu Asn Gly Tyr Thr
                725                 730                 735

Leu Arg Arg Ser Asn Glu Thr Asp Phe Glu Leu Tyr Phe Cys Gly Arg
            740                 745                 750

Lys Gln Phe Phe Lys Ser Asn Tyr Ala Asp Leu Asp Thr Asn Ser Asp
        755                 760                 765

Asp Phe Asp Pro Ala Ser Thr Lys Ser Lys Tyr Asp Ser Leu Asp Phe
    770                 775                 780

Asp Ser Leu Leu Lys Glu Ala Gln Arg Ser Leu Arg Arg
785                 790                 795

<210> SEQ ID NO 3
<211> LENGTH: 2391
<212> TYPE: DNA
<213> ORGANISM: Mus musculus
<220> FEATURE:
<221> NAME/KEY: CDS
<222> LOCATION: (1)...(2391)

<400> SEQUENCE: 3 atg gct tgg gac atg tgc agc caa gac tct gta tgg agt gac ata gag     48
Met Ala Trp Asp Met Cys Ser Gln Asp Ser Val Trp Ser Asp Ile Glu
1               5                   10                  15 tgt gct gct ctg gtt ggt gag gac cag cct ctt tgc cca gat ctt cct     96
Cys Ala Ala Leu Val Gly Glu Asp Gln Pro Leu Cys Pro Asp Leu Pro
            20                  25                  30 gaa ctt gac ctt tct gaa ctt gat gtg aat gac ttg gat aca gac agc    144
Glu Leu Asp Leu Ser Glu Leu Asp Val Asn Asp Leu Asp Thr Asp Ser
        35                  40                  45 ttt ctg ggt gga ttg aag tgg tgt agc gac caa tcg gaa atc ata tcc    192
Phe Leu Gly Gly Leu Lys Trp Cys Ser Asp Gln Ser Glu Ile Ile Ser
    50                  55                  60 aac cag tac aac aat gag cct gcg aac ata ttt gag aag ata gat gaa    240
Asn Gln Tyr Asn Asn Glu Pro Ala Asn Ile Phe Glu Lys Ile Asp Glu
65                  70                  75                  80 gag aat gag gca aac ttg cta gcg gtc ctc aca gag aca ctg gac agt    288
Glu Asn Glu Ala Asn Leu Leu Ala Val Leu Thr Glu Thr Leu Asp Ser
                85                  90                  95 ctc ccc gtg gat gaa gac gga ttg ccc tca ttt gat gca ctg aca gat    336
Leu Pro Val Asp Glu Asp Gly Leu Pro Ser Phe Asp Ala Leu Thr Asp
            100                 105                 110 gga gcc gtg acc act gac aac gag gcc agt cct tcc tcc atg cct gac    384
Gly Ala Val Thr Thr Asp Asn Glu Ala Ser Pro Ser Ser Met Pro Asp
        115                 120                 125 ggc acc cct ccc cct cag gag gca gaa gag ccg tct cta ctt aag aag    432
Gly Thr Pro Pro Pro Gln Glu Ala Glu Glu Pro Ser Leu Leu Lys Lys
    130                 135                 140 ctc tta ctg gca cca gcc aac act cag ctc agc tac aat gaa tgc agc    480
Leu Leu Leu Ala Pro Ala Asn Thr Gln Leu Ser Tyr Asn Glu Cys Ser
```

-continued

```
                145                 150                 155                 160
ggt ctt agc act cag aac cat gca gca aac cac acc cac agg atc aga       528
Gly Leu Ser Thr Gln Asn His Ala Ala Asn His Thr His Arg Ile Arg
            165                 170                 175 aca aac cct gcc att gtt aag acc gag aat tca tgg agc aat aaa gcg       576
Thr Asn Pro Ala Ile Val Lys Thr Glu Asn Ser Trp Ser Asn Lys Ala
        180                 185                 190 aag agc att tgt caa cag caa aag cca caa aga cgt ccc tgc tca gag       624
Lys Ser Ile Cys Gln Gln Gln Lys Pro Gln Arg Arg Pro Cys Ser Glu
    195                 200                 205 ctt ctc aag tat ctg acc aca aac gat gac cct cct cac acc aaa ccc       672
Leu Leu Lys Tyr Leu Thr Thr Asn Asp Asp Pro Pro His Thr Lys Pro
210                 215                 220 aca gaa aac agg aac agc agc aga gac aaa tgt gct tcc aaa aag aag       720
Thr Glu Asn Arg Asn Ser Ser Arg Asp Lys Cys Ala Ser Lys Lys Lys
225                 230                 235                 240 tcc cat aca caa ccg cag tcg caa cat gct caa gcc aaa cca aca act       768
Ser His Thr Gln Pro Gln Ser Gln His Ala Gln Ala Lys Pro Thr Thr
            245                 250                 255 tta tct ctt cct ctg acc cca gag tca cca aat gac ccc aag ggt tcc       816
Leu Ser Leu Pro Leu Thr Pro Glu Ser Pro Asn Asp Pro Lys Gly Ser
        260                 265                 270 cca ttt gag aac aag act att gag cga acc tta agt gtg gaa ctc tct       864
Pro Phe Glu Asn Lys Thr Ile Glu Arg Thr Leu Ser Val Glu Leu Ser
    275                 280                 285 gga act gca ggc cta act cct ccc aca act cct cct cat aaa gcc aac       912
Gly Thr Ala Gly Leu Thr Pro Pro Thr Thr Pro Pro His Lys Ala Asn
290                 295                 300 caa gat aac cct ttc aag gct tcg cca aag ctg aag ccc tct tgc aag       960
Gln Asp Asn Pro Phe Lys Ala Ser Pro Lys Leu Lys Pro Ser Cys Lys
305                 310                 315                 320 acc gtg gtg cca ccg cca acc aag agg gcc cgg tac agt gag tgt tct      1008
Thr Val Val Pro Pro Pro Thr Lys Arg Ala Arg Tyr Ser Glu Cys Ser
            325                 330                 335 ggt acc caa ggc agc cac tcc acc aag aaa ggg ccc gag caa tct gag      1056
Gly Thr Gln Gly Ser His Ser Thr Lys Lys Gly Pro Glu Gln Ser Glu
        340                 345                 350 ttg tac gca caa ctc agc aag tcc tca ggg ctc agc cga gga cac gag      1104
Leu Tyr Ala Gln Leu Ser Lys Ser Ser Gly Leu Ser Arg Gly His Glu
    355                 360                 365 gaa agg aag act aaa cgg ccc agt ctc cgg ctg ttt ggt gac cat gac      1152
Glu Arg Lys Thr Lys Arg Pro Ser Leu Arg Leu Phe Gly Asp His Asp
370                 375                 380 tac tgt cag tca ctc aat tcc aaa acg gat ata ctc att aac ata tca      1200
Tyr Cys Gln Ser Leu Asn Ser Lys Thr Asp Ile Leu Ile Asn Ile Ser
385                 390                 395                 400 cag gag ctc caa gac tct aga caa cta gac ttc aaa gat gcc tcc tgt      1248
Gln Glu Leu Gln Asp Ser Arg Gln Leu Asp Phe Lys Asp Ala Ser Cys
            405                 410                 415 gac tgg cag ggg cac atc tgt tct tcc aca gat tca ggc cag tgc tac      1296
Asp Trp Gln Gly His Ile Cys Ser Ser Thr Asp Ser Gly Gln Cys Tyr
        420                 425                 430 ctg aga gag act ttg gag gcc agc aag cag gtc tct cct tgc agc acc      1344
Leu Arg Glu Thr Leu Glu Ala Ser Lys Gln Val Ser Pro Cys Ser Thr
    435                 440                 445 aga aaa cag ctc caa gac cag gaa atc cga gcg gag ctg aac aag cac      1392
Arg Lys Gln Leu Gln Asp Gln Glu Ile Arg Ala Glu Leu Asn Lys His
450                 455                 460 ttc ggt cat ccc tgt caa gct gtg ttt gac gac aaa tca gac aag acc      1440
```

```
Phe Gly His Pro Cys Gln Ala Val Phe Asp Asp Lys Ser Asp Lys Thr
465                 470                 475                 480 agt gaa cta agg gat ggc gac ttc agt aat gaa caa ttc tcc aaa cta      1488
Ser Glu Leu Arg Asp Gly Asp Phe Ser Asn Glu Gln Phe Ser Lys Leu
                    485                 490                 495 cct gtg ttt ata aat tca gga cta gcc atg gat ggc cta ttt gat gac      1536
Pro Val Phe Ile Asn Ser Gly Leu Ala Met Asp Gly Leu Phe Asp Asp
                500                 505                 510 agt gaa gat gaa agt gat aaa ctg agc tac cct tgg gat ggc acg cag      1584
Ser Glu Asp Glu Ser Asp Lys Leu Ser Tyr Pro Trp Asp Gly Thr Gln
            515                 520                 525 ccc tat tca ttg ttc gat gtg tcg cct tct tgc tct tcc ttt aac tct      1632
Pro Tyr Ser Leu Phe Asp Val Ser Pro Ser Cys Ser Ser Phe Asn Ser
        530                 535                 540 ccg tgt cga gac tca gtg tca cca ccg aaa tcc tta ttt tct caa aga      1680
Pro Cys Arg Asp Ser Val Ser Pro Pro Lys Ser Leu Phe Ser Gln Arg
545                 550                 555                 560 ccc caa agg atg cgc tct cgt tca aga tcc ttt tct cga cac agg tcg      1728
Pro Gln Arg Met Arg Ser Arg Ser Arg Ser Phe Ser Arg His Arg Ser
                565                 570                 575 tgt tcc cga tca cca tat tcc agg tca aga tca agg tcc cca ggc agt      1776
Cys Ser Arg Ser Pro Tyr Ser Arg Ser Arg Ser Arg Ser Pro Gly Ser
                580                 585                 590 aga tcc tct tca aga tcc tgt tac tac tat gaa tca agc cac tac aga      1824
Arg Ser Ser Ser Arg Ser Cys Tyr Tyr Tyr Glu Ser Ser His Tyr Arg
            595                 600                 605 cac cgc aca cac cgc aat tct ccc ttg tat gtg aga tca cgt tca agg      1872
His Arg Thr His Arg Asn Ser Pro Leu Tyr Val Arg Ser Arg Ser Arg
        610                 615                 620 tca ccc tac agc cgt agg ccc agg tac gac agc tat gaa gcc tat gag      1920
Ser Pro Tyr Ser Arg Arg Pro Arg Tyr Asp Ser Tyr Glu Ala Tyr Glu
625                 630                 635                 640 cac gaa agg ctc aag agg gat gaa tac cgc aaa gag cac gag aag cgg      1968
His Glu Arg Leu Lys Arg Asp Glu Tyr Arg Lys Glu His Glu Lys Arg
                645                 650                 655 gag tct gaa agg gcc aaa cag aga gag agg cag aag cag aaa gca att      2016
Glu Ser Glu Arg Ala Lys Gln Arg Glu Arg Gln Lys Gln Lys Ala Ile
                660                 665                 670 gaa gag cgc cgt gtg att tac gtt ggt aaa atc aga cct gac aca acg      2064
Glu Glu Arg Arg Val Ile Tyr Val Gly Lys Ile Arg Pro Asp Thr Thr
            675                 680                 685 cgg aca gaa ttg aga gac cgc ttt gaa gtt ttt ggt gaa att gag gaa      2112
Arg Thr Glu Leu Arg Asp Arg Phe Glu Val Phe Gly Glu Ile Glu Glu
        690                 695                 700 tgc acc gta aat ctg cgg gat gat gga gac agc tat ggt ttc atc acc      2160
Cys Thr Val Asn Leu Arg Asp Asp Gly Asp Ser Tyr Gly Phe Ile Thr
705                 710                 715                 720 tac cgt tac acc tgt gac gct ttc gct gct ctt gag aat gga tat act      2208
Tyr Arg Tyr Thr Cys Asp Ala Phe Ala Ala Leu Glu Asn Gly Tyr Thr
                725                 730                 735 tta cgc agg tcg aac gaa act gac ttc gag ctg tac ttt tgt gga cgg      2256
Leu Arg Arg Ser Asn Glu Thr Asp Phe Glu Leu Tyr Phe Cys Gly Arg
                740                 745                 750 aag caa ttt ttc aag tct aac tat gca gac cta gat acc aac tca gac      2304
Lys Gln Phe Phe Lys Ser Asn Tyr Ala Asp Leu Asp Thr Asn Ser Asp
            755                 760                 765 gat ttt gac cct gct tcc acc aag agc aag tat gac tct ctg gat ttt      2352
Asp Phe Asp Pro Ala Ser Thr Lys Ser Lys Tyr Asp Ser Leu Asp Phe
        770                 775                 780
```

| gat | agt | tta | ctg | aag | gaa | gct | cag | aga | agc | ttg | cgc | agg | 2391 |
|---|---|---|---|---|---|---|---|---|---|---|---|---|---|
| Asp | Ser | Leu | Leu | Lys | Glu | Ala | Gln | Arg | Ser | Leu | Arg | Arg | |
| 785 | | | | 790 | | | | | 795 | | | | |

<210> SEQ ID NO 4
<211> LENGTH: 924
<212> TYPE: DNA
<213> ORGANISM: Mus musculus

<400> SEQUENCE: 4

| tcagagtgga | ttggagttga | aaaagcttga | ctggcgtcat | tcgggagctg | atggcttgg | 60 |
|---|---|---|---|---|---|---|
| gacatgtgca | gccaagactc | tgtatggagt | gacatagagt | gtgctgctct | ggttggtgag | 120 |
| gaccagcctc | tttgcccaga | tcttcctgaa | cttgaccttt | ctgaacttga | tgtgaatgac | 180 |
| ttggatacag | acagctttct | gggtggattg | aagtggtgta | gcgaccaatc | ggaaatcata | 240 |
| tccaaccagt | acaacaatga | gcctgcgaac | atatttgaga | agatagatga | agagaatgag | 300 |
| gcgaacttgc | tagcggtcct | cacagagaca | ctggacagtc | tccccgtgga | tgaagacgga | 360 |
| ttgccctcat | tgatgcact | gacagatgga | gccgtgacca | ctgacaacga | ggccagtcct | 420 |
| tcctccatgc | ctgacggcac | ccctcccct | caggaggcag | aagagccgtc | tctacttaag | 480 |
| aagctcttac | tggcaccagc | caacactcag | ctcagctaca | atgaatgcag | cggtcttagc | 540 |
| actcagaacc | atgcagcaaa | ccacaccac | aggatcagaa | caaaccctgc | cattgttaag | 600 |
| accgagaatt | catggagcaa | taaagcgaag | agcatttgtc | aacagcaaaa | gccacaaaga | 660 |
| cgtccctgct | cagagcttct | caagtatctg | accacaaacg | atgaccctcc | tcacaccaaa | 720 |
| cccacagaaa | acaggaacag | cagcagagac | aaatgtgctt | ccaaaaagaa | gtcccataca | 780 |
| caaccgcagt | cgcaacatgc | tcaagccaaa | ccaacaactt | tatctcttcc | tctgacccca | 840 |
| gagtcaccaa | atgaccccaa | gggttcccca | tttgagaaca | agactattga | gcgaacctta | 900 |
| agtgtggaac | tctctggaac | tgca | | | | 924 |

<210> SEQ ID NO 5
<211> LENGTH: 291
<212> TYPE: PRT
<213> ORGANISM: Mus musculus

<400> SEQUENCE: 5

| Met | Ala | Trp | Asp | Met | Cys | Ser | Gln | Asp | Ser | Val | Trp | Ser | Asp | Ile | Glu |
|---|---|---|---|---|---|---|---|---|---|---|---|---|---|---|---|
| 1 | | | | 5 | | | | | 10 | | | | | 15 | |

| Cys | Ala | Ala | Leu | Val | Gly | Glu | Asp | Gln | Pro | Leu | Cys | Pro | Asp | Leu | Pro |
|---|---|---|---|---|---|---|---|---|---|---|---|---|---|---|---|
| | | | 20 | | | | | 25 | | | | | 30 | | |

| Glu | Leu | Asp | Leu | Ser | Glu | Leu | Asp | Val | Asn | Asp | Leu | Asp | Thr | Asp | Ser |
|---|---|---|---|---|---|---|---|---|---|---|---|---|---|---|---|
| | | | 35 | | | | | 40 | | | | | 45 | | |

| Phe | Leu | Gly | Gly | Leu | Lys | Trp | Cys | Ser | Asp | Gln | Ser | Glu | Ile | Ile | Ser |
|---|---|---|---|---|---|---|---|---|---|---|---|---|---|---|---|
| | 50 | | | | | 55 | | | | | 60 | | | | |

| Asn | Gln | Tyr | Asn | Asn | Glu | Pro | Ala | Asn | Ile | Phe | Glu | Lys | Ile | Asp | Glu |
|---|---|---|---|---|---|---|---|---|---|---|---|---|---|---|---|
| 65 | | | | | 70 | | | | | 75 | | | | | 80 |

| Glu | Asn | Glu | Ala | Asn | Leu | Leu | Ala | Val | Leu | Thr | Glu | Thr | Leu | Asp | Ser |
|---|---|---|---|---|---|---|---|---|---|---|---|---|---|---|---|
| | | | | 85 | | | | | 90 | | | | | 95 | |

| Leu | Pro | Val | Asp | Glu | Asp | Gly | Leu | Pro | Ser | Phe | Asp | Ala | Leu | Thr | Asp |
|---|---|---|---|---|---|---|---|---|---|---|---|---|---|---|---|
| | | | 100 | | | | | 105 | | | | | 110 | | |

| Gly | Ala | Val | Thr | Thr | Asp | Asn | Glu | Ala | Ser | Pro | Ser | Ser | Met | Pro | Asp |
|---|---|---|---|---|---|---|---|---|---|---|---|---|---|---|---|
| | | | 115 | | | | | 120 | | | | | 125 | | |

| Gly | Thr | Pro | Pro | Pro | Gln | Glu | Ala | Glu | Glu | Pro | Ser | Leu | Leu | Lys | Lys |
|---|---|---|---|---|---|---|---|---|---|---|---|---|---|---|---|
| | 130 | | | | | 135 | | | | | 140 | | | | |

```
Leu Leu Leu Ala Pro Ala Asn Thr Gln Leu Ser Tyr Asn Glu Cys Ser
145                 150                 155                 160

Gly Leu Ser Thr Gln Asn His Ala Ala Asn His Thr His Arg Ile Arg
                165                 170                 175

Thr Asn Pro Ala Ile Val Lys Thr Glu Asn Ser Trp Ser Asn Lys Ala
            180                 185                 190

Lys Ser Ile Cys Gln Gln Gln Lys Pro Gln Arg Arg Pro Cys Ser Glu
        195                 200                 205

Leu Leu Lys Tyr Leu Thr Thr Asn Asp Asp Pro Pro His Thr Lys Pro
    210                 215                 220

Thr Glu Asn Arg Asn Ser Ser Arg Asp Lys Cys Ala Ser Lys Lys Lys
225                 230                 235                 240

Ser His Thr Gln Pro Gln Ser Gln His Ala Gln Ala Lys Pro Thr Thr
                245                 250                 255

Leu Ser Leu Pro Leu Thr Pro Glu Ser Pro Asn Asp Pro Lys Gly Ser
                260                 265                 270

Pro Phe Glu Asn Lys Thr Ile Glu Arg Thr Leu Ser Val Glu Leu Ser
            275                 280                 285

Gly Thr Ala
    290

<210> SEQ ID NO 6
<211> LENGTH: 1893
<212> TYPE: DNA
<213> ORGANISM: Mus musculus
<220> FEATURE:
<221> NAME/KEY: CDS
<222> LOCATION: (90)...(1052)

<400> SEQUENCE: 6
gaattcggca cgaggcctgc atgagtgtgt gctgtgtgtc agagtggatt ggagttgaaa       60
aagcttgact ggcgtcattc gggagctgg atg gct tgg gac atg tgc agc caa      113
                                 Met Ala Trp Asp Met Cys Ser Gln
                                   1               5 gac tct gta tgg agt gac ata gag tgt gct gct ctg gtt ggt gag gac      161
Asp Ser Val Trp Ser Asp Ile Glu Cys Ala Ala Leu Val Gly Glu Asp
    10                  15                  20 cag cct ctt tgc cca gat ctt cct gaa ctt gac ctt tct gaa ctt gat      209
Gln Pro Leu Cys Pro Asp Leu Pro Glu Leu Asp Leu Ser Glu Leu Asp
25                  30                  35                  40 gtg aat gac ttg gat aca gac agc ttt ctg ggt gga ttg aag tgg tgt      257
Val Asn Asp Leu Asp Thr Asp Ser Phe Leu Gly Gly Leu Lys Trp Cys
                45                  50                  55 agc gac caa tcg gaa atc ata tcc aac cag tac aac aat gag cct gcg      305
Ser Asp Gln Ser Glu Ile Ile Ser Asn Gln Tyr Asn Asn Glu Pro Ala
            60                  65                  70 aac ata ttt gag aag ata gat gaa gag aat gag gcg aac ttg cta gcg      353
Asn Ile Phe Glu Lys Ile Asp Glu Glu Asn Glu Ala Asn Leu Leu Ala
        75                  80                  85 gtc ctc aca gag aca ctg gac agt ctc ccc gtg gat gaa gac gga ttg      401
Val Leu Thr Glu Thr Leu Asp Ser Leu Pro Val Asp Glu Asp Gly Leu
    90                  95                 100 ccc tca ttt gat gca ctg aca gat gga gcc gtg acc act gac aac gag      449
Pro Ser Phe Asp Ala Leu Thr Asp Gly Ala Val Thr Thr Asp Asn Glu
105                 110                 115                 120 gcc agt cct tcc tcc atg cct gac ggc acc cct ccc cct cag gag gca      497
Ala Ser Pro Ser Ser Met Pro Asp Gly Thr Pro Pro Pro Gln Glu Ala
                125                 130                 135
```

```
gaa gag ccg tct cta ctt aag aag ctc tta ctg gca cca gcc aac act    545
Glu Glu Pro Ser Leu Leu Lys Lys Leu Leu Leu Ala Pro Ala Asn Thr
            140                 145                 150 cag ctc agc tac aat gaa tgc agc ggt ctt agc act cag aac cat gca    593
Gln Leu Ser Tyr Asn Glu Cys Ser Gly Leu Ser Thr Gln Asn His Ala
        155                 160                 165 gca aac cac acc cac agg atc aga aca aac cct gcc att gtt aag acc    641
Ala Asn His Thr His Arg Ile Arg Thr Asn Pro Ala Ile Val Lys Thr
    170                 175                 180 gag aat tca tgg agc aat aaa gcg aag agc att tgt caa cag caa aag    689
Glu Asn Ser Trp Ser Asn Lys Ala Lys Ser Ile Cys Gln Gln Gln Lys
185                 190                 195                 200 cca caa aga cgt ccc tgc tca gag ctt ctc aag tat ctg acc aca aac    737
Pro Gln Arg Arg Pro Cys Ser Glu Leu Leu Lys Tyr Leu Thr Thr Asn
                205                 210                 215 gat gac cct cct cac acc aaa ccc aca gaa aac agg aac agc agc aga    785
Asp Asp Pro Pro His Thr Lys Pro Thr Glu Asn Arg Asn Ser Ser Arg
            220                 225                 230 gac aaa tgt gct tcc aaa aag aag tcc cat aca caa ccg cag tcg caa    833
Asp Lys Cys Ala Ser Lys Lys Lys Ser His Thr Gln Pro Gln Ser Gln
        235                 240                 245 cat gct caa gcc aaa cca aca act tta tct ctt cct ctg acc cca gag    881
His Ala Gln Ala Lys Pro Thr Thr Leu Ser Leu Pro Leu Thr Pro Glu
    250                 255                 260 tca cca aat gac ccc aag ggt tcc cca ttt gag aac aag act att gag    929
Ser Pro Asn Asp Pro Lys Gly Ser Pro Phe Glu Asn Lys Thr Ile Glu
265                 270                 275                 280 cga acc tta agt gtg gaa ctc tct gga act gca gct cca cta gtg cca    977
Arg Thr Leu Ser Val Glu Leu Ser Gly Thr Ala Ala Pro Leu Val Pro
                285                 290                 295 agg gag cat cca tgc atc att aca tcc agg tcg ata ttg aat gtc ttc    1025
Arg Glu His Pro Cys Ile Ile Thr Ser Arg Ser Ile Leu Asn Val Phe
            300                 305                 310 atg caa aga tgt ctt tct aat tta taa atatgaacac atcacacaac          1072
Met Gln Arg Cys Leu Ser Asn Leu *
        315                 320 ttgtgttcat tctattaaag gtgtaaaaac taatttgatt tcaaaatagc tgttgttagt  1132
aaagcaagat gagagaaagg agaatgttct tgtggcagaa ggcatttaaa tctattgcat  1192
atggagattt ttttcagac actaccaaca ggattttatg tctgaaatgg aaatggaaag   1252
gcaatgtcag cctaacaagg tgatggcttg aaacacaaga catgaaggaa ctttgttagg  1312
gaccaaaata actggtcccc aattttatgt atatacatac atgttttggc tatcactata  1372
aacatggtga aagcaatgga gctgttttat aactgataaa agatgaata gaacaaaata   1432 accagctgtc ttttttactct cggaccactg ggttctgccc atatttcctt ccattcacat 1492 atctttggtt accttgtttg aaatggggta gacatgcggt taatttggtt tgttattata  1552
ttatttgttt gaggatttca taaataagtg caatatattt gcatcatttc caccccaaca  1612
cctcccaaaa ccacccatct caaattcatt tactcttttt ctataattgt ttttgtcata  1672
tattacacac acacaaaggc gcatacacac acacgcacac acaggcacac acacacacac  1732
acacacacac acacacacac acacacactg agagttgccc taatttaggg ttgaccactt  1792
agggttcagg tctcatccct gaaaaatgaa gaagaagaag aagaagaaga agaagaagaa  1852
gaagaagaag aagaagaaga agaagaaaaa aaaaaaaaaa a                     1893

<210> SEQ ID NO 7
<211> LENGTH: 320
```

<212> TYPE: PRT
<213> ORGANISM: Mus musculus

<400> SEQUENCE: 7

Met Ala Trp Asp Met Cys Ser Gln Asp Ser Val Trp Ser Asp Ile Glu
1               5                   10                  15

Cys Ala Ala Leu Val Gly Glu Asp Gln Pro Leu Cys Pro Asp Leu Pro
            20                  25                  30

Glu Leu Asp Leu Ser Glu Leu Asp Val Asn Asp Leu Asp Thr Asp Ser
        35                  40                  45

Phe Leu Gly Gly Leu Lys Trp Cys Ser Asp Gln Ser Glu Ile Ile Ser
50                  55                  60

Asn Gln Tyr Asn Asn Glu Pro Ala Asn Ile Phe Glu Lys Ile Asp Glu
65                  70                  75                  80

Glu Asn Glu Ala Asn Leu Leu Ala Val Leu Thr Glu Thr Leu Asp Ser
                85                  90                  95

Leu Pro Val Asp Glu Asp Gly Leu Pro Ser Phe Asp Ala Leu Thr Asp
            100                 105                 110

Gly Ala Val Thr Thr Asp Asn Glu Ala Ser Pro Ser Ser Met Pro Asp
        115                 120                 125

Gly Thr Pro Pro Pro Gln Glu Ala Glu Pro Ser Leu Leu Lys Lys
130                 135                 140

Leu Leu Leu Ala Pro Ala Asn Thr Gln Leu Ser Tyr Asn Glu Cys Ser
145                 150                 155                 160

Gly Leu Ser Thr Gln Asn His Ala Ala Asn His Thr His Arg Ile Arg
                165                 170                 175

Thr Asn Pro Ala Ile Val Lys Thr Glu Asn Ser Trp Ser Asn Lys Ala
            180                 185                 190

Lys Ser Ile Cys Gln Gln Gln Lys Pro Gln Arg Arg Pro Cys Ser Glu
        195                 200                 205

Leu Leu Lys Tyr Leu Thr Thr Asn Asp Asp Pro His Thr Lys Pro
210                 215                 220

Thr Glu Asn Arg Asn Ser Ser Arg Asp Lys Cys Ala Ser Lys Lys
225                 230                 235                 240

Ser His Thr Gln Pro Gln Ser Gln His Ala Gln Ala Lys Pro Thr Thr
                245                 250                 255

Leu Ser Leu Pro Leu Thr Pro Glu Ser Pro Asn Asp Pro Lys Gly Ser
            260                 265                 270

Pro Phe Glu Asn Lys Thr Ile Glu Arg Thr Leu Ser Val Glu Leu Ser
        275                 280                 285

Gly Thr Ala Ala Pro Leu Val Pro Arg Glu His Pro Cys Ile Ile Thr
290                 295                 300

Ser Arg Ser Ile Leu Asn Val Phe Met Gln Arg Cys Leu Ser Asn Leu
305                 310                 315                 320

<210> SEQ ID NO 8
<211> LENGTH: 960
<212> TYPE: DNA
<213> ORGANISM: Mus musculus
<220> FEATURE:
<221> NAME/KEY: CDS
<222> LOCATION: (1)...(960)

<400> SEQUENCE: 8 atg gct tgg gac atg tgc agc caa gac tct gta tgg agt gac ata gag    48
Met Ala Trp Asp Met Cys Ser Gln Asp Ser Val Trp Ser Asp Ile Glu
1               5                   10                  15

-continued

| | |
|---|---|
| tgt gct gct ctg gtt ggt gag gac cag cct ctt tgc cca gat ctt cct<br>Cys Ala Ala Leu Val Gly Glu Asp Gln Pro Leu Cys Pro Asp Leu Pro<br>20                  25                  30 | 96 |
| gaa ctt gac ctt tct gaa ctt gat gtg aat gac ttg gat aca gac agc<br>Glu Leu Asp Leu Ser Glu Leu Asp Val Asn Asp Leu Asp Thr Asp Ser<br>        35                  40                  45 | 144 |
| ttt ctg ggt gga ttg aag tgg tgt agc gac caa tcg gaa atc ata tcc<br>Phe Leu Gly Gly Leu Lys Trp Cys Ser Asp Gln Ser Glu Ile Ile Ser<br>50                  55                  60 | 192 |
| aac cag tac aac aat gag cct gcg aac ata ttt gag aag ata gat gaa<br>Asn Gln Tyr Asn Asn Glu Pro Ala Asn Ile Phe Glu Lys Ile Asp Glu<br>65                  70                  75                  80 | 240 |
| gag aat gag gcg aac ttg cta gcg gtc ctc aca gag aca ctg gac agt<br>Glu Asn Glu Ala Asn Leu Leu Ala Val Leu Thr Glu Thr Leu Asp Ser<br>                85                  90                  95 | 288 |
| ctc ccc gtg gat gaa gac gga ttg ccc tca ttt gat gca ctg aca gat<br>Leu Pro Val Asp Glu Asp Gly Leu Pro Ser Phe Asp Ala Leu Thr Asp<br>        100                 105                 110 | 336 |
| gga gcc gtg acc act gac aac gag gcc agt cct tcc tcc atg cct gac<br>Gly Ala Val Thr Thr Asp Asn Glu Ala Ser Pro Ser Ser Met Pro Asp<br>115                 120                 125 | 384 |
| ggc acc cct ccc cct cag gag gca gaa gag ccg tct cta ctt aag aag<br>Gly Thr Pro Pro Pro Gln Glu Ala Glu Glu Pro Ser Leu Leu Lys Lys<br>130                 135                 140 | 432 |
| ctc tta ctg gca cca gcc aac act cag ctc agc tac aat gaa tgc agc<br>Leu Leu Leu Ala Pro Ala Asn Thr Gln Leu Ser Tyr Asn Glu Cys Ser<br>145                 150                 155                 160 | 480 |
| ggt ctt agc act cag aac cat gca gca aac cac acc cac agg atc aga<br>Gly Leu Ser Thr Gln Asn His Ala Ala Asn His Thr His Arg Ile Arg<br>                165                 170                 175 | 528 |
| aca aac cct gcc att gtt aag acc gag aat tca tgg agc aat aaa gcg<br>Thr Asn Pro Ala Ile Val Lys Thr Glu Asn Ser Trp Ser Asn Lys Ala<br>        180                 185                 190 | 576 |
| aag agc att tgt caa cag caa aag cca caa aga cgt ccc tgc tca gag<br>Lys Ser Ile Cys Gln Gln Gln Lys Pro Gln Arg Arg Pro Cys Ser Glu<br>195                 200                 205 | 624 |
| ctt ctc aag tat ctg acc aca aac gat gac cct cct cac acc aaa ccc<br>Leu Leu Lys Tyr Leu Thr Thr Asn Asp Asp Pro Pro His Thr Lys Pro<br>210                 215                 220 | 672 |
| aca gaa aac agg aac agc agc aga gac aaa tgt gct tcc aaa aag aag<br>Thr Glu Asn Arg Asn Ser Ser Arg Asp Lys Cys Ala Ser Lys Lys Lys<br>225                 230                 235                 240 | 720 |
| tcc cat aca caa ccg cag tcg caa cat gct caa gcc aaa cca aca act<br>Ser His Thr Gln Pro Gln Ser Gln His Ala Gln Ala Lys Pro Thr Thr<br>                245                 250                 255 | 768 |
| tta tct ctt cct ctg acc cca gag tca cca aat gac ccc aag ggt tcc<br>Leu Ser Leu Pro Leu Thr Pro Glu Ser Pro Asn Asp Pro Lys Gly Ser<br>        260                 265                 270 | 816 |
| cca ttt gag aac aag act att gag cga acc tta agt gtg gaa ctc tct<br>Pro Phe Glu Asn Lys Thr Ile Glu Arg Thr Leu Ser Val Glu Leu Ser<br>275                 280                 285 | 864 |
| gga act gca gct cca cta gtg cca agg gag cat cca tgc atc att aca<br>Gly Thr Ala Ala Pro Leu Val Pro Arg Glu His Pro Cys Ile Ile Thr<br>290                 295                 300 | 912 |
| tcc agg tcg ata ttg aat gtc ttc atg caa aga tgt ctt tct aat tta<br>Ser Arg Ser Ile Leu Asn Val Phe Met Gln Arg Cys Leu Ser Asn Leu<br>305                 310                 315                 320 | 960 |

<210> SEQ ID NO 9

-continued

```
<211> LENGTH: 931
<212> TYPE: DNA
<213> ORGANISM: Mus musculus

<400> SEQUENCE: 9
gctccactag tgccaaggga gcatccatgc atcattacat ccaggtcgat attgaatgtc    60
ttcatgcaaa gatgtctttc taatttataa atatgaacac atcacacaac ttgtgttcat   120
tctattaaag gtgtaaaaac taatttgatt tcaaaatagc tgttgttagt aaagcaagat   180
gagagaaagg agaatgttct tgtggcagaa ggcatttaaa tctattgcat atggagattt   240
tttttcagac actaccaaca ggattttatg tctgaaatgg aaatggaaag gcaatgtcag   300
cctaacaagg tgatggcttg aaacacaaga catgaaggaa ctttgttagg gaccaaaata   360
actggtcccc aattttatgt atatacatac atgttttggc tatcactata acatggtgaa   420
aagcaatgga gctgttttat aactgataaa aagatgaata gaacaaaata accagctgtc   480 ttttactct cggaccactg ggttctgccc atatttcctt ccattcacat atctttggtt    540
accttgtttg aaatggggta gacatgcggt taatttggtt tgttattata ttatttgttt   600
gaggatttca taaataagtg caatatattt gcatcatttc caccccaaca cctcccaaaa   660
ccacccatct caaattcatt tactctttt ctataattgt ttttgtcata tattacacac    720
acacaaaggc gcatacacac acacgcacac acaggcacac acacacacac acacacacac   780
acacacacac acacacactg agagttgccc taatttaggg ttgaccactt agggttcagg   840
tctcatccct gaaaatgaa gaagaagaag aagaagaaga agaagaagaa gaagaagaag    900
aagaagaaga agagaaaaa aaaaaaaaaa a                                   931

<210> SEQ ID NO 10
<211> LENGTH: 29
<212> TYPE: PRT
<213> ORGANISM: Mus musculus

<400> SEQUENCE: 10

Ala Pro Leu Val Pro Arg Glu His Pro Cys Ile Ile Thr Ser Arg Ser
 1               5                  10                  15

Ile Leu Asn Val Phe Met Gln Arg Cys Leu Ser Asn Leu
             20                  25

<210> SEQ ID NO 11
<211> LENGTH: 87
<212> TYPE: DNA
<213> ORGANISM: Mus musculus
<220> FEATURE:
<221> NAME/KEY: CDS
<222> LOCATION: (1)...(87)

<400> SEQUENCE: 11 gct cca cta gtg cca agg gag cat cca tgc atc att aca tcc agg tcg    48
Ala Pro Leu Val Pro Arg Glu His Pro Cys Ile Ile Thr Ser Arg Ser
 1               5                  10                  15 ata ttg aat gtc ttc atg caa aga tgt ctt tct aat tta                87
Ile Leu Asn Val Phe Met Gln Arg Cys Leu Ser Asn Leu
             20                  25

<210> SEQ ID NO 12
<211> LENGTH: 1744
<212> TYPE: DNA
<213> ORGANISM: Mus musculus
<220> FEATURE:
<221> NAME/KEY: CDS
<222> LOCATION: (67)...(969)
```

```
<220> FEATURE:
<221> NAME/KEY: misc_feature
<222> LOCATION: 1543
<223> OTHER INFORMATION: n = A,T,C or G

<400> SEQUENCE: 12
gaattcggca cgaggtcaga gtggattgga gttgaaaaag cttgactggc gtcattcggg      60 agctgg atg gct tgg gac atg tgc agc caa gac tct gta tgg agt gac       108
       Met Ala Trp Asp Met Cys Ser Gln Asp Ser Val Trp Ser Asp
       1               5                   10 ata gag tgt gct gct ctg gtt ggt gag gac cag cct ctt tgc cca gat      156
Ile Glu Cys Ala Ala Leu Val Gly Glu Asp Gln Pro Leu Cys Pro Asp
15                  20                  25                  30 ctt cct gaa ctt gac ctt tct gaa ctt gat gtg aat gac ttg gat aca      204
Leu Pro Glu Leu Asp Leu Ser Glu Leu Asp Val Asn Asp Leu Asp Thr
                35                  40                  45 gac agc ttt ctg ggt gga ttg aag tgg tgt agc gac caa tcg gaa atc      252
Asp Ser Phe Leu Gly Gly Leu Lys Trp Cys Ser Asp Gln Ser Glu Ile
            50                  55                  60 ata tcc aac cag tac aac aat gag cct gcg aac ata ttt gag aag ata      300
Ile Ser Asn Gln Tyr Asn Asn Glu Pro Ala Asn Ile Phe Glu Lys Ile
        65                  70                  75 gat gaa gag aat gag gca aac ttg cta gcg gtc ctc aca gag aca ctg      348
Asp Glu Glu Asn Glu Ala Asn Leu Leu Ala Val Leu Thr Glu Thr Leu
    80                  85                  90 gac agt ctc ccc gtg gat gaa gac gga ttg ccc tca ttt gat gca ctg      396
Asp Ser Leu Pro Val Asp Glu Asp Gly Leu Pro Ser Phe Asp Ala Leu
95                  100                 105                 110 aca gat gga gcc gtg acc act gac aac gag gcc agt cct tcc tcc atg      444
Thr Asp Gly Ala Val Thr Thr Asp Asn Glu Ala Ser Pro Ser Ser Met
                115                 120                 125 cct gac ggc acc cct ccc cct cag gag gca gaa gag ccg tct cta ctt      492
Pro Asp Gly Thr Pro Pro Pro Gln Glu Ala Glu Glu Pro Ser Leu Leu
            130                 135                 140 aag aag ctc tta ctg gca cca gcc aac act cag ctc agc tac aat gaa      540
Lys Lys Leu Leu Leu Ala Pro Ala Asn Thr Gln Leu Ser Tyr Asn Glu
        145                 150                 155 tgc agc ggt ctt agc act cag aac cat gca gca aac cac acc cac agg      588
Cys Ser Gly Leu Ser Thr Gln Asn His Ala Ala Asn His Thr His Arg
    160                 165                 170 atc aga aca aac cct gcc att gtt aag acc gag aat tca tgg agc aat      636
Ile Arg Thr Asn Pro Ala Ile Val Lys Thr Glu Asn Ser Trp Ser Asn
175                 180                 185                 190 aaa gcg aag agc att tgt caa cag caa aag cca caa aga cgt ccc tgc      684
Lys Ala Lys Ser Ile Cys Gln Gln Gln Lys Pro Gln Arg Arg Pro Cys
                195                 200                 205 tca gag ctt ctc aag tat ctg acc aca aac gat gac cct cct cac acc      732
Ser Glu Leu Leu Lys Tyr Leu Thr Thr Asn Asp Asp Pro Pro His Thr
            210                 215                 220 aaa ccc aca gaa aac agg aac agc agc aga gac aaa tgt gct tcc aaa      780
Lys Pro Thr Glu Asn Arg Asn Ser Ser Arg Asp Lys Cys Ala Ser Lys
        225                 230                 235 aag aag tcc cat aca caa ccg cag tcg caa cat gct caa gcc aaa cca      828
Lys Lys Ser His Thr Gln Pro Gln Ser Gln His Ala Gln Ala Lys Pro
    240                 245                 250 aca act tta tct ctt cct ctg acc cca gag tca cca aat gac ccc aag      876
Thr Thr Leu Ser Leu Pro Leu Thr Pro Glu Ser Pro Asn Asp Pro Lys
255                 260                 265                 270 ggt tcc cca ttt gag aac aag act att gag cga acc tta agt gtg gaa      924
Gly Ser Pro Phe Glu Asn Lys Thr Ile Glu Arg Thr Leu Ser Val Glu
```

-continued

```
                275               280               285
ctc tct gga act gca ggt gta aaa act aat ttg att tca aaa tag        969
Leu Ser Gly Thr Ala Gly Val Lys Thr Asn Leu Ile Ser Lys  *
                290               295               300 ctgttgttag ttaagcaaga tgagagaaag gagaatgttc ttgtggcaga aggcatttaa 1029 atctattgca tatggagatt ttttttcaga cactaccaac aggattttat gtctgaaatg 1089 gaaatggaaa ggcaatgtca gcctaacaag gtgatggctt gaaacacaag acatgaagga 1149 actttgttag ggaccaaaat aactggtccc caattttatg tatatacata catgttttgg 1209 ctatcactat aaacatggtg aaagcaatgg agctgtttta taactgataa aaagatgaat 1269 agaacaaaat aaccagctgt cttttttactc tcggaccact gggttctgcc catatttcct 1329 tccattcaca tatctttggt taccttgttt gaaatggggt agacatgcgg ttaatttggt 1389 ttgttattat attatttgtt tgaggatttc ataaataagt gcaatatatt tgcatcattt 1449 ccacccaac acctcccaaa accacccatc tcaaattcat ttactctttt tctataattg 1509 tttttgtcat atattacaca cacacaaagg cacntacaca cacacgcaca cacaggcaca 1569 cacacacaca cacacacaca cacacacaca cacacacact gagaattgcc ctaatttagg 1629 gttgaccact tagggttcag tttttttccc tggaaaatgg ggggggggga aaaaaaaaaa 1689 aaaaaaaaaa aaaaaaaaaa aaaaaaaaaa aaaaaaaaaa aaaaaaaaaa aaaaa      1744
```

<210> SEQ ID NO 13
<211> LENGTH: 300
<212> TYPE: PRT
<213> ORGANISM: Mus musculus

<400> SEQUENCE: 13

```
Met Ala Trp Asp Met Cys Ser Gln Asp Ser Val Trp Ser Asp Ile Glu
  1               5                  10                  15

Cys Ala Ala Leu Val Gly Glu Asp Gln Pro Leu Cys Pro Asp Leu Pro
                 20                  25                  30

Glu Leu Asp Leu Ser Glu Leu Asp Val Asn Asp Leu Asp Thr Asp Ser
             35                  40                  45

Phe Leu Gly Gly Leu Lys Trp Cys Ser Asp Ser Glu Ile Ile Ser
         50                  55                  60

Asn Gln Tyr Asn Asn Glu Pro Ala Asn Ile Phe Glu Lys Ile Asp Glu
 65                  70                  75                  80

Glu Asn Glu Ala Asn Leu Leu Ala Val Leu Thr Glu Thr Leu Asp Ser
                 85                  90                  95

Leu Pro Val Asp Glu Asp Gly Leu Pro Ser Phe Asp Ala Leu Thr Asp
                100                 105                 110

Gly Ala Val Thr Thr Asp Asn Glu Ala Ser Pro Ser Ser Met Pro Asp
            115                 120                 125

Gly Thr Pro Pro Pro Gln Glu Ala Glu Pro Ser Leu Leu Lys Lys
        130                 135                 140

Leu Leu Leu Ala Pro Ala Asn Thr Gln Leu Ser Tyr Asn Glu Cys Ser
145                 150                 155                 160

Gly Leu Ser Thr Gln Asn His Ala Ala Asn His Thr His Arg Ile Arg
                165                 170                 175

Thr Asn Pro Ala Ile Val Lys Thr Glu Asn Ser Trp Ser Asn Lys Ala
            180                 185                 190

Lys Ser Ile Cys Gln Gln Gln Lys Pro Gln Arg Arg Pro Cys Ser Glu
        195                 200                 205
```

```
Leu Leu Lys Tyr Leu Thr Thr Asn Asp Asp Pro His Thr Lys Pro
    210                 215                 220

Thr Glu Asn Arg Asn Ser Ser Arg Asp Lys Cys Ala Ser Lys Lys Lys
225                 230                 235                 240

Ser His Thr Gln Pro Gln Ser Gln His Ala Gln Ala Lys Pro Thr Thr
                    245                 250                 255

Leu Ser Leu Pro Leu Thr Pro Glu Ser Pro Asn Asp Pro Lys Gly Ser
                260                 265                 270

Pro Phe Glu Asn Lys Thr Ile Glu Arg Thr Leu Ser Val Glu Leu Ser
            275                 280                 285

Gly Thr Ala Gly Val Lys Thr Asn Leu Ile Ser Lys
290                 295                 300

<210> SEQ ID NO 14
<211> LENGTH: 900
<212> TYPE: DNA
<213> ORGANISM: Mus musculus
<220> FEATURE:
<221> NAME/KEY: CDS
<222> LOCATION: (1)...(900)

<400> SEQUENCE: 14
```

| atg gct tgg gac atg tgc agc caa gac tct gta tgg agt gac ata gag | 48 |
|---|---|
| Met Ala Trp Asp Met Cys Ser Gln Asp Ser Val Trp Ser Asp Ile Glu | |
| 1               5                   10                  15 | |

| tgt gct gct ctg gtt ggt gag gac cag cct ctt tgc cca gat ctt cct | 96 |
|---|---|
| Cys Ala Ala Leu Val Gly Glu Asp Gln Pro Leu Cys Pro Asp Leu Pro | |
|                 20                  25                  30 | |

| gaa ctt gac ctt tct gaa ctt gat gtg aat gac ttg gat aca gac agc | 144 |
|---|---|
| Glu Leu Asp Leu Ser Glu Leu Asp Val Asn Asp Leu Asp Thr Asp Ser | |
|             35                  40                  45 | |

| ttt ctg ggt gga ttg aag tgg tgt agc gac caa tcg gaa atc ata tcc | 192 |
|---|---|
| Phe Leu Gly Gly Leu Lys Trp Cys Ser Asp Gln Ser Glu Ile Ile Ser | |
|         50                  55                  60 | |

| aac cag tac aac aat gag cct gcg aac ata ttt gag aag ata gat gaa | 240 |
|---|---|
| Asn Gln Tyr Asn Asn Glu Pro Ala Asn Ile Phe Glu Lys Ile Asp Glu | |
| 65                  70                  75                  80 | |

| gag aat gag gca aac ttg cta gcg gtc ctc aca gag aca ctg gac agt | 288 |
|---|---|
| Glu Asn Glu Ala Asn Leu Leu Ala Val Leu Thr Glu Thr Leu Asp Ser | |
|                 85                  90                  95 | |

| ctc ccc gtg gat gaa gac gga ttg ccc tca ttt gat gca ctg aca gat | 336 |
|---|---|
| Leu Pro Val Asp Glu Asp Gly Leu Pro Ser Phe Asp Ala Leu Thr Asp | |
|             100                 105                 110 | |

| gga gcc gtg acc act gac aac gag gcc agt cct tcc tcc atg cct gac | 384 |
|---|---|
| Gly Ala Val Thr Thr Asp Asn Glu Ala Ser Pro Ser Ser Met Pro Asp | |
|         115                 120                 125 | |

| ggc acc cct ccc cct cag gag gca gaa gag ccg tct cta ctt aag aag | 432 |
|---|---|
| Gly Thr Pro Pro Pro Gln Glu Ala Glu Glu Pro Ser Leu Leu Lys Lys | |
| 130                 135                 140 | |

| ctc tta ctg gca cca gcc aac act cag ctc agc tac aat gaa tgc agc | 480 |
|---|---|
| Leu Leu Leu Ala Pro Ala Asn Thr Gln Leu Ser Tyr Asn Glu Cys Ser | |
| 145                 150                 155                 160 | |

| ggt ctt agc act cag aac cat gca gca aac cac acc cac agg atc aga | 528 |
|---|---|
| Gly Leu Ser Thr Gln Asn His Ala Ala Asn His Thr His Arg Ile Arg | |
|                 165                 170                 175 | |

| aca aac cct gcc att gtt aag acc gag aat tca tgg agc aat aaa gcg | 576 |
|---|---|
| Thr Asn Pro Ala Ile Val Lys Thr Glu Asn Ser Trp Ser Asn Lys Ala | |
|             180                 185                 190 | |

| aag agc att tgt caa cag caa aag cca caa aga cgt ccc tgc tca gag | 624 |
|---|---|
| Lys Ser Ile Cys Gln Gln Gln Lys Pro Gln Arg Arg Pro Cys Ser Glu | |

```
ctt ctc aag tat ctg acc aca aac gat gac cct cct cac acc aaa ccc    672
Leu Leu Lys Tyr Leu Thr Thr Asn Asp Asp Pro Pro His Thr Lys Pro
        210                 215                 220 aca gaa aac agg aac agc agc aga gac aaa tgt gct tcc aaa aag aag    720
Thr Glu Asn Arg Asn Ser Ser Arg Asp Lys Cys Ala Ser Lys Lys Lys
225                 230                 235                 240 tcc cat aca caa ccg cag tcg caa cat gct caa gcc aaa cca aca act    768
Ser His Thr Gln Pro Gln Ser Gln His Ala Gln Ala Lys Pro Thr Thr
                245                 250                 255 tta tct ctt cct ctg acc cca gag tca cca aat gac ccc aag ggt tcc    816
Leu Ser Leu Pro Leu Thr Pro Glu Ser Pro Asn Asp Pro Lys Gly Ser
        260                 265                 270 cca ttt gag aac aag act att gag cga acc tta agt gtg gaa ctc tct    864
Pro Phe Glu Asn Lys Thr Ile Glu Arg Thr Leu Ser Val Glu Leu Ser
    275                 280                 285 gga act gca ggt gta aaa act aat ttg att tca aaa                    900
Gly Thr Ala Gly Val Lys Thr Asn Leu Ile Ser Lys
290                 295                 300

<210> SEQ ID NO 15
<211> LENGTH: 805
<212> TYPE: DNA
<213> ORGANISM: Mus musculus
<220> FEATURE:
<221> NAME/KEY: misc_feature
<222> LOCATION: 604
<223> OTHER INFORMATION: n = A,T,C or G

<400> SEQUENCE: 15
ggtgtaaaaa ctaatttgat ttcaaaatag ctgttgttag ttaagcaaga tgagagaaag     60
gagaatgttc ttgtggcaga aggcatttaa atctattgca tatggagatt tttttttcaga   120 cactaccaac aggattttat gtctgaaatg gaaatggaaa ggcaatgtca gcctaacaag    180
gtgatggctt gaaacacaag acatgaagga actttgttag ggaccaaaat aactggtccc    240
caattttatg tatatacata catgttttgg ctatcactat aaacatggtg aaagcaatgg    300
agctgtttta taactgataa aagatgaat agaacaaaat aaccagctgt cttttactc     360 tcggaccact gggttctgcc catatttcct tccattcaca tatctttggt taccttgttt    420
gaaatggggt agacatgcgg ttaatttggt ttgttattat attatttgtt tgaggatttc    480
ataaataagt gcaatatatt tgcatcattt ccaccccaac acctcccaaa accacccatc    540
tcaaattcat ttactctttt tctataattg tttttgtcat atattacaca cacacaaagg    600
cacntacaca cacacgcaca cacaggcaca cacacacaca cacacacaca cacacacaca    660
cacacacact gagaattgcc ctaatttagg gttgaccact tagggttcag ttttttttccc    720 tggaaaatgg ggggggggga aaaaaaaaaa aaaaaaaaaa aaaaaaaaaa aaaaaaaaaa    780
aaaaaaaaaa aaaaaaaaa aaaaa                                          805

<210> SEQ ID NO 16
<211> LENGTH: 9
<212> TYPE: PRT
<213> ORGANISM: Mus musculus

<400> SEQUENCE: 16

Gly Val Lys Thr Asn Leu Ile Ser Lys
1               5

<210> SEQ ID NO 17
```

```
<211> LENGTH: 27
<212> TYPE: DNA
<213> ORGANISM: Mus musculus
<220> FEATURE:
<221> NAME/KEY: CDS
<222> LOCATION: (1)...(27)

<400> SEQUENCE: 17 ggt gta aaa act aat ttg att tca aaa                                    27
Gly Val Lys Thr Asn Leu Ile Ser Lys
 1               5
```